US008637656B2

(12) United States Patent
Nakamura et al.

(10) Patent No.: US 8,637,656 B2
(45) Date of Patent: Jan. 28, 2014

(54) NUCLEIC ACID CAPABLE OF BINDING TO IMMUNOGLOBULIN G AND USE THEREOF

(75) Inventors: Yoshikazu Nakamura, Tokyo (JP); Shin Miyakawa, Tokyo (JP)

(73) Assignee: Ribomic Inc., Tokyo (JP)

( * ) Notice: Subject to any disclaimer, the term of this patent is extended or adjusted under 35 U.S.C. 154(b) by 627 days.

(21) Appl. No.: 11/988,164

(22) PCT Filed: Jul. 5, 2006

(86) PCT No.: PCT/JP2006/313811
§ 371 (c)(1),
(2), (4) Date: Apr. 1, 2008

(87) PCT Pub. No.: WO2007/004748
PCT Pub. Date: Jan. 11, 2007

(65) Prior Publication Data
US 2009/0170219 A1 Jul. 2, 2009

Related U.S. Application Data

(60) Provisional application No. 60/749,026, filed on Dec. 12, 2005.

(30) Foreign Application Priority Data

Jul. 5, 2005 (JP) ................................ 2005-195717

(51) Int. Cl.
*C07H 21/04* (2006.01)
*C12Q 1/68* (2006.01)
*A61K 48/00* (2006.01)

(52) U.S. Cl.
USPC .......... 536/24.5; 536/23.1; 514/44 R; 435/6.1

(58) Field of Classification Search
None
See application file for complete search history.

(56) References Cited

U.S. PATENT DOCUMENTS

| 5,270,163 | A | 12/1993 | Gold et al. | |
|---|---|---|---|---|
| 5,670,637 | A | 9/1997 | Gold et al. | |
| 5,686,592 | A | 11/1997 | Wiegand et al. | |
| 5,756,291 | A * | 5/1998 | Griffin et al. | 435/6 |
| 5,840,867 | A | 11/1998 | Toole et al. | |
| 6,344,321 | B1 * | 2/2002 | Rabin et al. | 435/6 |
| 7,572,644 | B2 * | 8/2009 | Lee et al. | 436/532 |
| 2003/0049644 | A1 | 3/2003 | Rabin et al. | |
| 2005/0124565 | A1 * | 6/2005 | Diener et al. | 514/44 |
| 2009/0018093 | A1 * | 1/2009 | Cload et al. | 514/44 |

FOREIGN PATENT DOCUMENTS

| JP | 2002-300885 | 10/2002 |
|---|---|---|
| JP | 2004-344008 | 12/2004 |
| WO | 91/19813 | 12/1991 |
| WO | 92/14843 | 9/1992 |
| WO | 94/08050 | 4/1994 |
| WO | 95/07364 | 3/1995 |
| WO | 01/09157 | 2/2001 |
| WO | 01/09159 | 2/2001 |
| WO | 2004/098384 | 11/2004 |
| WO | 2004/104586 | 12/2004 |

OTHER PUBLICATIONS

Sumedha D. Jayasena, Aptamers: An emerging class of molecules that rival antibodies in diagnostics, 1999, Clinical Chemistry, vol. 45, pp. 1628-1650.*
Marino et al., Prevention of systemic lupus erythematosus in MRL/lpr mice by administration of an immunoglobulin-binding peptide, 2000, Nature Biotechnology, vol. 18, pp. 735-739.*
Doudna et al., Selection of an RNA molecule that mimics a major autoantigenic epitope of human insulin receptor, 1995, PNAS, vol. 92, pp. 2355-2359.*
Sondermann et al., The 3.2-A crystal structure of the human IgG1 Fc fragment-Fcgamma RIII complex, 2000, Nature, vol. 406, pp. 267-273.*
Ridgway et al., 'Knobs-into-holes' engineering of antibody CH3 domains for heavy chain heterodimerization, 1996, Protein Engineering, vol. 9, pp. 617-621.*
Nakamura et al., Production of the human immunoglobulin gamma 1 chain constant region polypeptides in *Escherichia coli*, 1988, Journal of Biotechnology, vol. 8, pp. 141-148.*
Sotiris Missailidis, Targeting of antibodies using aptamers, 2004, Methods in Molecular Biology, vol. 248, pp. 547-555.*
Supplementary European Search Report issued Jul. 15, 2009 in European Application No. EP 06 78 0981.
Y. Nakamura et al., "Development of novel whole-cell immunoadsorbents by yeast surface display of the IgG-binding domain", Applied Microbiology and Biotechnology, vol. 57, pp. 500-505, 2001.
M. Famulok et al., "Aptamers as Tools in Molecular Biology and Immunology", Current Topics in Microbiology and Immunology, vol. 243, pp. 123-136, 1999.
T. W. Wiegand et al., "High-Affinity Oligonucleotide Ligands to Human IgE Inhibit Binding to Fcε Receptor I", The Journal of Immunology, vol. 157, pp. 221-230, 1996.
L. Gold et al., "Diversity of Oligonucleotide Functions", Annual Review of Biochemistry, vol. 64, pp. 763-797, 1995.
S. P. Ohuchi et al., "Selection of RNA aptamers against recombinant transforming growth factor-β type III receptor displayed on cell surface", Biochemie, vol. 88, pp. 897-904, 2006.

(Continued)

*Primary Examiner* — Dana Shin
(74) *Attorney, Agent, or Firm* — Wenderoth, Lind & Ponack, L.L.P.

(57) ABSTRACT

The present invention provides a novel aptamer for IgG and a method for utilizing the same and the like. More specifically, the present invention provides an aptamer that binds to an Fc region of IgG (e.g., human IgG); a complex comprising an aptamer and a functional substance bound thereto (e.g., affinity substance, labeling substance, enzyme, drug, toxin, drug delivery vehicle); a solid phase carrier with an aptamer or complex immobilized thereon; medical equipment comprising a solid phase carrier; a method for antibody purification comprising adsorbing an IgG antibody to a solid phase carrier, and eluting the adsorbed IgG antibody with an eluent; a method for producing a purified antibody, comprising preparing an IgG antibody and purifying the prepared IgG antibody with a solid phase carrier and the like.

21 Claims, 37 Drawing Sheets

(56) References Cited

OTHER PUBLICATIONS

S. Miyakawa et al., "Structural and molecular basis for hyperspecificity of RNA aptamer to human immunoglobulin G", RNA, vol. 14, pp. 1154-1163, 2008.

S. Sugiyama et al., "Crystallization and preliminary X-ray diffraction studies of an RNA aptamer in complex with the human IgG Fc Fragment", Acta Crystallographica. Section F, vol. 64, pp. 942-944, 2008.

Sakai et al., "RNA aptamers specifically interact with the Fc region of mouse immunoglobulin G", Nucleic Acids Symposium Series No. 52, pp. 487-488, 2008.

S. Missailidis et al., "Selection of Aptamers with High Affinity and High Specificity Against C595, an Anti-MUC1 IgG3 Monoclonal Antibody, for Antibody Targeting", Journal of Immunological Methods, vol. 296, pp. 45-62, 2005.

K. Stadtherr et al., "An Aptamer-Based Protein Biochip", Analytical Chemistry, vol. 77, No. 11, pp. 3437-3443, Jun. 1, 2005.

A. D. Ellington et al., "In Vitro Selection of RNA Molecules that Bind Specific Ligands", Nature, vol. 346, pp. 818-822, Aug. 30, 1990.

C. Tuerk et al., "Systematic Evolution of Ligands by Exponential Enrichment: RNA Ligands to Bacteriophage T4 DNA Polymerase", Science, vol. 249, pp. 505-510, 1990.

A. Oguro et al., "RNA Aptamers to Initiation Factor 4A Helicase hinder CAP-Dependent Translation by Blocking ATP Hydrolysis", RNA, vol. 9, pp. 394-407, 2003.

K. Mochizuki et al., "High Affinity RNA for Mammalian Initiation Factor 4E Interferes with mRNA-cap Binding and Inhibits Translation", RNA, vol. 11, pp. 77-89, 2005.

T. Mori et al., "RNA Aptamers Selected Against the Receptor Activator of NF-kB Acquire General Affinity to Proteins of the Tumor Necrosis Factor Receptor Family", Nucleic Acids Research, vol. 32, No. 20, pp. 6120-6128, 2004.

Y. M. Kim et al., "Specific Modulation of the Anti-DNA Autoantibody-Nucleic Acids Interaction by the High Affinity RNA Aptamer", Biochemical and Biophysical Research Communications, vol. 300, pp. 516-523, 2003.

T. S. Romig et al ., "Aptamer Affinity Chromatography: Combinatorial Chemistry Applied to Protein Purification", Journal of Chromatography, vol. 731, pp. 275-284, 1999.

M. Blank et al., "Systematic Evolution of a DNA Aptamer Binding to Rat Brain Tumor Microvessels", The Journal of Biological Chemistry, vol. 276, No. 19, pp. 16464-16468, May 11, 2001.

* cited by examiner

SEQUENCE LISTING

```
<160> NUMBER OF SEQ ID NOS: 33

<210> SEQ ID NO 1
<211> LENGTH: 73
<212> TYPE: RNA
<213> ORGANISM: Artificial sequence
<220> FEATURE:
<223> OTHER INFORMATION: Synthetic construct

<400> SEQUENCE: 1
```

```
gggacacaau ggacgaguua caggugcucc aucaacaaaa uguuacaugg aacuguaacg    60
gccgacauga gag                                                      73

<210> SEQ ID NO 2
<211> LENGTH: 71
<212> TYPE: RNA
<213> ORGANISM: Artificial sequence
<220> FEATURE:
<223> OTHER INFORMATION: Synthetic construct

<400> SEQUENCE: 2
gggacacaau ggacgucaaa gaagaggugc ucugcgagcc acgcggaacu cuauaacggc    60
cgacaugaga g                                                        71

<210> SEQ ID NO 3
<211> LENGTH: 74
<212> TYPE: RNA
<213> ORGANISM: Artificial sequence
<220> FEATURE:
<223> OTHER INFORMATION: Synthetic construct

<400> SEQUENCE: 3
gggacacaau ggacggcgua aaauggaacc uggguuagaa uaucgggggu gcuccguaac    60
ggccgacaug agag                                                     74

<210> SEQ ID NO 4
<211> LENGTH: 71
<212> TYPE: RNA
<213> ORGANISM: Artificial sequence
<220> FEATURE:
<223> OTHER INFORMATION: Synthetic construct

<400> SEQUENCE: 4
gggacacaau ggacggccaa cguuaacugg aacuguaaau caggugcucg agauaacggc    60
cgacaugaga g                                                        71

<210> SEQ ID NO 5
<211> LENGTH: 72
<212> TYPE: RNA
<213> ORGANISM: Artificial sequence
<220> FEATURE:
<223> OTHER INFORMATION: Synthetic construct

<400> SEQUENCE: 5
gggacacaau ggacgacuac aaggugcucc uugaaauguu aaaugaggaa cuuguaacgg    60
ccgacaugag ag                                                       72

<210> SEQ ID NO 6
<211> LENGTH: 73
<212> TYPE: RNA
<213> ORGANISM: Artificial sequence
<220> FEATURE:
<223> OTHER INFORMATION: Synthetic construct

<400> SEQUENCE: 6
gggacacaau ggacggcugg uaaggugcuc ggaauggaac ucgucauucg gaacuuaacg    60
gccgacauga gag                                                      73

<210> SEQ ID NO 7
<211> LENGTH: 72
<212> TYPE: RNA
<213> ORGANISM: Artificial sequence
<220> FEATURE:
```

<223> OTHER INFORMATION: Synthetic construct

<400> SEQUENCE: 7
gggacacaau ggacgggugu acaggugcu ugauaaaggu agaaaaucaa acuguaacgg    60
ccgacaugag ag    72

<210> SEQ ID NO 8
<211> LENGTH: 72
<212> TYPE: RNA
<213> ORGANISM: Artificial sequence
<220> FEATURE:
<223> OTHER INFORMATION: Synthetic construct

<400> SEQUENCE: 8
gggacacaau ggacgaaagg ugcuccaacu aaauuuggaa cuuccaccc auaauaacgg    60 ccgacaugag ag    72

<210> SEQ ID NO 9
<211> LENGTH: 67
<212> TYPE: RNA
<213> ORGANISM: Artificial sequence
<220> FEATURE:
<223> OTHER INFORMATION: Synthetic construct

<400> SEQUENCE: 9
gggccacagc gaggugcucc accauucacg uggaacucgu gggcagcccg uccccgcgug    60
uggucgg    67

<210> SEQ ID NO 10
<211> LENGTH: 63
<212> TYPE: RNA
<213> ORGANISM: Artificial sequence
<220> FEATURE:
<223> OTHER INFORMATION: Synthetic construct

<400> SEQUENCE: 10
ggaauggacg aguuacaggu gcuccaucaa caaaauguua cauggaacug uaacggccga    60
cau    63

<210> SEQ ID NO 11
<211> LENGTH: 54
<212> TYPE: RNA
<213> ORGANISM: Artificial sequence
<220> FEATURE:
<223> OTHER INFORMATION: Synthetic construct

<400> SEQUENCE: 11
ggacgaguua caggugcucc aucaacaaaa uguuacaugg aacuguaacg gccg    54

<210> SEQ ID NO 12
<211> LENGTH: 41
<212> TYPE: RNA
<213> ORGANISM: Artificial
<220> FEATURE:
<223> OTHER INFORMATION: Synthetic construct

<400> SEQUENCE: 12
ggacaggugc uccaucaaca aaauguuaca uggaacuguc c    41

<210> SEQ ID NO 13
<211> LENGTH: 34
<212> TYPE: RNA
<213> ORGANISM: Artificial sequence
<220> FEATURE:

<223> OTHER INFORMATION: Synthetic construct

<400> SEQUENCE: 13
ggacaggugc ucugcgagcc acgcggaacu gucc          34

<210> SEQ ID NO 14
<211> LENGTH: 33
<212> TYPE: RNA
<213> ORGANISM: Artificial sequence
<220> FEATURE:
<223> OTHER INFORMATION: Synthetic construct

<400> SEQUENCE: 14
ggacaggugc ucugcggaaa cgcggaacug ucc           33

<210> SEQ ID NO 15
<211> LENGTH: 30
<212> TYPE: RNA
<213> ORGANISM: Artificial sequence
<220> FEATURE:
<223> OTHER INFORMATION: Synthetic construct

<400> SEQUENCE: 15
ggaggugcuc ugcgagccac gcggaacucc              30

<210> SEQ ID NO 16
<211> LENGTH: 27
<212> TYPE: RNA
<213> ORGANISM: Artificial sequence
<220> FEATURE:
<223> OTHER INFORMATION: Synthetic construct

<400> SEQUENCE: 16
ggacaggugc uccgaaagga acugucc                 27

<210> SEQ ID NO 17
<211> LENGTH: 23
<212> TYPE: RNA
<213> ORGANISM: Artificial sequence
<220> FEATURE:
<223> OTHER INFORMATION: Synthetic construct

<400> SEQUENCE: 17
ggaggugcuc cgaaaggaac ucc                     23

<210> SEQ ID NO 18
<211> LENGTH: 21
<212> TYPE: RNA
<213> ORGANISM: Artificial sequence
<220> FEATURE:
<223> OTHER INFORMATION: Synthetic construct

<400> SEQUENCE: 18
ggaggugcuc gaaagaacuc c                       21

<210> SEQ ID NO 19
<211> LENGTH: 73
<212> TYPE: RNA
<213> ORGANISM: Artificial sequence
<220> FEATURE:
<223> OTHER INFORMATION: Synthetic construct

<400> SEQUENCE: 19
ggguacgagu cuggacuugc aacaaggugc uccaccuacc uaguggaacu ugcugaugag     60
gcucacaaca ggc                                73

-continued

```
<210> SEQ ID NO 20
<211> LENGTH: 79
<212> TYPE: RNA
<213> ORGANISM: Artificial sequence
<220> FEATURE:
<223> OTHER INFORMATION: Synthetic construct

<400> SEQUENCE: 20
ggguacgagu cuggacuugc aaggugcucc guuagcauug cggaacuugc aauauauccu      60
auugaggcuc acaacaggc                                                  79

<210> SEQ ID NO 21
<211> LENGTH: 79
<212> TYPE: RNA
<213> ORGANISM: Artificial sequence
<220> FEATURE:
<223> OTHER INFORMATION: Synthetic construct

<400> SEQUENCE: 21
ggguacgagu cuggacuugc aacggauaca ggugcuccga ucuucggaac uggcguuggc      60
ggugaggcuc acaacaggc                                                  79

<210> SEQ ID NO 22
<211> LENGTH: 79
<212> TYPE: RNA
<213> ORGANISM: Artificial sequence
<220> FEATURE:
<223> OTHER INFORMATION: Synthetic construct

<400> SEQUENCE: 22
ggguacgagu cuggacuugc aauacgaggu gcuccaagga aucgcccugg aacucgacga      60
cgugaggcuc acaacaggc                                                  79

<210> SEQ ID NO 23
<211> LENGTH: 79
<212> TYPE: RNA
<213> ORGANISM: Artificial sequence
<220> FEATURE:
<223> OTHER INFORMATION: Synthetic construct

<400> SEQUENCE: 23
ggguacgagu cuggacuugc aaccuaaugc ggugcuccuc uggaaccauu agcuguugca      60
aaugaggcuc acaacaggc                                                  79

<210> SEQ ID NO 24
<211> LENGTH: 90
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (19)..(58)
<223> OTHER INFORMATION: n is a, c, g, or t

<400> SEQUENCE: 24
ctctcatgtc ggccgttann nnnnnnnnnn nnnnnnnnnn nnnnnnnnnn nnnnnnnncg      60
tccattgtgt ccctatagtg agtcgtatta                                      90

<210> SEQ ID NO 25
<211> LENGTH: 32
<212> TYPE: DNA
<213> ORGANISM: Artificial sequence
<220> FEATURE:
```

```
<223> OTHER INFORMATION: Synthetic construct

<400> SEQUENCE: 25
taatacgact cactataggg acacaatgga cg                                    32

<210> SEQ ID NO 26
<211> LENGTH: 18
<212> TYPE: DNA
<213> ORGANISM: Artificial sequence
<220> FEATURE:
<223> OTHER INFORMATION: Synthetic construct

<400> SEQUENCE: 26
ctctcatgtc ggccgtta                                                    18

<210> SEQ ID NO 27
<211> LENGTH: 30
<212> TYPE: DNA
<213> ORGANISM: Artificial sequence
<220> FEATURE:
<223> OTHER INFORMATION: Synthetic construct

<400> SEQUENCE: 27
taatacgact cactataggg ccacagcgag                                       30

<210> SEQ ID NO 28
<211> LENGTH: 13
<212> TYPE: DNA
<213> ORGANISM: Artificial sequence
<220> FEATURE:
<223> OTHER INFORMATION: Synthetic construct

<400> SEQUENCE: 28
ccgaccacac gcg                                                         13

<210> SEQ ID NO 29
<211> LENGTH: 39
<212> TYPE: DNA
<213> ORGANISM: Artificial sequence
<220> FEATURE:
<223> OTHER INFORMATION: Synthetic construct

<400> SEQUENCE: 29
taatacgact cactataggg tacgagtctg gacttgcaa                             39

<210> SEQ ID NO 30
<211> LENGTH: 17
<212> TYPE: DNA
<213> ORGANISM: Artificial sequence
<220> FEATURE:
<223> OTHER INFORMATION: Synthetic construct; primer

<400> SEQUENCE: 30
gcctgttgtg agcctca                                                     17

<210> SEQ ID NO 31
<211> LENGTH: 50
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (30)..(30)
<223> OTHER INFORMATION: n is a, c, g, or t

<400> SEQUENCE: 31
```

```
tgtcggccgt tacagttccg gtttcccggn tgtaactcgt ccattgtccc                50

<210> SEQ ID NO 32
<211> LENGTH: 36
<212> TYPE: DNA
<213> ORGANISM: Artificial sequence
<220> FEATURE:
<223> OTHER INFORMATION: Synthetic construct; primer

<400> SEQUENCE: 32
taatacgact cactataggg acaatggacg agttac                               36

<210> SEQ ID NO 33
<211> LENGTH: 18
<212> TYPE: DNA
<213> ORGANISM: Artificial sequence
<220> FEATURE:
<223> OTHER INFORMATION: Synthetic construct; primer

<400> SEQUENCE: 33
tgtcggccgt tacagttc                                                   18
```

NUCLEIC ACID CAPABLE OF BINDING TO IMMUNOGLOBULIN G AND USE THEREOF

This application is a U.S. national stage of International Application No. PCT/JP2006/313811 filed Jul. 5, 2006.

This application claims the benefit of U.S. Provisional Application No. 60/749,026, filed Dec. 12, 2005.

TECHNICAL FIELD

The present invention relates to a nucleic acid having binding affinity for immunoglobulin G (IgG). This nucleic acid enables the purification, labeling, immobilization, modification and the like of antibodies for general purposes.

BACKGROUND ART

IgG is a major protein of serum, and plays an important role in recognizing and eliminating foreign matter in the immune system. Making use of this characteristic, IgG is widely studied for applications to therapeutic drugs and diagnostic reagents for various diseases, and test reagents. Such applications include antibody therapies for cancer; therapies based on antibody-dependent cellular cytotoxicity (ADCC) or complement-dependent cytotoxicity (CDC), molecular-targeted drugs that specifically block and starve receptors and the like expressed in cancer cells by means of antibodies, or missile therapy based on cancer cell specific antibody coupled with an anticancer agent, and the like are under development. Amid this situation, an anti-HER2 receptor humanized monoclonal antibody was developed and launched as a therapeutic agent for malignant tumors such as breast cancer (trade name Herceptin). IgG is also used as an essential tool for a range of biochemical experiments, including immunoassay, cell or protein functional analysis, and gene expression screening, on the basis of its property of specific binding to antigens.

IgG has a Y-shaped structure wherein two H chains and two L chains are bound via disulfide bonds (S—S bonds). When decomposed with the proteinase papain, IgG can be divided into an Fc fragment, which consists of a constant region, and a Fab fragment, which comprises an antigen-binding site. IgG involves subclasses; in the case of human IgG, there are four subclasses IgG1, IgG2, IgG3, and IgG4.

Antibodies are purified from serum or hybridoma cell culture supernatant liquid using a column for antibody purification. Generally, for the first-stage purification, Protein A is used as the ligand. Protein A is a protein with a molecular weight of 42 kDa, produced by *Staphylococcus aureus*, and binds strongly to the Fc region of IgG. Protein A is expensive, and there are some cases in which highly pure antibody cannot be obtained because of animal species or subclass, or in which antibodies undergo denaturation under purification conditions with the use of Protein A; there is a demand for a novel separating agent with higher performance than that of Protein A.

Antibodies labeled with fluorescent substances or enzymes are used in a range of experiments, including immunohistochemical experiments, histological staining, ELISA, Western blotting, flowcytometry and the like. For example, in histological staining, by using an antibody having a fluorescent substance such as FITC bound thereto, the tissue localization of desired protein can be examined. In assays such as ELISA and Western blotting, more sensitive assays can be performed by first reacting a primary antibody to the substance to be detected, then reacting a labeled secondary antibody that binds to the primary antibody. For example, in the ECL system from GE Healthcare, an antibody having horseradish peroxidase bound thereto is used as the secondary antibody, and luminol is oxidized and allowed to produce light by the catalytic action of the horseradish peroxidase, whereby the desired substance is detected. However, it takes much labor and time to bind a labeling substance to an antibody by chemical modification, and the antibody sometimes undergoes denaturation; there is a need for the development of a novel technology for antibody labeling. For labeled secondary antibodies, there is a demand for less expensive ones with higher sensitivity.

Development of antibody chips as diagnostic chips for various diseases is ongoing. One problem to be solved is to develop a method for immobilizing an antibody to a substrate, wherein the antigen binding sites of the antibody are arranged at high density in a highly active state on the surface of the substrate. In methods of immobilization utilizing non-specific adsorption and methods of immobilization utilizing amino groups, antibody molecules become arranged randomly so that no sufficient sensitivity can be obtained.

Research and development for antibodies have been rapidly promoted for use as molecular-targeted therapeutic drugs for diseases such as cancer and rheumatism; about 20 kinds of antibody drugs have been brought into practical applications to date, and clinical studies of about 300 kinds of antibody drug candidates are underway worldwide. Initially in the development, mouse monoclonal antibodies were used as antibody drugs; however, because mouse antibodies were recognized as foreign matter by the human immune system and production of human anti-mouse antibodies was induced, no sufficient therapeutic effect could be achieved. Hence, using gene recombination technology, chimeric antibodies wherein the constant regions of mouse antibodies were replaced with the constant regions of human antibodies and humanized antibodies wherein all portions, but the complementarity determinant regions, of mouse antibodies were replaced with human antibodies were developed. A method for preparing a human monoclonal antibody using a human antibody-producing mouse (KM mouse) has also been developed.

One of monoclonal antibody drugs used for antibody therapy is prepared by binding an anticancer agent or toxin to an antibody that specifically recognizes cancer cells, and this is internalized in target cells to kill the target cells. The anticancer agent or toxin needs to be detached from the antibody after internalization. For this reason, a manipulation is made to allow the anticancer agent or toxin to be detached from the antibody after internalization by, for example, adding a protease recognition site to the linker that binds the antibody and the anticancer agent or toxin. For example, gemtuzumab ozogamicin (Mylotarg), which has been developed as a therapeutic drug for acute myelocytic leukemia, comprises a humanized anti-CD33 monoclonal antibody and a calicheamicin derivative bound thereto; when Mylotarg binds to CD33 and becomes internalized in cells, the calicheamicin derivative is liberated to kill the cells. Hence, it is important to design a linker that binds an antibody and an anticancer agent or toxin; to achieve higher pharmacological efficacy, development of novel linkers is ongoing.

In recent years, applications of RNA aptamers to therapeutic drugs, diagnostic reagents, and test reagents have been drawing attention; some RNA aptamers have already been in clinical stage or actual use stage. In December 2004, the world's first RNA aptamer drug, Macugen, was approved as a therapeutic drug for age-related macular degeneration in the US. An RNA aptamer refers to an RNA that binds specifically to a target substance such as a protein, and can be prepared using the SELEX method (Systematic Evolution of Ligands by Exponential Enrichment) (Ellington et al., (1990) Nature, 346, 818-822; Tuerk et al., (1990) Science, 249, 505-510). The SELEX method is a method by which an RNA that binds specifically to a target substance is selected from a pool of about $10^{14}$ RNAs having different nucleotide sequences. The RNA used has a structure wherein a random sequence of about 40 residues is sandwiched by primer sequences. This RNA pool is allowed to associate with a target substance, and only the RNA that has bound to the target substance is recovered using a filter and the like. The RNA recovered is amplified by RT-PCR, and this is used as the template for the next round. By repeating this operation about 10 times, an RNA aptamer that binds specifically to the target substance can be acquired. If the RNA aptamer obtained promotes or inhibits a function of the target substance, this RNA aptamer will be applicable to pharmaceuticals and the like. Actually, RNA aptamers that bind specifically to the human translation initiation factor eIF4A (JP-A-2002-300885, Oguro et al., (2003) RNA 9, 394-407), eIF4E (JP-A-2004-344008, Mochizuki et al., (2005) RNA 11, 77-89), the bone metabolism-related receptor RANK (Receptor Activator of NF-κB, Mori et al., (2004) Nucleic Acids Res. 32, 6120-6128) and the like have been prepared using the SELEX method. An RNA aptamer that binds via an antigen recognition site of anti-DNA autoantibody has also been reported (Kim et al., (2003) Biochemical and Biophysical Research Communication 300, 516-523).

DISCLOSURE OF THE INVENTION

The present invention is directed to providing an aptamer for IgG and a method for utilizing the same, and the like.

The present inventors investigated diligently to solve the problem described above, and, as a result, succeeded in preparing a finely designed aptamer of good quality for IgG, to thereby develop the present invention.

Accordingly, the present invention provides the following.
[1] An aptamer that binds to an Fc region of IgG.
[2] The aptamer of [1] above that binds specifically to an Fc region of human IgG as the Fc region of IgG.
[3] The aptamer according to [1] or [2] above, wherein the total number of nucleotides constituting the aptamer is not more than 40.
[4] The aptamer according to any one of [1] to [3] above, wherein at least one kind of the nucleotides contained in the aptamer is a nucleotide comprising at least two kinds of groups selected from the group consisting of a hydrogen atom, a fluorine atom, a hydroxyl group and an —O-Me group at the 2' position of ribose.
[5] The aptamer of [3] above, comprising the nucleotide sequence shown by GGUG (C/A) (U/T).
[6] The aptamer according to [5] above, wherein the 3rd U in the GGUG (C/A) (U/T) is a nucleotide having the hydroxyl group substituted by a fluorine atom at the 2' position of ribose.
[7] The aptamer according to [6] above, wherein each of the nucleotides in the GGUG (C/A) (U/T) (but excluding the 3rd U), whether identical or different, is a nucleotide comprising a hydroxyl group at the 2' position of ribose, or a nucleotide having the hydroxyl group substituted by a hydrogen atom, a fluorine atom or an —O-Me group at the 2' position of ribose.
[8] The aptamer according to [5] above, wherein the GGUG (C/A) (U/T) is GGUGCU or GGUGAU.
[9] The aptamer according to [5] above, further comprising a nucleotide sequence shown by ANC(N is a nucleotide selected from the group consisting of A, G, C, U and T).

[10] The aptamer according to [9] above, wherein each of the nucleotides in the ANC, whether identical or different, is a nucleotide comprising a hydroxyl group at the 2' position of ribose, or a nucleotide having the hydroxyl group substituted by a hydrogen atom, a fluorine atom or an —O-Me group at the 2' position of ribose.
[11] The aptamer according to [9] above, satisfying one of the requirements (i) to (iii):
  (i) comprising GGA on the 5' side of the GGUG (C/A) (U/T), and comprising UCC on the 3' side of the ANC;
  (ii) comprising $GGN_{X1}A$ on the 5' side of the GGUG (C/A) (U/T), and comprising $UN_{X2}CC$ on the 3' side of the ANC (each of $N_{X1}$ and $N_{X2}$ is a nucleotide selected from the group consisting of A, G, C, U and T); and
  (iii) comprising $GGN_{X3}N_{X4}A$ at the 5' side of the GGUG (C/A) (U/T), and comprising $UN_{X5}N_{X6}CC$ on the 3' side of the ANC (each of $N_{X3}$, $N_{X4}$, $N_{X5}$, and $N_{X6}$ is a nucleotide selected from the group consisting of A, G, C, U and T).
[12] The aptamer according to [11] above, wherein each of the GG contained in the GGA, $GGN_{X1}A$ or $GGN_{X3}N_{X4}A$ and the CC contained in the UCC, $UN_{X2}CC$ or $UN_{X5}N_{X6}CC$ is a nucleotide having the hydroxyl group substituted by a hydrogen atom at the 2' position of ribose.
[13] The aptamer according to [6] above, having a potential secondary structure represented by one of the formulas (I) to (III):

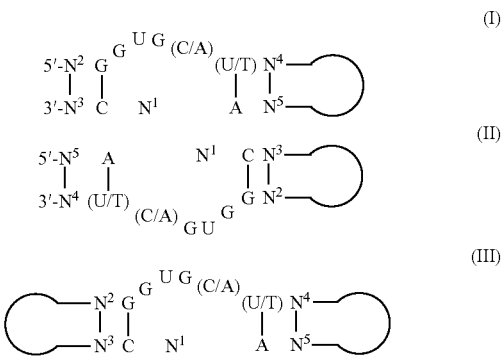

[wherein each of $N^1$, $N^2$, $N^3$, $N^4$, and $N^5$, whether identical or different, is a nucleotide selected from the group consisting of A, G, C, U and T, $N^2$ and $N^3$ are mutually complementary nucleotides, $N^4$ and $N^5$ are mutually complementary nucleotides, each of (i) each nucleotide in the GGUG (C/A) (U/T) (but excluding the 3rd U), (ii) each nucleotide in the $AN^1C$, and (iii) each nucleotide in the $N^2$ to $N^5$, is a nucleotide comprising a hydroxyl group at the 2' position of ribose or a nucleotide having the hydroxyl group substituted by a hydrogen atom, a fluorine atom or an —O-Me group at the 2' position of ribose].

[14] The aptamer according to [11] above, wherein all nucleotides in the loop structure have the hydroxyl group substituted by a hydrogen atom at the 2' position of ribose.

[15] The aptamer according to [13] above, wherein the aptamer having a potential secondary structure represented by any one of (I) to (III) has a potential secondary structure represented by any one of the formulas (I') to (III'):

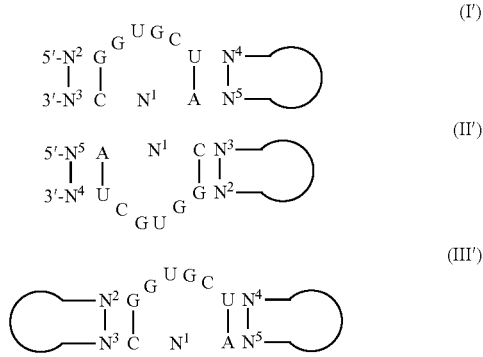

(I')

(II')

(III')

[wherein each of $N^1$, $N^2$, $N^3$, $N^4$, and $N^5$ is as defined in [13] above].

[16] The aptamer according to [3] above, comprising a nucleotide sequence represented by AGGUG (C/A) (U/T)C, wherein the 4th U in the AGGUG (C/A) (U/T)C is a nucleotide having the hydroxyl group substituted by a fluorine atom at the 2' position of ribose, and wherein each nucleotide in the AGGUG (C/A) (U/T)C (but excluding the 4th U), whether identical or different, is a nucleotide comprising a hydroxyl group at the 2' position of ribose or a nucleotide having the hydroxyl group substituted by a hydrogen atom, a fluorine atom or —O-Me at the 2' position of ribose.

[17] The aptamer according to [16] above, further comprising a nucleotide sequence represented by GANCU (N is a nucleotide selected from the group consisting of A, G, C, U and T), wherein each nucleotide in the GANCU, whether identical or different, is a nucleotide comprising a hydroxyl group at the 2' position of ribose or a nucleotide having the hydroxyl group substituted by a hydrogen atom, a fluorine atom or an —O-Me group at the 2' position of ribose.

[18] The aptamer according to [6] above, having a potential secondary structure represented by one of the formulas (Ia) to (IIIa):

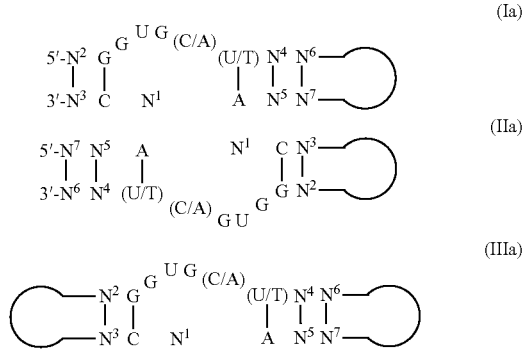

(Ia)

(IIa)

(IIIa)

[wherein each of $N^1$, $N^2$, $N^3$, $N^4$, $N^5$, $N^6$, and $N^7$, whether identical or different, is a nucleotide selected from the group consisting of A, G, C, U and T,
$N^2$ and $N^3$ are mutually complementary nucleotides,
$N^4$ and $N^5$ are mutually complementary nucleotides,
$N^6$ and $N^7$ are mutually complementary nucleotides,
each of (i) each nucleotide in the GGUG (C/A) (U/T) (but excluding the 3rd U), (ii) each nucleotide in the $AN^1C$, and (iii) each nucleotide in the $N^2$ to $N^7$, is a nucleotide comprising a hydroxyl group at the 2' position of ribose or a nucleotide having the hydroxyl group substituted by a hydrogen atom, a fluorine atom or an —O-Me group at the 2' position of ribose].

[19] The aptamer according to [18] above, wherein the aptamer having a potential secondary structure represented by any one of (Ia) to (IIIa) has a potential secondary structure represented by any one of the formulas (Ia') to (IIIa'):

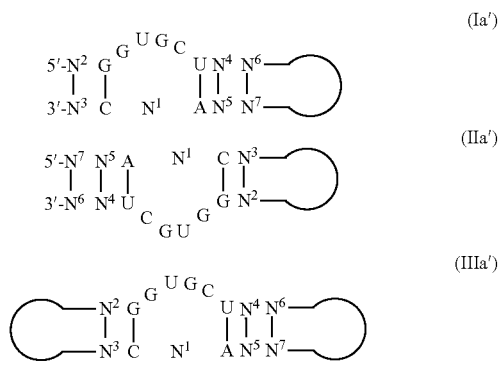

(Ia')

(IIa')

(IIIa')

[wherein each of $N^1$, $N^2$, $N^3$, $N^4$, and $N^5$ is as defined in [18] above].

[20] The aptamer according to [19] above, wherein each of $N^4$ and $N^6$ is a nucleotide having the hydroxyl group substituted by a hydrogen atom at the 2' position, and wherein each of $N^5$ and $N^7$ is a nucleotide comprising a hydroxyl group at the 2' position.

[21] The aptamer according to [19] above, wherein the aptamer having a potential secondary structure represented by any one of (Ia') to (IIIa') has a potential secondary structure represented by any one of the formulas (Ia''') to (IIIa'''):

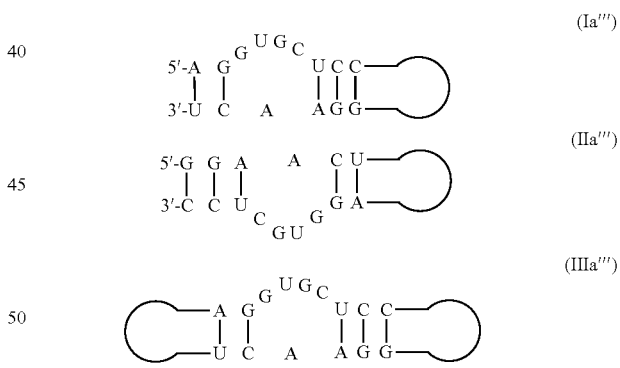

(Ia''')

(IIa''')

(IIIa''')

[22] The aptamer according to [3] above, satisfying one of the requirements (a) to (c):
  (a) an aptamer consisting of a nucleotide sequence shown by any one of SEQ ID NO:1 to 23 (but the uracil may be thymine);
  (b) an aptamer consisting of a nucleotide sequence shown by any one of SEQ ID NO:1 to 23 (but the uracil may be thymine) having one or several nucleotides substituted, deleted, inserted or added;
  (c) a conjugate selected from the group consisting of a conjugate of the (a), a conjugate of the (b), and a conjugate of the (a) and (b).

[23] A complex comprising the aptamer according to any one of [1] to [22] above and a functional substance bound thereto.

[24] The complex according to [23] above, wherein the functional substance is an affinity substance, a labeling substance, an enzyme, a drug, a toxin or a drug delivery vehicle.
[25] A solid phase carrier having the aptamer according to any one of [1] to [22] above or the complex according to [23] or [24] above immobilized thereon.
[26] The solid phase carrier according to [25] above, wherein the solid phase carrier is a substrate, a resin, a plate, a filter, a cartridge, a column or a porous material.
[27] Medical equipment comprising the solid phase carrier according to [25] or [26] above.
[28] The equipment according to [27] above, wherein the medical equipment is equipment for blood purification.
[29] A diagnostic or testing reagent comprising the aptamer according to any one of [1] to [22] above, the complex of [23] or [24] above or the solid phase carrier according to [25] or [26] above.
[30] A pharmaceutical comprising the aptamer according to any one of [1] to [22] above or the complex according to [23] or [24] above.
[31] A method for antibody purification or concentration comprising adsorbing an IgG antibody to the solid phase carrier according to [25] or [26] above, and eluting the adsorbed IgG antibody with an eluent.
[32] The method according to [31] above, wherein the eluent is a neutral solution.
[33] A method for producing a purified antibody, comprising preparing an IgG antibody, and purifying the prepared IgG antibody using the solid phase carrier according to [25] or [26] above.
[34] A method for IgG detection and/or quantitation comprising measuring the presence or absence and/or amount of IgG in a sample using the aptamer according to any one of [1] to [22] above, the complex according to [23] or [24] above or the solid phase carrier according to [25] or [26] above.

BEST MODE FOR CARRYING OUT THE INVENTION

Figure 1:
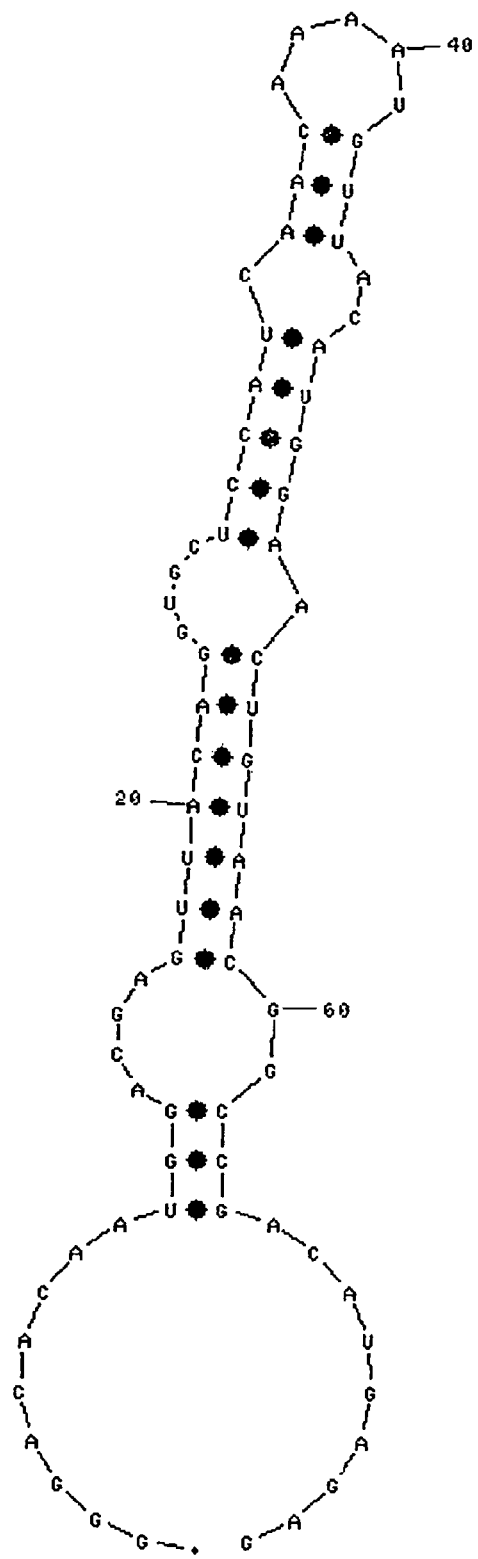
FIG. 1 shows the putative secondary structure of the RNA shown by SEQ ID NO:1.
Figure 2:
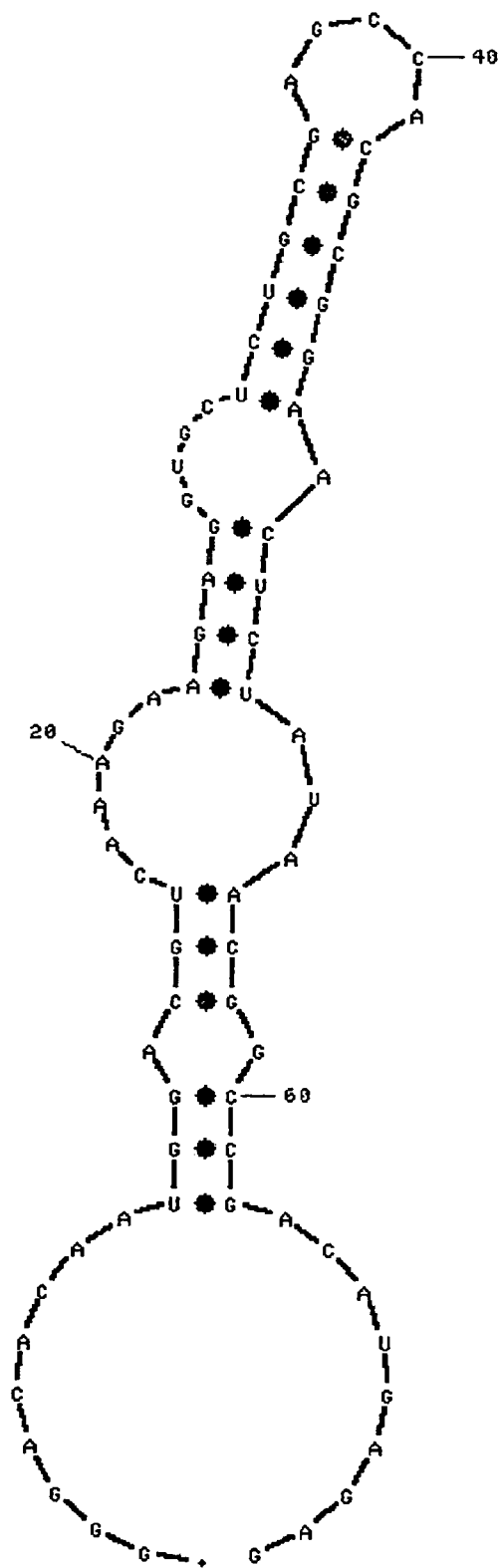
FIG. 2 shows the putative secondary structure of the RNA shown by SEQ ID NO:2.
Figure 3:
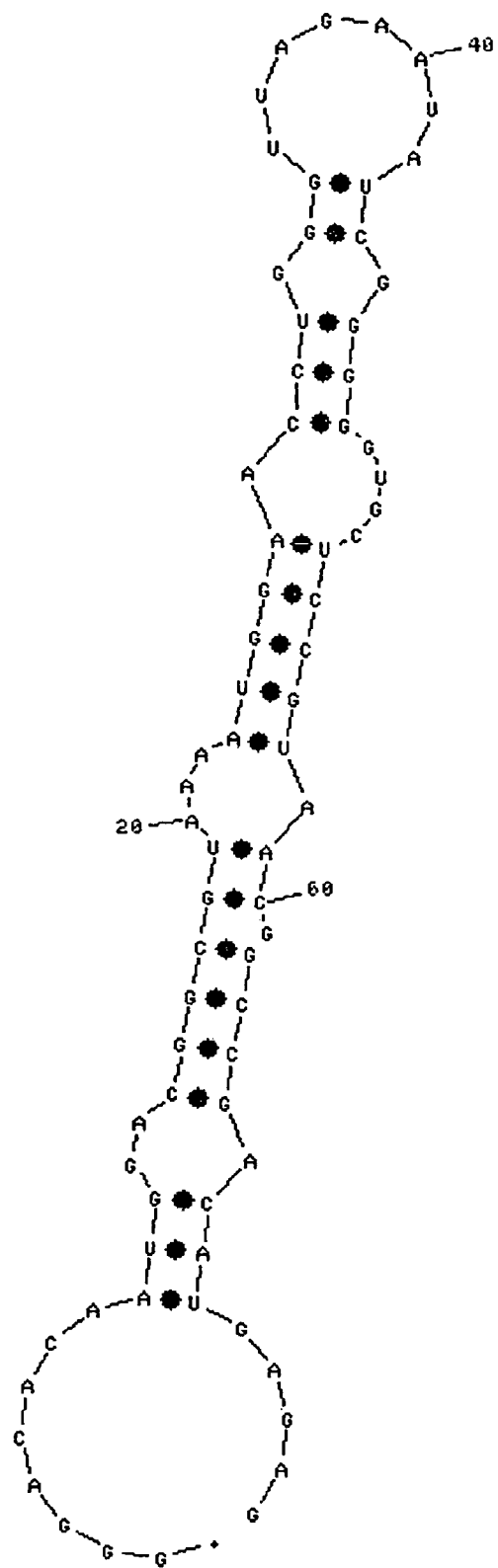
FIG. 3 shows the putative secondary structure of the RNA shown by SEQ ID NO:3.
Figure 4:
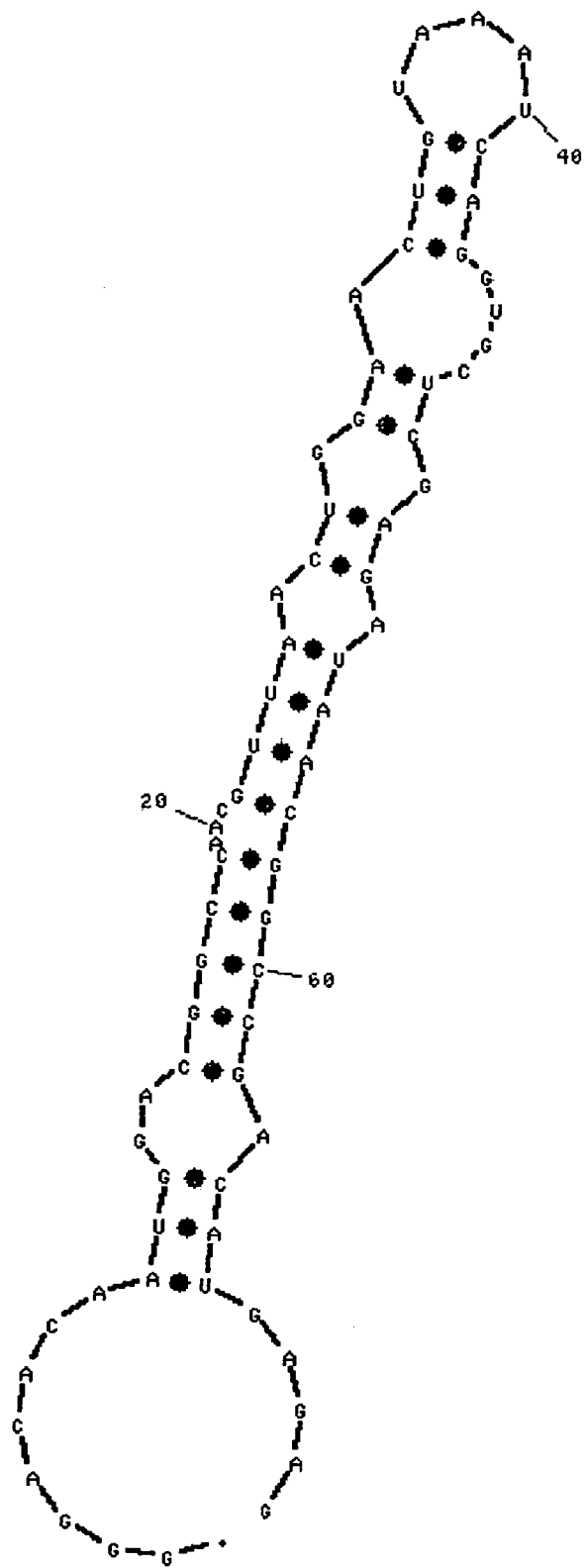
FIG. 4 shows the putative secondary structure of the RNA shown by SEQ ID NO:4.
Figure 5:
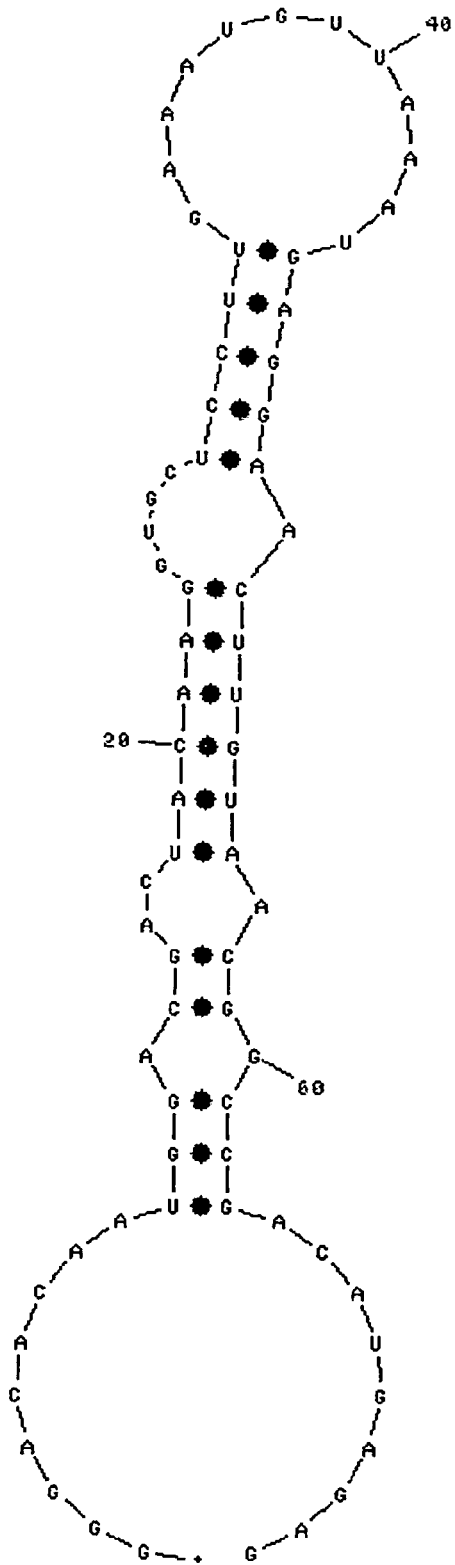
FIG. 5 shows the putative secondary structure of the RNA shown by SEQ ID NO:5.
Figure 6:
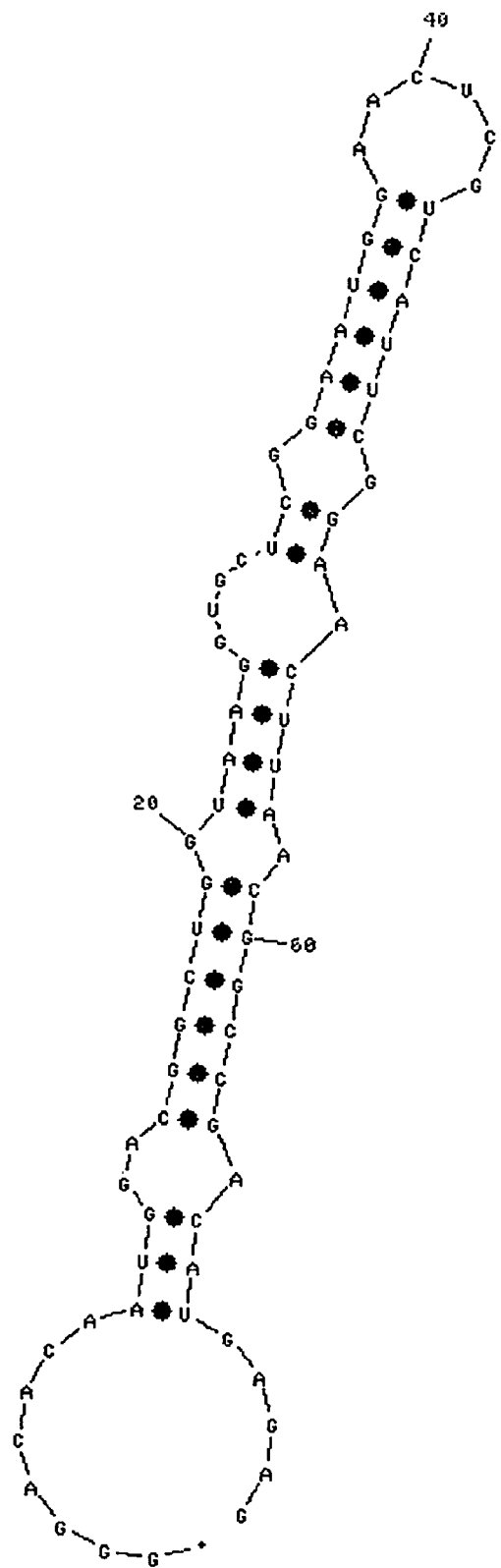
FIG. 6 shows the putative secondary structure of the RNA shown by SEQ ID NO:6.
Figure 7:
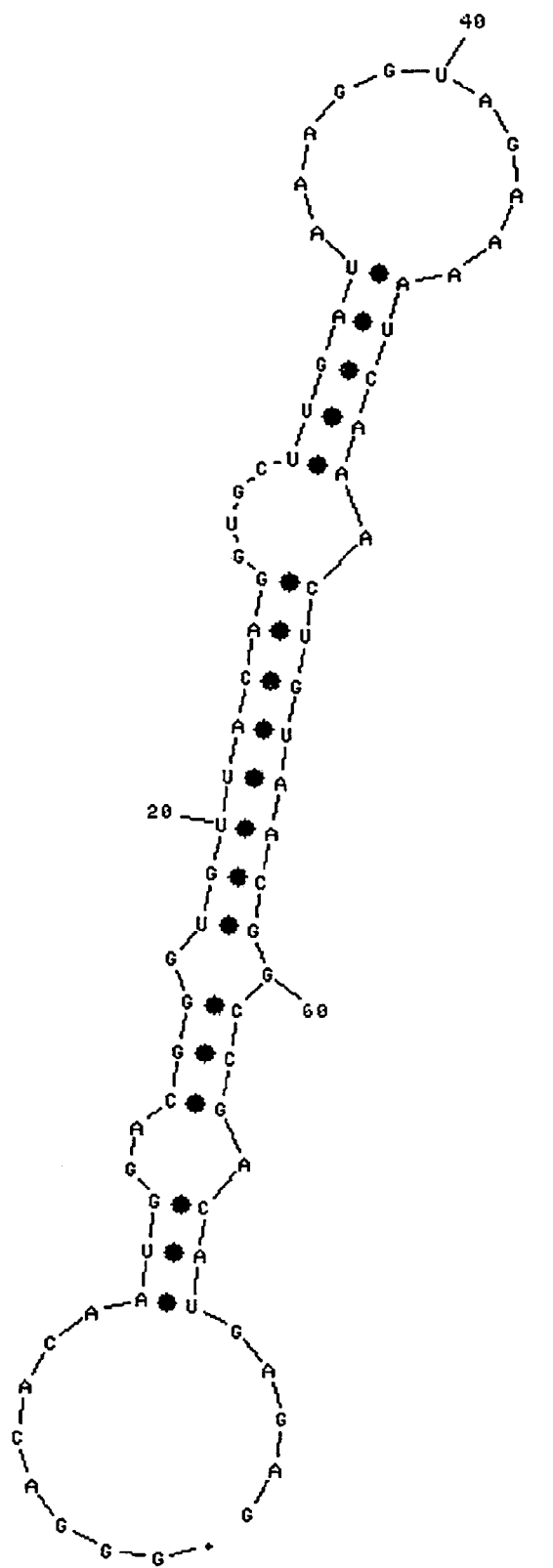
FIG. 7 shows the putative secondary structure of the RNA shown by SEQ ID NO:7.
Figure 8:
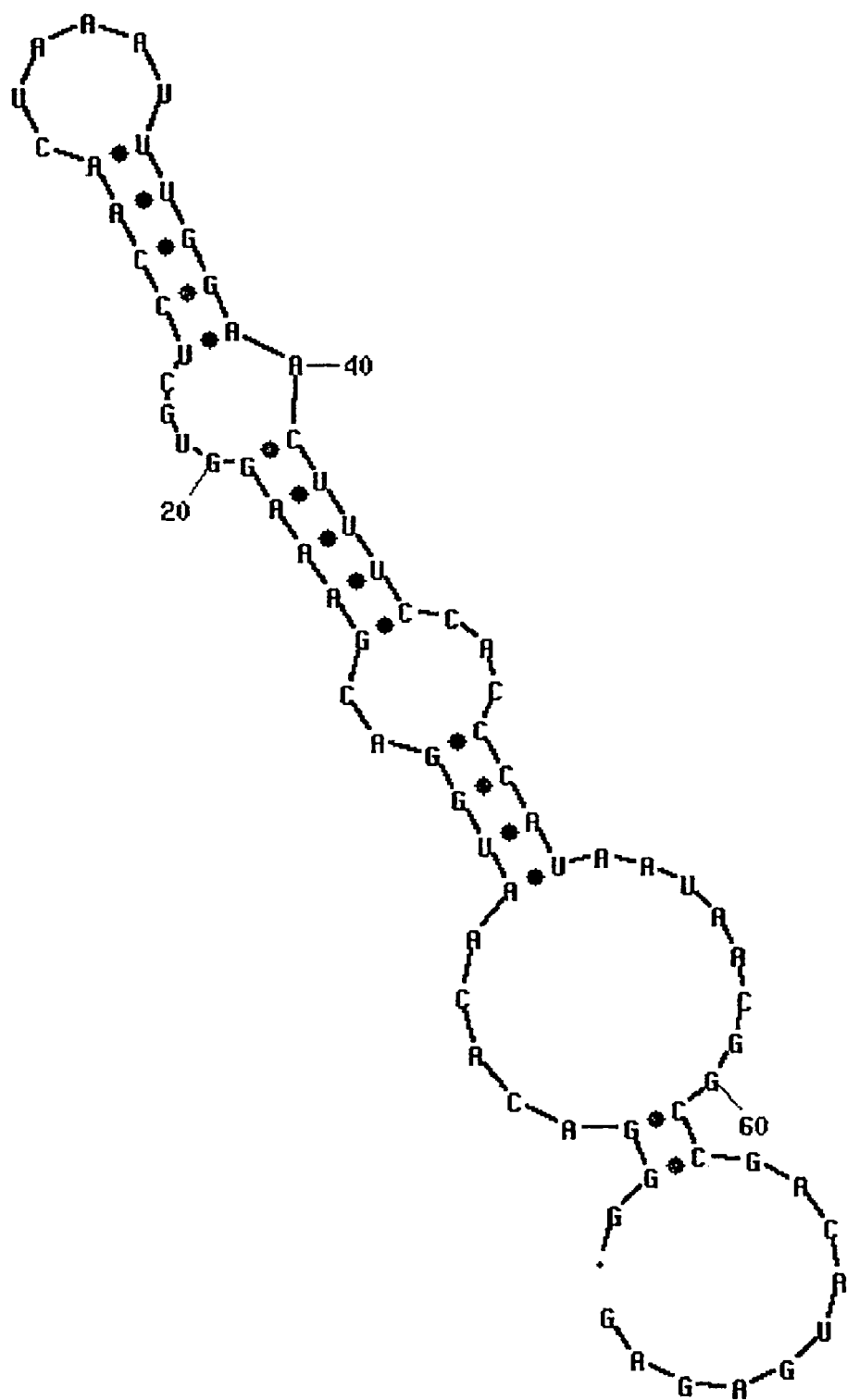
FIG. 8 shows the putative secondary structure of the RNA shown by SEQ ID NO:8.

The present invention provides an aptamer for immunoglobulin G (IgG).

An aptamer refers to a nucleic acid molecule having a binding affinity for a particular target molecule. The aptamer can also have an action to inhibit the activity of a particular target molecule by binding to the particular target molecule. The aptamer of the present invention can be an RNA, a DNA, a modified nucleic acid or a mixture thereof. The aptamer of the present invention can also be in a linear or circular form. The aptamer of the present invention can bind specifically to an Fc region of IgG.

As examples of IgG to which the aptamer of the present invention can bind, human IgG (e.g., IgG1, IgG2, IgG3, IgG4), hamster IgG, and swine IgG can be mentioned.

The aptamer of the present invention can be one capable of binding to an optionally chosen portion of an Fc region of IgG. Fc regions of IgG are known to bind to a receptor protein (FcγR) expressed in immunocompetent cells such as macrophages and neutrophils; the aptamer of the present invention may be one that binds to an Fc region different from the Fc region responsible for the binding to FcγR. Protein A is known to bind to an Fc region of IgG; the aptamer of the present invention may be one that binds to an Fc region different from the Fc region responsible for the binding to Protein A.

The aptamer of the present invention is not particularly limited, as long as it is capable of binding to IgG; for example, as evaluated on the basis of dissociation constant (Kd value), the aptamer of the present invention can be one having a Kd value of not more than about $1\times10^{-6}$ M, preferably not more than about $1\times10^{-7}$ M, more preferably not more than about $1\times10^{-8}$ M. The Kd value can be calculated by, for example, a method based on surface plasmon resonance.

The length of the aptamer of the present invention is not limited, and can usually be about 16 to about 200 nucleotides, and can be, for example, not more than about 100 nucleotides, preferably not more than about 50 nucleotides, more preferably not more than about 40 nucleotides, still more preferably not more than about 30 nucleotides, most preferably not more than about 25 nucleotides. The length of the aptamer of the present invention may be, for example, not less than about 18 nucleotides, preferably not less than about 20 nucleotides. If the total number of nucleotides is smaller, chemical synthesis and mass-production will be easier, and there is a major advantage in terms of cost. It is also thought that chemical modification is easy, stability in the body is high, and toxicity is low.

Each of the nucleotides contained in the aptamer of the present invention, whether identical or different, can be a nucleotide comprising a hydroxyl group at the 2' position of ribose (i.e., an unsubstituted nucleotide) or a nucleotide having the hydroxyl group substituted by an optionally chosen atom or group at the 2' position of ribose. As examples of such an optionally chosen atom or group, a nucleotide substituted by a hydrogen atom, a fluorine atom or an —O— alkyl group (e.g., —O—Me group), an —O— acyl group (e.g., —O—CHO group), or an amino group (e.g., —NH$_2$ group) can be mentioned.

The aptamer of the present invention can be one comprising a nucleotide sequence shown by GGUG (C/A) (U/T). As examples of the GGUG (C/A) (U/T), GGUGCU, GGUGAU, GGUGCT, and GGUGAT can be mentioned; from the viewpoint of being an RNA molecule, GGUGCU and GGUGAU are preferable. If the aptamer of the present invention comprises GGUG (C/A) (U/T), the number of GGUG (C/A) (U/T) contained in the nucleic acid can be one or a plurality (e.g., 2 or 3). Two units of the aptamer of the present invention can bind to one IgG.

The aptamer of the present invention can be one having the 2' position of the ribose of the 3rd U in GGUG (C/A) (U/T) is fluorated (i.e., 2'-F modification) or one having the 2' position of the ribose of the 3rd U has undergone a modification other than fluoration so that the binding affinity of the aptamer of the present invention for IgG can be retained. As examples of such a modification, —O-Me derivatization and amination (NH$_2$) can be mentioned.

The aptamer of the present invention can also be a chemically synthesized one, and can be different from an aptamer having a triphosphate group at the 5' end thereof, synthesized by transcription (e.g., SELEX method), in that it can have a monophosphate group at the 5' end thereof. The aptamer of the present invention can also be one wherein at least one kind (e.g., 1, 2, 3 or 4 kinds) of nucleotide comprises a nucleotide comprising a hydroxyl group, or the above-described optionally chosen atom or group, for example, at least two kinds (e.g., 2, 3 or 4 kinds) of groups selected from the group consisting of a hydrogen atom, a fluorine atom, a hydroxyl group and an —O-Me group, at the 2' position of ribose.

If the aptamer of the present invention comprises a nucleotide sequence shown by GGUG (C/A) (U/T), the aptamer can have a stem structure at both ends thereof. The stem structure can be one that sufficiently stabilizes the bulge structure. For example, as the stem structure, the 5'-end G of GGUG (C/A) (U/T) (1st nucleotide) and one or more nucleotides adjoining thereto on the 5' side, and the 3'-end U/T (6th nucleotide) and one or more nucleotides adjoining thereto on the 3' side, can each form an intramolecular base pair. The number of one or more nucleotides adjoining on the 5' side or 3' side is not limited, as long as it is one or more, and can be, for example, two or more, preferably three or more.

The aptamer of the present invention can also comprise a nucleotide sequence shown by ANC, in addition to the above-described nucleotide sequence shown by GGUG (C/A) (U/T). The N in ANC can be an optionally chosen nucleotide selected from the group consisting of A, G, C, U and T, and is preferably A, G, C or U, more preferably A or G, and most preferably A. If the aptamer of the present invention comprises nucleotide sequences shown by GGUG (C/A) (U/T) and ANC, the GGUG (C/A) (U/T) may be present on the 5' side and the ANC on the 3' side, and the ANC may be present on the 5' side and the GGUG (C/A) (U/T) on the 3' side. The aptamer of the present invention has a structure wherein the 5'-end G in GGUG (C/A) (U/T) is capable of forming an intramolecular base pair with the C in ANC, and/or a structure wherein the 3'-end U/T in GGUG (C/A) (U/T) is capable of forming an intramolecular base pair with the A in ANC. If the aptamer of the present invention can comprise both GGUG (C/A) (U/T) and ANC, the number of units of each of GGUG (C/A) (U/T) and ANC contained in the aptamer can be one or a plurality (e.g., 2 or 3).

The aptamer of the present invention can also be one of the following (i) to (iii):
(i) one comprising GGA on the 5' side of GGUG (C/A) (U/T), and comprising UCC on the 3' side of ANC;
(ii) one comprising GGN$_{X1}$A on the 5' side of GGUG (C/A) (U/T), and comprising UN$_{X2}$CC on the 3' side of ANC (each of $N_{X1}$ and $N_{X2}$ is a nucleotide selected from the group consisting of A, G, C, U and T); or (iii) one comprising $GGN_{X3}N_{X4}A$ (e.g., GGACAG) on the 5' side of GGUG (C/A) (U/T), and comprising $UN_{X5}N_{X6}CC$ on the 3' side of ANC (each of $N_{X3}$, $N_{X4}$, $N_{X5}$, and $N_{X6}$ is a nucleotide selected from the group consisting of A, G, C, U and T). All nucleotides in GGA, $GGN_{X1}A$ or $GGN_{X3}N_{X4}A$, and in UCC, $UN_{X2}CC$ or $UN_{X5}N_{X6}CC$ can be nucleotides comprising a hydroxyl group at the 2' position of ribose (i.e., unsubstituted nucleotides) or nucleotides having the hydroxyl group substituted by a hydrogen atom, a fluorine atom or an —O-Me group at the 2' position of ribose; from the viewpoint of binding affinity, it is also preferable that the nucleotides be nucleotides having the hydroxyl group substituted by a hydrogen atom at the 2' position.

The aptamer of the present invention can also comprise a nucleotide sequence shown by AGGUG (C/A) (U/T)C and/or a nucleotide sequence shown by GANCU (N is a nucleotide selected from the group consisting of A, G, C, U and T). The 4th U in AGGUG (C/A) (U/T)C can be a nucleotide having the hydroxyl group substituted by a fluorine atom at the 2' position or a nucleotide having the 2' position of the ribose of the 4th U has undergone a modification other than fluoration so that the binding affinity of the aptamer of the present invention for IgG can be retained. Each of the nucleotides other than the above-described U, whether identical or different, can be a nucleotide comprising a hydroxyl group at the 2' position of ribose or a nucleotide having the hydroxyl group substituted by a hydrogen atom, a fluorine atom or an —O-Me group at the 2' position of ribose.

In detail, the aptamer of the present invention has a potential secondary structure comprising a bulge structure, two stem structures (S1, S2) present at both ends of the bulge structure and a loop structure. As used herein, "potential secondary structure" refers to a secondary structure capable of occur stably under physiological conditions; for example, whether or not a potential secondary structure is present can be determined using the structure prediction programs described in Examples. All nucleotides in the loop structure can be nucleotides comprising a hydroxyl group at the 2' position of ribose (i.e., unsubstituted nucleotides) or nucleotides having the hydroxyl group substituted by an optionally chosen atom or group (e.g., hydrogen atom, fluorine atom or —O-Me group) at the 2' position of ribose; from the viewpoint of binding affinity, it is also preferable that the nucleotides be nucleotides having the hydroxyl group substituted by a hydrogen atom at the 2' position of ribose.

In more detail, the aptamer of the present invention can have a potential secondary structure represented by one of the formulas (I) to (III):

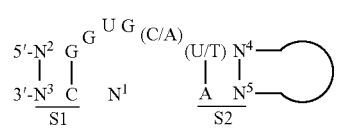

(I)

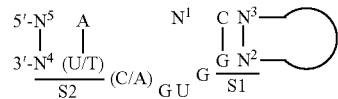

(II)

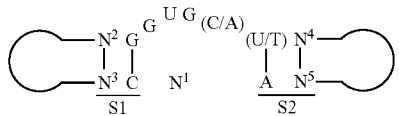

(III)

[wherein each of $N^1$, $N^2$, $N^3$, $N^4$, and $N^5$, whether identical or different, is a nucleotide selected from the group consisting of A, G, C, U and T; $N^2$ and $N^3$ are mutually complementary nucleotides; $N^4$ and $N^5$ are mutually complementary nucleotides]. In the formulas (I) to (III) above, the solid line (bald line) indicates that a nucleotide selected from the group consisting of A, G, C, U and T is joined in an optionally chosen length; the solid line (thin line) indicates that the nucleotide potentially has the ability to bind complementarily (to form a base pair). Each of S1 and S2 represents a stem structure. In the stem structure in each of S1 and S2, the number of nucleotides capable of forming a base pair can be one or more, and may be two or more, three or more or four or more. The curved portion indicates a loop structure. The loop structure can be configured preferably by three or more nucleotides, and is preferably configured by four nucleotides. Preferably, the structure represented by one of the formulas (I) to (III) above can be a structure represented by one of the formulas (I') to (III') above, the formulas (I") to (III") or (I''') to (III''') below.

(I")

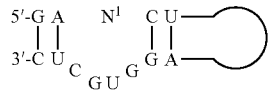

(II")

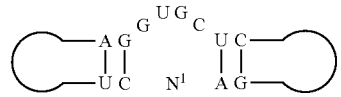

(III")

(I''')

(II''')

(III''')

The 3rd U in GGUG (C/A) (U/T) can be a nucleotide substituted by a fluorine atom at the 2' position of ribose, and each of the other nucleotides (excluding the above-described U) contained in the aptamer of the present invention, whether identical or different, can be a nucleotide comprising a hydroxyl group at the 2' position of ribose or a nucleotide having the hydroxyl group substituted by an optionally chosen atom or group (e.g., hydrogen atom, fluorine atom, or —O-Me group) at the 2' position of ribose.

The aptamer of the present invention can also have a potential secondary structure represented by one of the formulas (Ia) to (IIIa):

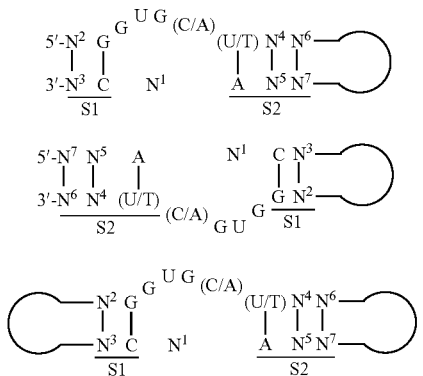

[wherein each of $N^1$, $N^2$, $N^3$, $N^4$, $N^5$, $N^6$, and $N^7$, whether identical or different, is a nucleotide selected from the group consisting of A, G, C, U and T, and wherein $N^2$ and $N^3$ are mutually complementary nucleotides, $N^4$ and $N^5$ are mutually complementary nucleotides, and $N^6$ and $N^7$ are mutually complementary nucleotides]. In the formulas (Ia) to (IIIa) above, the solid line (bald line) indicates that a nucleotide selected from the group consisting of A, G, C, U and T is joined in an optionally chosen length; the solid line (thin line) indicates that the nucleotide potentially has the ability to bind complementarily (to form a base pair). Each of S1 and S2 represents a stem structure. In the stem structure in S1 or S2, the number of nucleotides capable of forming a base pair can be one or more, and may be two or more, three or more or four or more. The curved portion indicates a loop structure. The loop structure can be configured preferably with three or more nucleotides, and is preferably configured by four nucleotides. Preferably, the structure represented by one of the formulas (Ia) to (IIIa) above can be a structure represented by one of the formulas (Ia') to (IIIa') above, the formulas (Ia") to (IIIa") below or the formulas (Ia''') to (IIIa''') above.

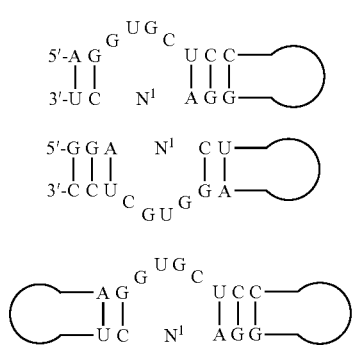

The nucleotide can also be a nucleotide having the 3rd U in GGUG (C/A) (U/T) substituted by a fluorine atom at the 2' position of ribose, and each of the other nucleotides contained in the aptamer of the present invention (excluding the above-described U), whether identical or different, can be a nucleotide comprising a hydroxyl group at the 2' position of ribose or a nucleotide having the hydroxyl group substituted by an optionally chosen atom or group (e.g., hydrogen atom, fluorine atom, —O-Me group) at the 2' position of ribose. From the viewpoint of binding affinity, it is also preferable that each of $N^4$ and $N^6$ be a nucleotide having the hydroxyl group substituted by a hydrogen atom at the 2' position of ribose, and that each of $N^5$ and $N^7$ be a nucleotide comprising a hydroxyl group at the 2' position of ribose.

The aptamer of the present invention can also be (a) an aptamer consisting of a nucleotide sequence shown by one of SEQ ID NO:1 to 23 (but the uracil may be thymine), (b) an aptamer consisting of a nucleotide sequence shown by one of SEQ ID NO:1 to 23 (but the uracil may be thymine) having one or more nucleotides substituted, deleted, inserted or added, or (c) a conjugate selected from the group consisting of a conjugate of a plurality of units of (a) above, a conjugate of a plurality of units of (b) above, and a conjugate of a plurality of units of (a) and (b) above. In (b) above, the number of nucleotides substituted, deleted, inserted or added is not particularly limited, as long as it is several, and the number of nucleotides can be, for example, not more than about 10, preferably not more than about 8, more preferably not more than about 6, still more preferably not more than 5, most preferably 4, 3, 2 or 1. In (c) above, conjugation can be achieved by tandem binding. In the conjugation, a linker may be utilized. As the linker, nucleotide chains (e.g., 1 to about 20 nucleotides) and non-nucleotide chains (e.g., —(CH$_2$)n-linker, —(CH$_2$CH$_2$O)n- linker, hexaethylene glycol linker, TEG linker, peptide-containing linker, —S—S— bond-containing linker, —CONH-bond-containing linker, —OPO$_3$— bond-containing linker) can be mentioned. The plurality as mentioned in the above-described plurality of conjugates is not particularly limited, as long as it is two or more, and the plurality can be, for example, 2 to 4. Each of the nucleotides in (a) to (c) above, whether identical or different, can be a nucleotide comprising a hydroxyl group at the 2' position of ribose or a nucleotide having the hydroxyl group substituted by an optionally chosen group (e.g., hydrogen atom, fluorine atom or —O-Me group) at the 2' position of ribose.

The aptamer of the present invention can also be regenerated and sterilized by heat treatment. As examples of such heat treatments, treatment at 65 to 85° C. for several minutes (e.g., 5 to 15 minutes) can be mentioned.

The aptamer of the present invention may be one wherein a sugar residue (e.g., ribose) of each nucleotide has been modified to increase the IgG bindability, stability, drug deliverability and the like. As examples of the site to be modified in a sugar residue, one having the oxygen atom at the 2'-position, 3'-position and/or 4'-position of the sugar residue replaced with another atom, and the like can be mentioned. As examples of the modification, fluoration, O-alkylation (e.g., O-methylation, O-ethylation), O-arylation, S-alkylation (e.g., S-methylation, S-ethylation), S-arylation, and amination (e.g., —NH$_2$) can be mentioned. Such alterations in the sugar residue can be performed by a method known per se (see, for example, Sproat et al., (1991) Nucle. Acid. Res. 19, 733-738; Cotton et al., (1991) Nucl. Acid. Res. 19, 2629-2635; Hobbs et al., (1973) Biochemistry 12, 5138-5145).

The aptamer of the present invention may also have purine or pyrimidine altered (e.g., chemical substitution) to increase the IgG bindability and the like. As examples of such alterations, 5-position pyrimidine alteration, 8-position purine alteration, alteration with an extracyclic amine, substitution with 4-thiouridine, and substitution with 5-bromo or 5-iodouracil can be mentioned. The phosphate group contained in the aptamer of the present invention may be altered to confer resistance to nuclease and hydrolysis. For example, the P(O)O group may be substituted with P(O)S (thioate), P(S)S (dithioate), P(O)NR$_2$ (amidate), P(O)R, R(O)OR', CO or CH$_2$ (formacetal) or 3'-amine (—NH—CH$_2$—CH$_2$—) [wherein each unit of R or R' is independently H or a substituted or unsubstituted alkyl (e.g., methyl, ethyl)]. The joining group is capable of binding to an adjoining nucleotide via —O—, —N— or —S— linkage. An alteration may also comprise a 3' and 5' alteration like capping. An alteration can be performed by adding polyethylene glycol or another lipid to an end. For such alterations, see, for example, U.S. Pat. Nos. 5,660,985 and 5,756,703.

The aptamer of the present invention can be chemically synthesized according to the disclosures given herein and the technical knowledge in the art. As examples of the aptamer of the present invention, an aptamer comprising a nucleotide sequence shown by GGUG (C/A) (U/T) (and, if required, a nucleotide sequence shown by ANC) can be mentioned; such an aptamer can be designed in sophisticated fashion by utilizing the SELEX method or a modification thereof (for example, Ellington et al., (1990) Nature, 346, 818-822; Tuerk et al., (1990) Science, 249, 505-510). For example, by using a single kind of nucleic acid molecule consisting of a nucleotide sequence shown by the formula:

| Primer sequence (i) | -(N)a-GGUG(C/A) (U/T)-(N)b- | Primer sequence (ii) |

[wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be an optionally chosen number, and can be, for example, 1 to about 100, preferably 1 to about 50, more preferably 1 to about 30, still more preferably 1 to about 20 or 1 to about 10.] or a plurality of kinds of nucleic acid molecules (e.g., a library of nucleic acid molecules with different numbers for "a" or "b"), and primer pairs corresponding to the primer sequences (i) and (ii), respectively, the aptamer of the present invention comprising a nucleotide sequence shown by GGUG (C/A) (U/T) can be designed in sophisticated fashion. The present invention also provides a method for aptamer production that enables such sophisticated design.

The aptamer of the present invention can be useful as, for example, a ligand as a separating agent for antibody purification, a linker that binds an antibody and a labeled substance, an antibody-immobilizing agent, and a linker that binds an antibody and a modified substance. Specifically, the method by which a separating agent for antibody purification is used as a ligand is generally the same as the method for antibody purification using Protein A; however, because of the capability of eluting an antibody with a neutral solution, the former method is advantageous over the method using Protein A, which necessitates antibody elution with an acidic solution, in that antibody denaturation can be prevented. If the aptamer of the present invention is used as a linker for binding an antibody and a labeled substance, high binding affinity such that the aptamer of the present invention does not dissociate from the antibody is necessary. On the other hand, if the aptamer of the present invention is used as a separating agent for antibody purification, the once-adsorbed antibody must be eluted, so that the binding affinity does not always need to be as high as possible. Provided by the present invention is an aptamer having different binding forces and stability profiles for IgG through the use of different sequences, different lengths, and different methods of modification, and having advantages such as inexpensiveness. The aptamer of the present invention also has the various utilities described below.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. As examples of functional substances, proteins, peptides, amino acids, lipids, sugars, monosaccharides, polynucleotides, and nucleotides can be mentioned. As further examples of functional substances, affinity substances, labeling substances, enzymes, drugs, toxins, and drug delivery vehicles can be mentioned.

As examples of affinity substances, biotin, streptavidin, polynucleotides having affinity for target complementary sequence, antibodies, glutathione Sepharose, and histidine can be mentioned.

As examples of labeling substances, fluorescent substances, luminescent substances, and radioisotopes can be mentioned. As examples of fluorescent substances, SYBR Green I, SYBR Green II, SYBR Gold, SYPRO Ruby, SYPRO Orange, SYPRO Tangerine, FITC, FAM, EGFP, ECFP, AttoPhos, SYPRO Red, Cy3, TAMRA, ROX, HEX, Alexa Fluor 532, Alexa Fluor 546, Deep Purple, Pro-Q Diamond, Rhodamine Red, BODIPY 576/589, NED, R-phycoerythrin, RFP, HNPP, Alexa Flour 633, Alexa Flour 635, Alexa Flour 647, Cy5, BODIPY 650/665, DiD, TOTO-3, DDAO phosphate, Ethidium Bromide, SYPRO Rose, Cy7, and fluorescein can be mentioned. As examples of luminescent substances, luminol, luciferin, and lucigenin can be mentioned. As examples of radioisotopes, $^3$H, $^{14}$C, $^{32}$P, $^{35}$S, $^{90}$Y, $^{123}$I, $^{125}$I, and $^{131}$I can be mentioned.

As examples of enzymes, horseradish peroxidase and alkaline phosphatase can be mentioned.

As examples of drugs, anticancer agents can be mentioned. As examples of anticancer agents, those used in missile therapy such as calicheamicin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone and analogues thereof; other cytotoxic antibiotics such as bleomycin and mitomycin; platinum compounds such as cisplatin, carboplatin and oxaliplatin; and other antitumor agents such as pentostatin, miltefosine, estramustine, topotecan, irinotecan and bicalutamide can be mentioned.

As examples of toxins, ricin toxin and liatoxin can be mentioned.

As examples of drug delivery vehicles, liposomes, microspheres, polyethylene glycol, cholesterol, and peptides can be mentioned.

The aptamer of the present invention and/or the complex of the present invention can be used as, for example, a pharmaceutical or a reagent (e.g., diagnostic reagents, test reagents (including experimental reagents)). For example, the pharmaceutical or diagnostic reagent of the present invention is useful in, for example, diseases caused by abnormal IgG and/or overexpression of IgG (e.g., rheumatism, nephritis, Castleman's disease, Wegener's granulomatosis, glomerulosclerosis, glomerular disease, polyarteritis, purpura, erythematosus, graft rejections in organ transplantation), IgG-related diseases, including autoimmune diseases, such as diseases associated with IgG production (e.g., B cell lymphoma), or cancer treatment or diagnosis (e.g., understanding of pathologic condition, monitoring of therapeutic effect). In cancer treatment, by using the complex of the present invention (e.g., a complex prepared by binding the aptamer of the present invention, previously bound to an anticancer agent or toxin, to an antibody drug), it is possible to kill cancer cells.

The reagent of the present invention can be used in the same manner as immunological methods, except that the aptamer of the present invention is used in place of antibody. Therefore, by using the aptamer of the present invention in place of the antibody, it is possible to diagnose the above-described diseases and detect and quantify the IgG described below in the same way as methods such as enzyme immunoassay (EIA) (e.g., direct competitive ELISA, indirect competitive ELISA, sandwich ELISA), radioimmunoassay (RIA), fluorescent immunoassay (FIA), immunochromatography, luminescence immunoassay, spin immunoassay, Western blotting (e.g., used in place of secondary antibody in Western blotting), immunohistochemical staining, and cell sorting. A method using the diagnostic reagent of the present invention is also provided by the present invention; in this case, the solid phase carrier of the present invention can also be used.

The pharmaceutical of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

Preparations suitable for oral administration are a liquid preparation prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

As preparations suitable for parenteral administration (for example, intravenous injection, subcutaneous injection, muscular injection, topical injection, intraperitoneal administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use.

The dosage of the pharmaceutical of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 2.0 g/kg, for example, about 0.0001 to about 0.1 g/kg, preferably about 0.005 to about 0.05 g/kg.

The present invention also provides a solid phase carrier having the aptamer of the present invention and/or the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicon substrates, alumina substrates and the like, and substrates prepared by coating these substrates with a polymer and the like can be mentioned. As examples of the resin, resins for packing in columns for antibody purification chromatography, affinity chromatography with an antibody as the ligand and the like, and resins for purifying or immobilizing an antibody by the batch process can be mentioned, including various concentrations of agarose particles, highly crosslinked agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like, and also including resins prepared by binding various functional groups to these resins.

The aptamer of the present invention and/or the complex of the present invention can be immobilized onto a solid phase carrier by a method known per se. For example, a method comprising introducing an affinity substance (e.g., those described above) or a predetermined functional group into the aptamer of the present invention and/or the complex of the present invention, and then immobilizing the aptamer or complex onto a solid phase carrier via the affinity substance or predetermined functional group can be mentioned. The present invention also provides such methods. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The solid phase carrier of the present invention can be useful in, for example, purifying IgG and detecting and quantifying IgG. The solid phase carrier of the present invention can also be utilized for the treatment for the above-described diseases caused by abnormal IgG or overexpression of IgG. Blood is drawn from a blood vessel of a patient into the solid phase carrier of the present invention (e.g., cartridge) using a liquid supply pump, and a specified amount of IgG is adsorbed and removed, after which the purified blood is returned to the patient. In this case, it is also beneficial to add an anticoagulant to prevent the blood from coagulating. The amount of IgG removed can be adjusted by the amount of blood passed and the volume of the solid phase carrier of the present invention adsorbed. The solid phase carrier of the present invention can be regenerated by washing using a neutral eluent, and sterilizing by heating or ultraviolet irradiation and the like. When the solid phase carrier of the present invention is utilized for purifying the blood, purification can be performed by reference to hemodialytic therapy or a method of blood purification using Prosorba (manufactured by Fresenius) or Immunosorba (manufactured by Fresenius), which are IgG removing agents using Protein A, with respect to details of the method of use and therapeutic effect. Therefore, the present invention also provides medical equipment comprising the solid phase carrier of the present invention, and enabling such blood purification.

The present invention provides a method for antibody purification and/or concentration. The method for purification and/or concentration of the present invention can comprise adsorbing an IgG antibody to the solid phase carrier of the present invention, and eluting the adsorbed IgG antibody with an eluent. The method for purification and/or concentration of the present invention can also be a static method comprising performing purification or concentration with the solid phase carrier of the present invention packed in a container (e.g., flask, test tube, tube), and a dynamic method comprising performing purification or concentration with an IgG-containing solution pumped to the solid phase carrier of the present invention (e.g., column).

Adsorption of IgG antibody to the solid phase carrier of the present invention can be performed by a method known per se. For example, an IgG-containing sample (e.g., blood, plasma, serum, ascites fluid, cell culture supernatant, tissue extract) is introduced to the solid phase carrier of the present invention or to a container or support packed therewith. In the case of a static method, IgG binds to the solid phase carrier of the present invention when the sample is allowed to stand with stirring at room temperature for about 1 to 60 minutes. In the case of a dynamic method, IgG binds to the solid phase carrier of the present invention when the sample is introduced at a flow rate of about 0.1 to 20 mL/minute. The IgG-containing sample may be diluted before being introduced to the solid phase carrier of the present invention. This dilution is preferably performed using a solution containing NaCl and $MgCl_2$. After the IgG has bound to the solid phase carrier of the present invention, the solid phase carrier of the present invention is washed with a washing liquid to remove impurities. The washing liquid is preferably a solution containing NaCl and $MgCl_2$.

Elution of IgG antibody can be performed using a neutral solution. In the conventional method for IgG antibody purification using Protein A, elution needs to be performed with an acidic solution; therefore, the conventional method is disadvantageous in that the antibody is likely to undergo denaturation. On the other hand, the aptamer of the present invention enables elution to be performed with a neutral solution; therefore, the aptamer of the present invention is advantageous over the conventional method in that antibody denaturation can be prevented.

The neutral eluent is not particularly limited, and can have a pH of, for example, about 6 to about 9, preferably about 6.5 to about 8.5, more preferably about 7 to about 8. The neutral solution can comprise a potassium salt (e.g., potassium chloride (KCl), potassium acetate, potassium formate, potassium dihydrogen phosphate, dipotassium hydrogen phosphate, tripotassium phosphate, potassium nitrate, potassium sulfate, potassium sulfite, potassium perchlorate, potassium citrate, potassium malate, potassium oxalate, potassium cyanide), a magnesium salt (e.g., magnesium chloride, magnesium acetate, magnesium formate, magnesium sulfate, magnesium oxalate), a calcium salt (e.g., calcium chloride, calcium acetate, calcium formate, calcium sulfate, calcium oxalate), an ammonium salt (e.g., ammonium chloride, ammonium acetate, ammonium formate, ammonium phosphate, ammonium nitrate, ammonium sulfate, ammonium sulfite, ammonium perchlorate, ammonium citrate, ammonium cyanide, ammonium oxalate), a chelating agent (e.g., ethylenediaminetetraacetic acid (EDTA), a citrate such as sodium citrate, a malate such as sodium malate, an oxalate such as sodium oxalate, ethylenediamine, acetylacetosodium, EGTA), a denaturant or a surfactant (guanidine, SDS, Tween 20, NP-40, Triton X-100), and from the viewpoint of cost, one containing KCl is preferable. The concentration of the KCl solution is 100 to 1000 mM, preferably 200 to 800 mM, more preferably 300 to 600 mM. The concentration of the EDTA solution is 1 to 100 mM, preferably 5 to 50 mM, more preferably 10 to 20 mM.

The method for purification of the present invention can further comprise washing the solid phase carrier after adsorbing the IgG antibody. As examples of the washing liquid, solutions containing urea, a strong base (e.g., sodium hydroxide, potassium hydroxide), a weak base (e.g., ammonia), a strong acid (e.g., hydrochloric acid, nitric acid, sulfuric acid, trifluoroacetic acid), or a weak acid (e.g., acetic acid, formic acid) can be mentioned. The urea can be, for example, 1 to 10 M. The strong base and the weak base are preferably 0.01 to 10 N, more preferably 0.01 to 1 N, still more preferably 0.01 to 0.1 N. The strong acid and the weak base are preferably 0.01 to 10 N, more preferably 0.01 to 1 N, still more preferably 0.01 to 0.1 N.

The method for purification of the present invention can further comprise heat treatment of the solid phase carrier. This step enables the regeneration and sterilization of the solid phase carrier. As examples of such heat treatment, a treatment at about 50 to about 100° C., preferably about 60 to about 90° C., more preferably about 65 to about 85° C., for several minutes, for example, 1 to 30 minutes, preferably 1 to 20 minutes, more preferably 5 to 15 minutes, can be mentioned. The heat treatment can be performed in urea (e.g., 1 to 10 M).

The present invention also provides a method for producing a purified antibody. The method for production of the present invention can comprise preparing an IgG antibody, and purifying the prepared IgG antibody by means of the aptamer and complex of the present invention (e.g., by using the solid phase carrier of the present invention).

The antibody prepared in the method for production of the present invention can be IgG. The antibody can also be a polyclonal antibody or a monoclonal antibody. A polyclonal antibody or a monoclonal antibody can be prepared by a method known per se. The antibody can further be a humanized antibody or a human antibody, and a humanized antibody or a human antibody is preferable. A humanized antibody can be prepared by reference to, for example, JP-T-HEI-4-506458, JP-A-SHO-62-296890 and the like; a human antibody can be prepared by reference to, for example, "Nature Genetics, Vol. 15, p. 146-156, 1997", "Nature Genetics, Vol. 7, p. 13-21, 1994", JP-T-HEI-4-504365, International Patent Application Publication WO94/25585, "Nikkei Science, June issue, pp. 40 to 50, 1995", "Nature, Vol. 368, p. 856-859, 1994", JP-T-HEI-6-500233 and the like.

Next, the prepared antibody can be purified using an aptamer. The details of the purification can be the same as those for the method for purification of the present invention.

The present invention also provides a method for detection and/or quantitation of IgG. The method for detection and/or quantitation of the present invention can comprise measuring IgG by means of the aptamer of the present invention (e.g., by using the complex of the present invention and/or solid phase carrier). In this method, as described with respect to the diagnostic reagent of the present invention, detection and/or quantitation can be performed in the same manner as immunological methods except that the aptamer of the present invention is used in place of the antibody.

The present invention also provides a method for antibody modification. The method for modification of the present invention can comprise binding a functional substance to an antibody via the aptamer of the present invention. The present invention also provides a modified antibody prepared by such a method of modification.

The disclosures in all publications mentioned herein, including patents and patent application specifications, are incorporated by reference herein in the present invention to the extent that all of them have been given expressly.

The present invention is hereinafter described in more detail by means of the following Examples, which, however, never limit the scope of the invention.

EXAMPLES

Example 1

Preparation of Nucleic Acid that Binds Specifically to IgG

A nucleic acid that binds specifically to IgG was prepared using the SELEX method. SELEX was performed by the method of Ellington et al. (Ellington and Szostak, Nature 346, 818-822, 1990) and the method of Tuerk et al. (Tuerk and Gold, Science 249, 505-510, 1990) with improvements. Used as the target substance was a chimera (IgG1-Fc, manufactured by R&D Systems) of an Fc region of human IgG1 with a histidine tag (Pro100 to Lys330) and RANK (Receptor activator of NF-κB). This chimera had been expressed using mouse myeloma cells. The RNA used in the first round was obtained by transcribing a DNA obtained by chemical synthesis, using the DuraScribe™ T7 Transcription Kit (manufactured by Epicentre). The RNA obtained by this method has been fluorated at the 2'-position of the ribose of each pyrimidine base-containing nucleotide. Used as the DNA template was a DNA 90 residue long having a primer sequence on each side of a 40-residue random sequence. The DNA template and the primers were prepared by chemical synthesis (manufactured by Operon). The sequence of the DNA template and the sequences of the primers are shown below.

DNA template:
(SEQ ID NO: 24)
5'-ctctcatgtcggccgtta-40N-cgtccattgtgtccctatagtgag
tcgtatta-3'

Primer A:
(SEQ ID NO: 25)
5'-taatacgactcactatagggacacaatggacg-3'

Primer B:
(SEQ ID NO: 26)
5'-ctctcatgtcggccgtta-3'

Primer A comprises a promoter sequence of T7 RNA polymerase. The variation of the RNA pool used in the first round was theoretically $10^{14}$.

The target substance IgG1-Fc was adsorbed and immobilized onto Ni-NTA affinity resin (manufactured by Qiagen) or BD Talon™ affinity resin (manufactured by BD Biosciences). The RNA pool was added thereto, and the resin was kept at room temperature for 30 minutes, after which the RNA not bound to the IgG1-Fc was washed away with a solution A. The solution A here was a mixed solution of 145 mM sodium chloride, 5.4 mM potassium chloride, 1.8 mM calcium chloride, 0.8 mM magnesium chloride, and 20 mM pH 7.6 Tris. The RNA bound to the IgG1-Fc was recovered by the addition of an eluent, and amplified by RT-PCR, after which it was transcribed using the DuraScribe™ T7 Transcription Kit, and used in the next round. Used as the eluent was a solution A supplemented with 250 mM imidazole. After completion of 7 rounds or 10 rounds, the PCR product was cloned into the pGEM-T Easy vector (manufactured by Promega), and the *Escherichia coli* strain DH5α (manufactured by Toyobo) was transformed by the vector. After the plasmid was extracted from a single colony, nucleotide sequences were determined using a DNA sequencer (ABI PRISM 3100, manufactured by ABI). Of the 48 clones, 10 clones had the sequence shown by SEQ ID NO:1. Of the 48 clones, 2, 7, 14, 2, 5, 4, and 4 clones had the sequences shown by SEQ ID NO:2, 3, 4, 5, 6, 7, and 8, respectively.

The secondary structures of the RNAs shown by SEQ ID NO:1 to 8 were estimated using the MFOLD program (M. Zuker, Mfold web server for nucleic acid folding and hybridization prediction. Nucleic Acids Res. 31 (13), 3406-15, (2003)). The structures are shown in FIGS. 1 to 8. As shown in the figures, these RNAs comprised the shared sequence GGUGCU, and this shared sequence had formed a bulge.

Changing the primer set, SELEX was performed again as described above. The primer sequences are shown below.

Primer C:
5'-taatacgactcactatagggccacagcgag-3' (SEQ ID NO: 27)

Primer D:
5'-ccgaccacacgcg-3'  (SEQ ID NO: 28)

Figure 9:
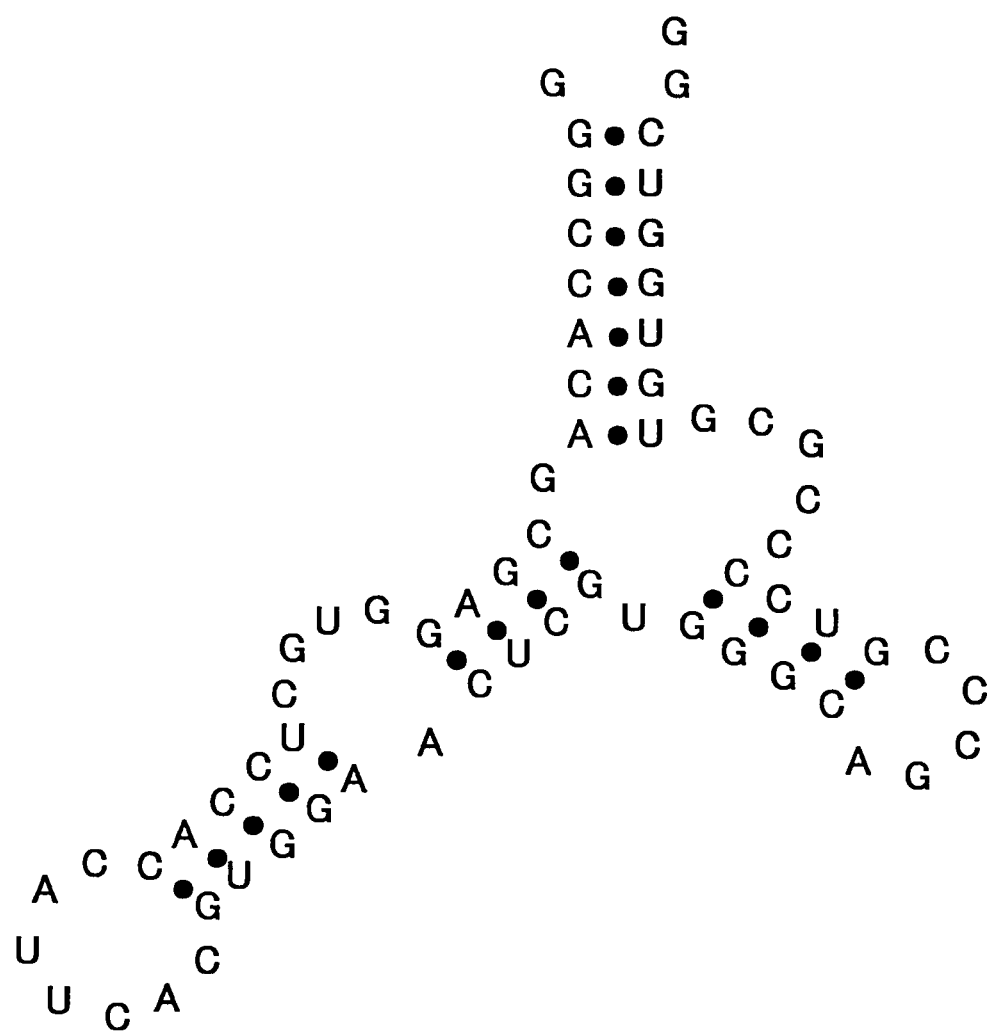
FIG. 9 shows the putative secondary structure of the RNA shown by SEQ ID NO:9.
Figure 10:
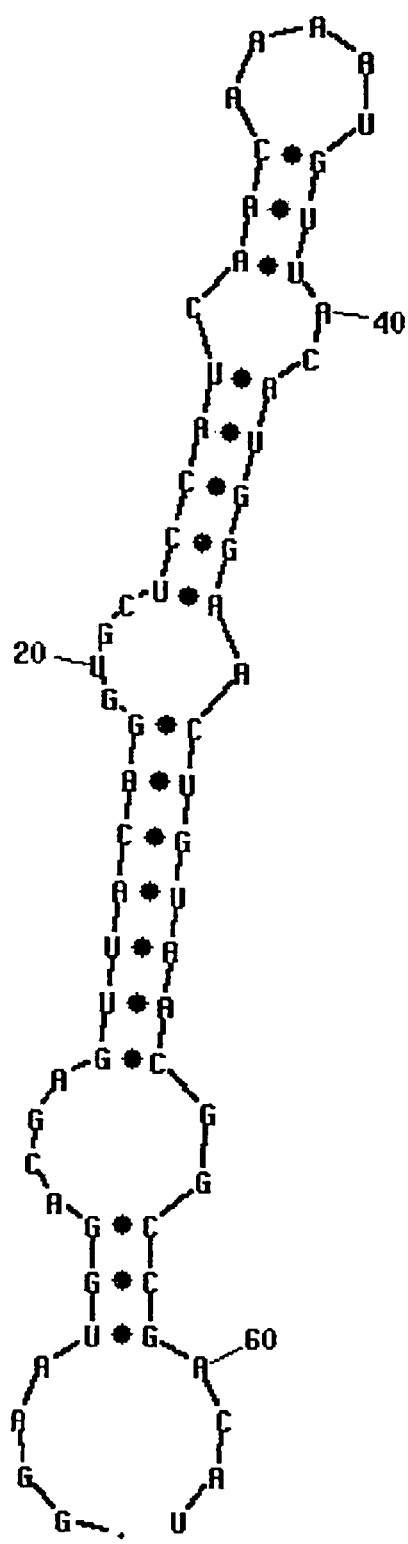
FIG. 10 shows the putative secondary structure of the RNA shown by SEQ ID NO:10.
Figure 11:
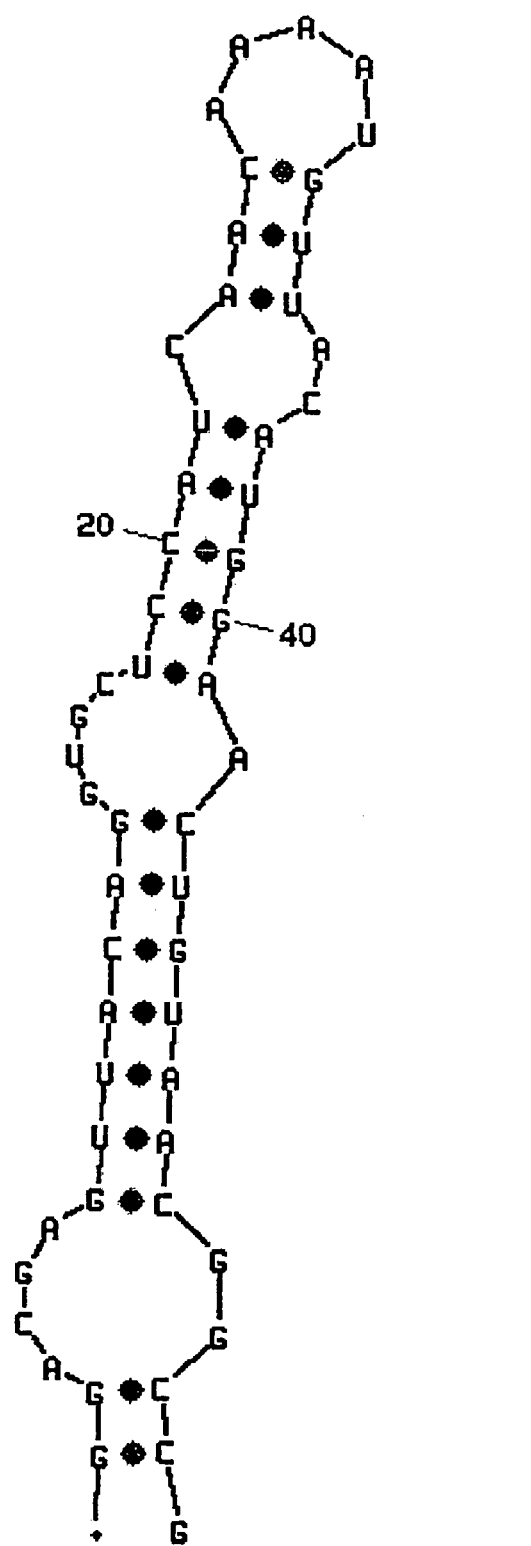
FIG. 11 shows the putative secondary structure of the RNA shown by SEQ ID NO:11.
Figure 12:
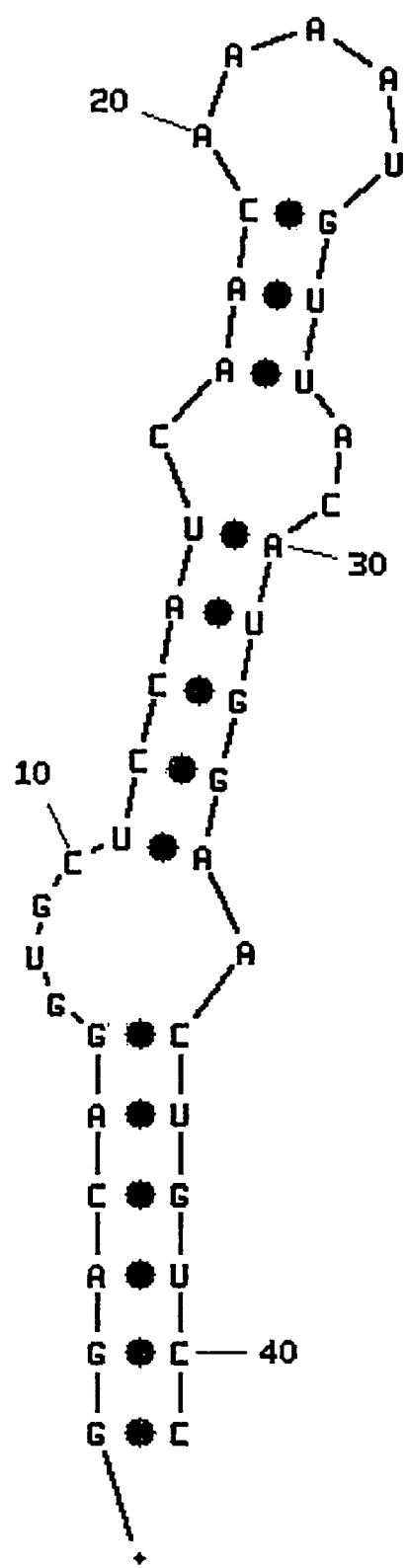
FIG. 12 shows the putative secondary structure of the RNA shown by SEQ ID NO:12.
Figure 13:
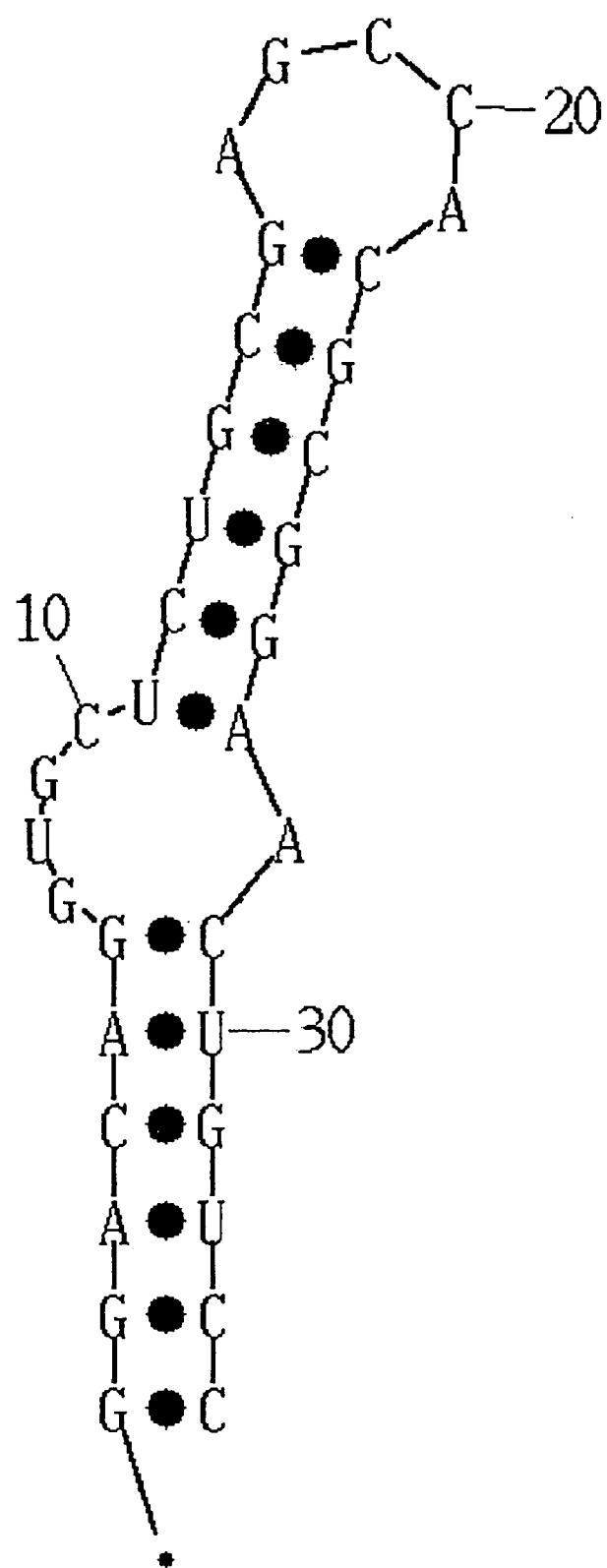
FIG. 13 shows the putative secondary structure of the RNA shown by SEQ ID NO:13.
Figure 14:
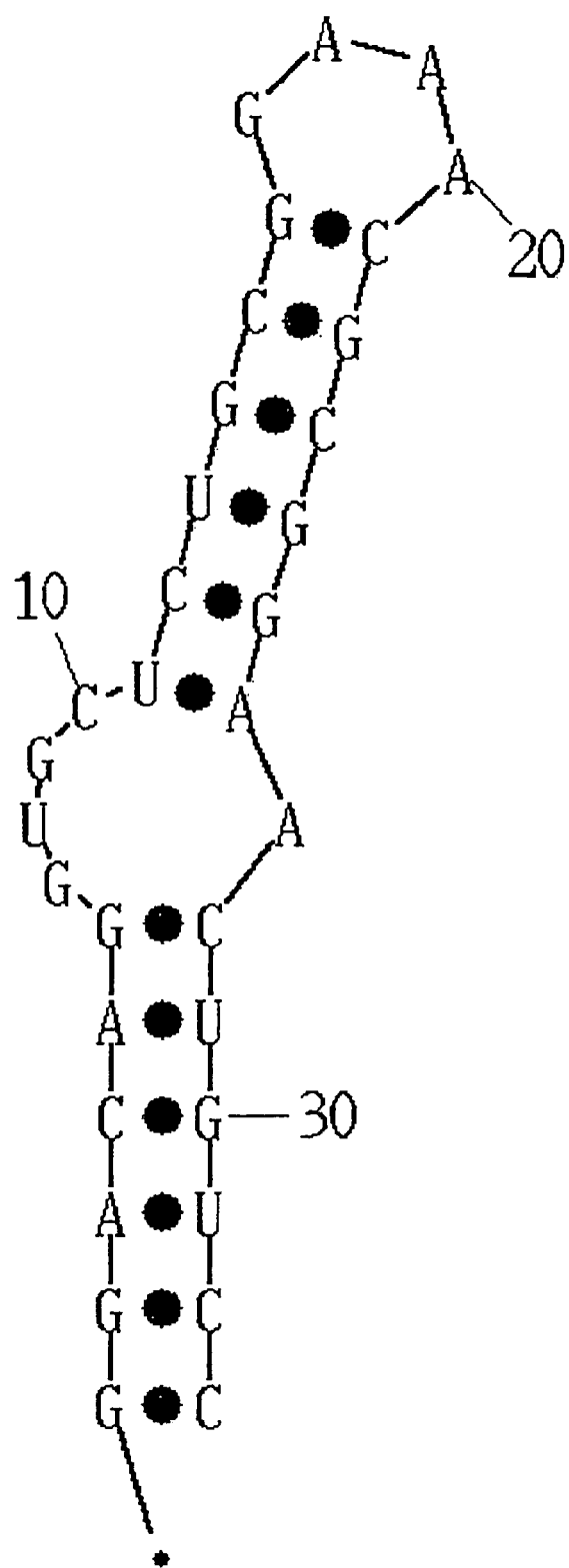
FIG. 14 shows the putative secondary structure of the RNA shown by SEQ ID NO:14.
Figure 15:
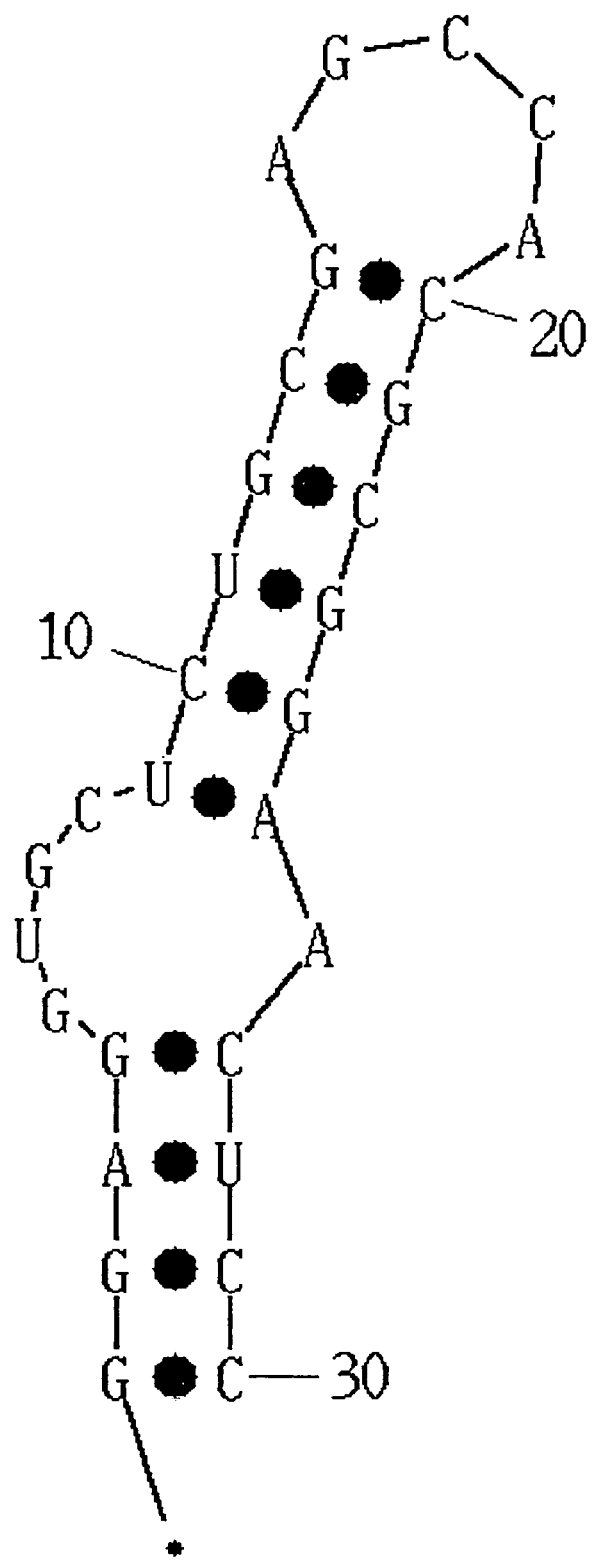
FIG. 15 shows the putative secondary structure of the RNA shown by SEQ ID NO:15.
Figure 16:
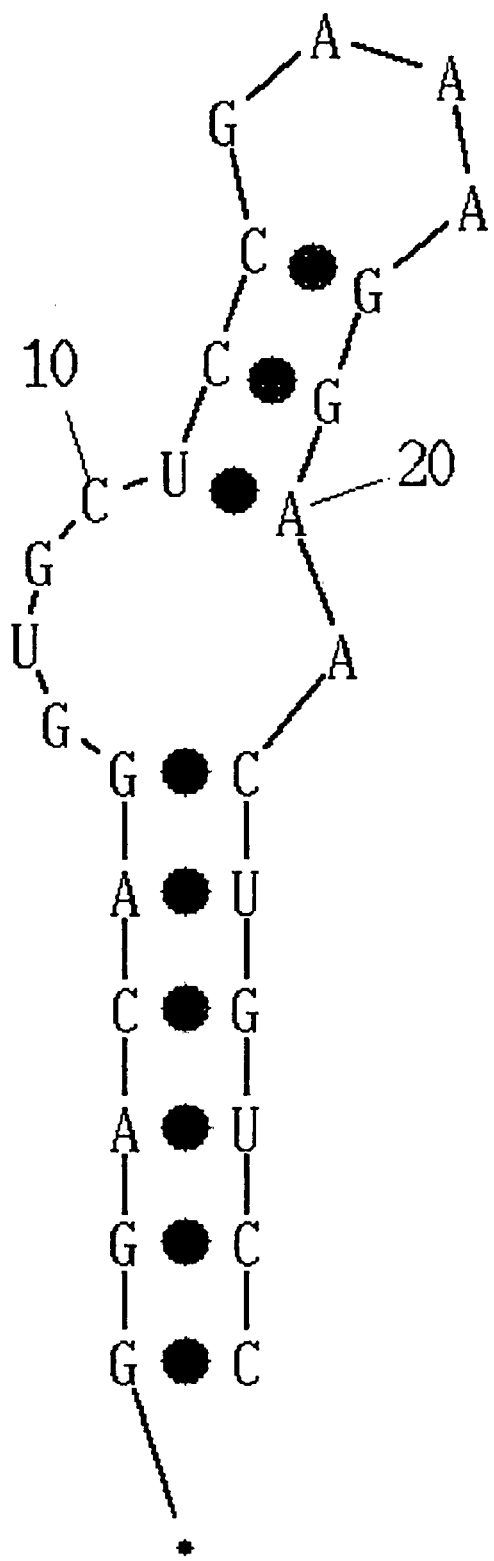
FIG. 16 shows the putative secondary structure of the RNA shown by SEQ ID NO:16.
Figure 17:
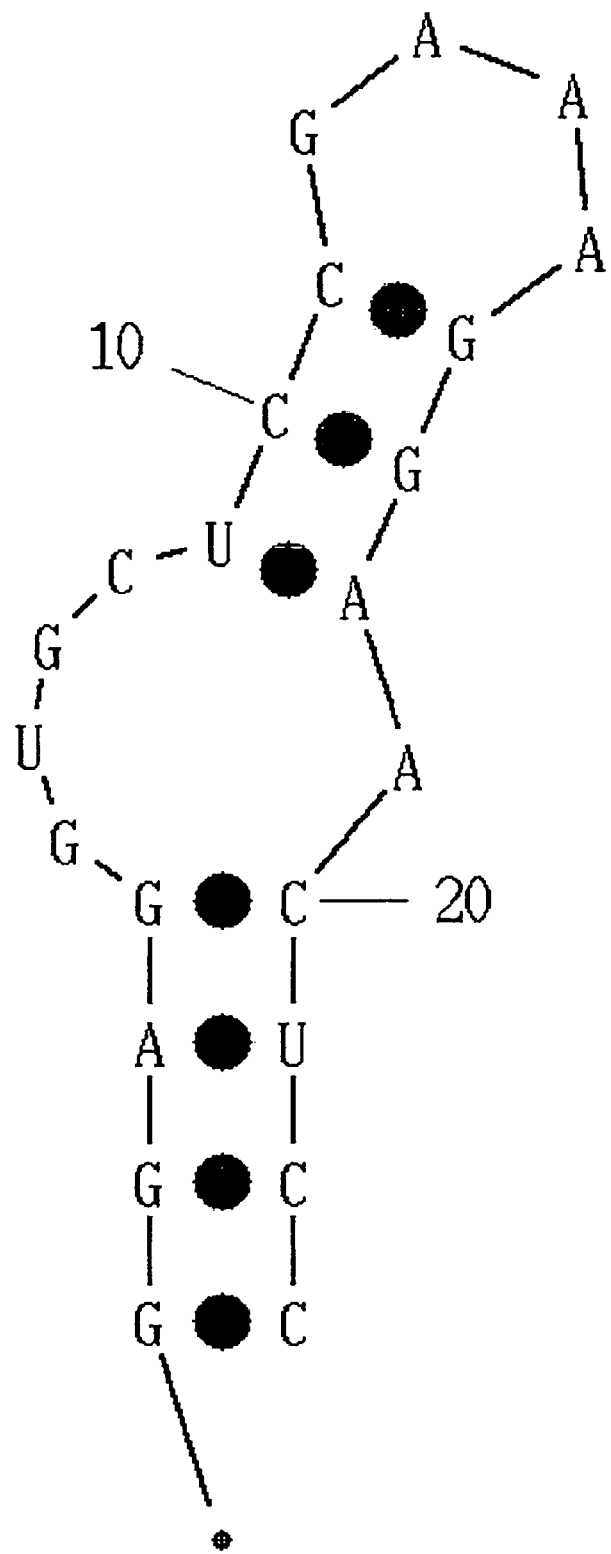
FIG. 17 shows the putative secondary structure of the RNA shown by SEQ ID NO:17.
Figure 18:
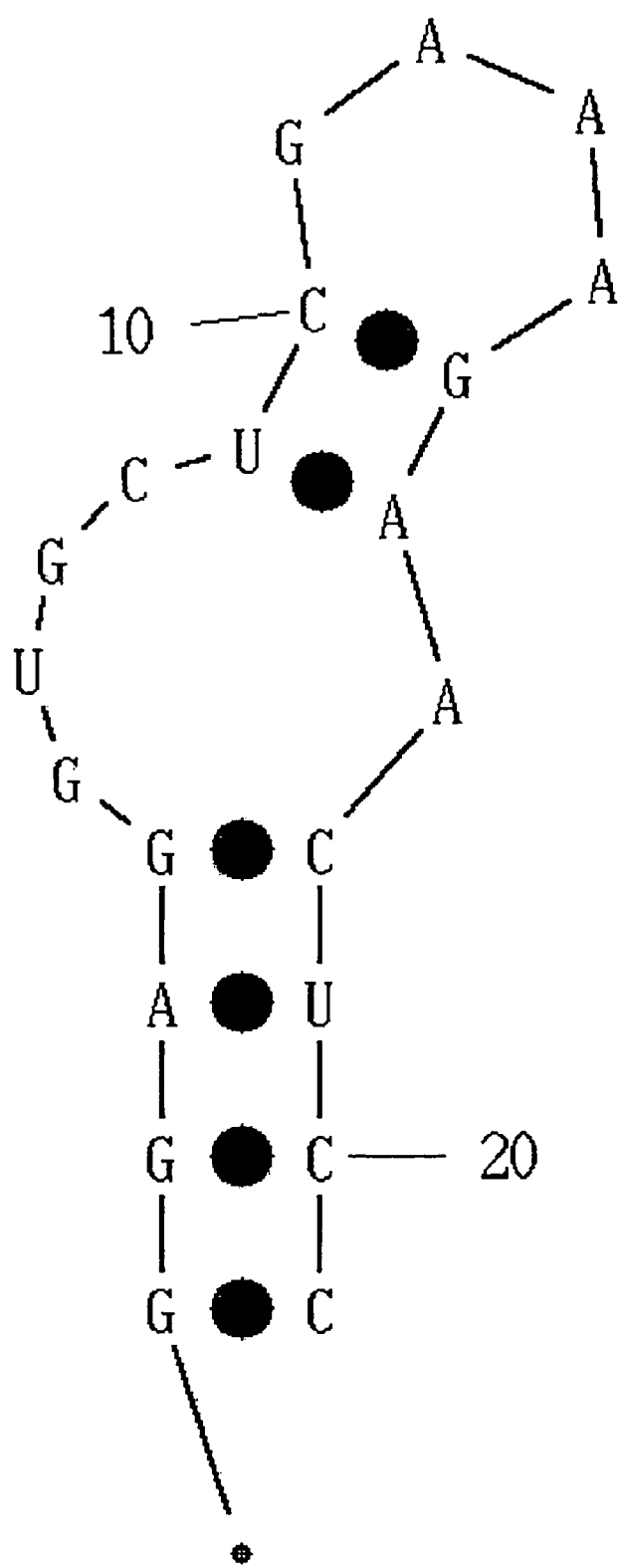
FIG. 18 shows the putative secondary structure of the RNA shown by SEQ ID NO:18.

After completion of 8 rounds, the RNA shown by SEQ ID NO:9 was present in 1 of the 48 clones sequenced. This RNA bound specifically to human IgG1, and had the GGUGCU sequence therein. However, when the secondary structure of this RNA was estimated using the MFOLD program, the bulge structure of GGUGCU was not present therein. Hence, the secondary structure of the RNA shown by SEQ ID NO:9 was estimated using the vsfold4 program; the bulge structure of GGUGCU appeared (FIG. 9). On the other hand, none of the other 47 clones bound to IgG1.

Next, SELEX was performed with an Fc fragment of IgG (IgG-Fc) immobilized by amino coupling. 100 μg of human IgG-Fc (manufactured by Athens Research & Technology) was immobilized onto 30 μL of NHS-activated Sepharose beads (manufactured by Amersham Bioscience). Since the IgG-Fc solution purchased comprised a Tris buffer solution, coupling was performed after the Tris buffer solution was replaced with 20 mM HEPES buffer solution (manufactured by Sigma). Coupling was performed as directed in the kit specifications. The amount immobilized was confirmed by examining the IgG-Fc solution before immobilization and the supernatant liquid just after immobilization by SDS-PAGE. No IgG-Fc band was detected in the supernatant liquid; it is thought that almost all of the IgG-Fc used underwent coupling. The RNA used was found to be fluorated at the 2'-position of the ribose of each pyrimidine base-containing nucleotide as described above. Used as the DNA template for preparing an initial pool of RNA was one wherein a 40-residue random sequence was sandwiched between the primer sequences shown below.

```
Primer E:
                                     (SEQ ID NO: 29)
5'-taatacgactcactatagggtacgagtctggacttgcaa-3'

Primer F:
                                     (SEQ ID NO: 30)
5'-gcctgttgtgagcctca-3'
```

Figure 19:
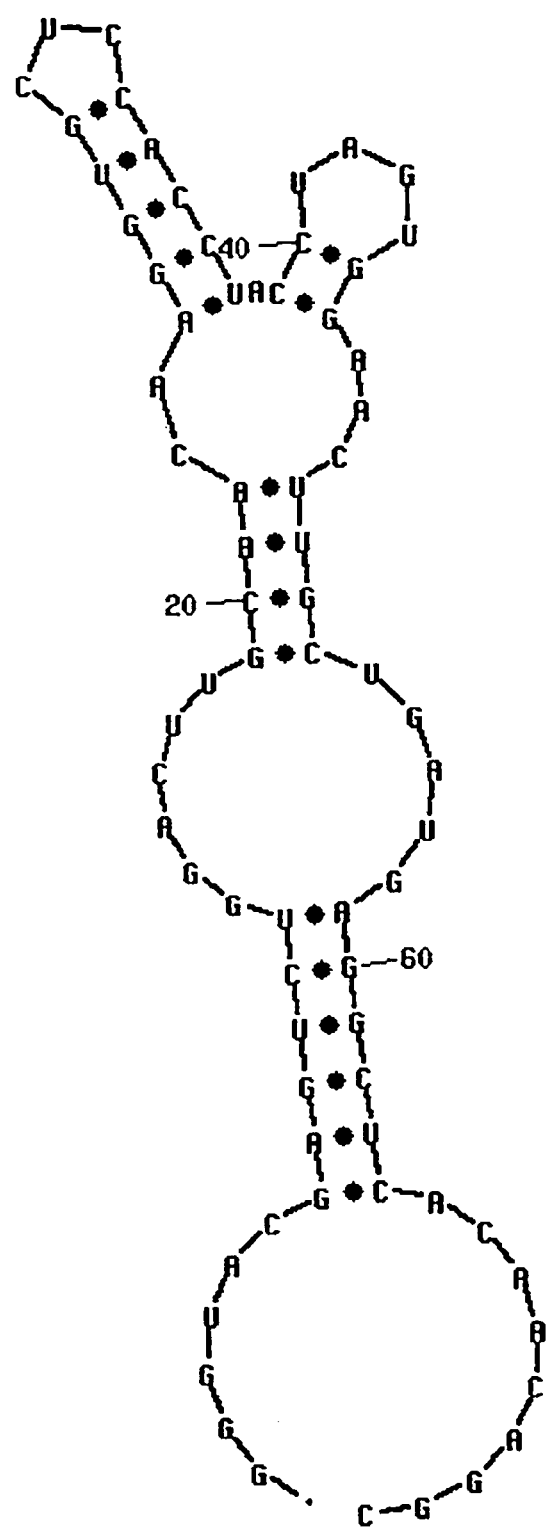
FIG. 19 shows the putative secondary structure of the RNA shown by SEQ ID NO:19.
Figure 20:
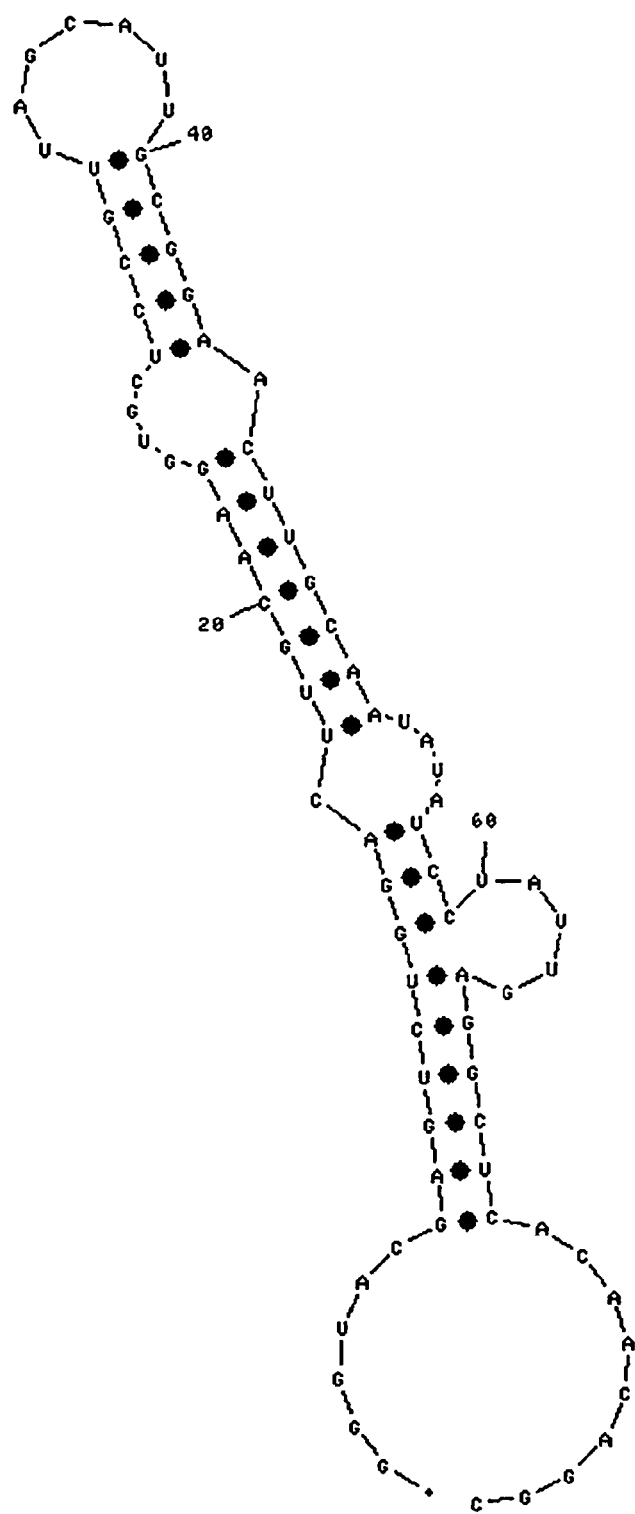
FIG. 20 shows the putative secondary structure of the RNA shown by SEQ ID NO:20.
Figure 21:
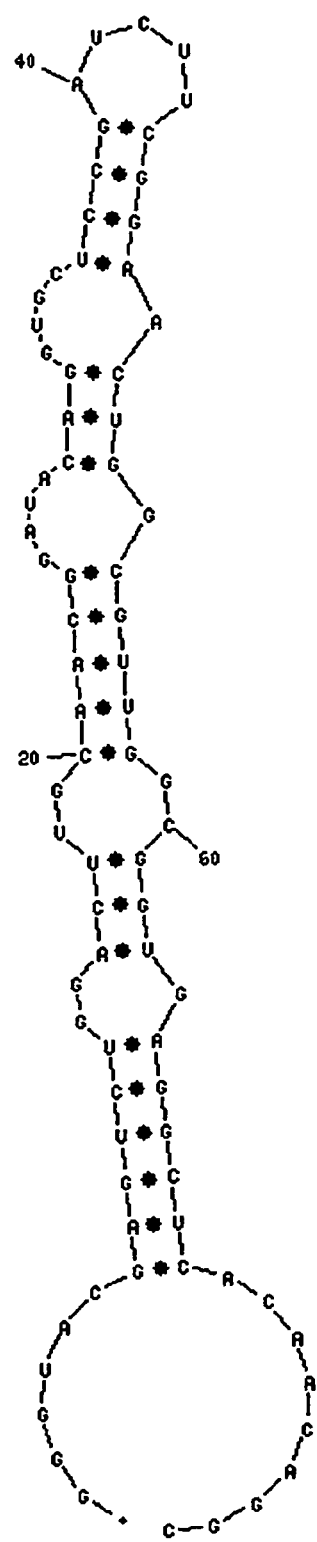
FIG. 21 shows the putative secondary structure of the RNA shown by SEQ ID NO:21.
Figure 22:
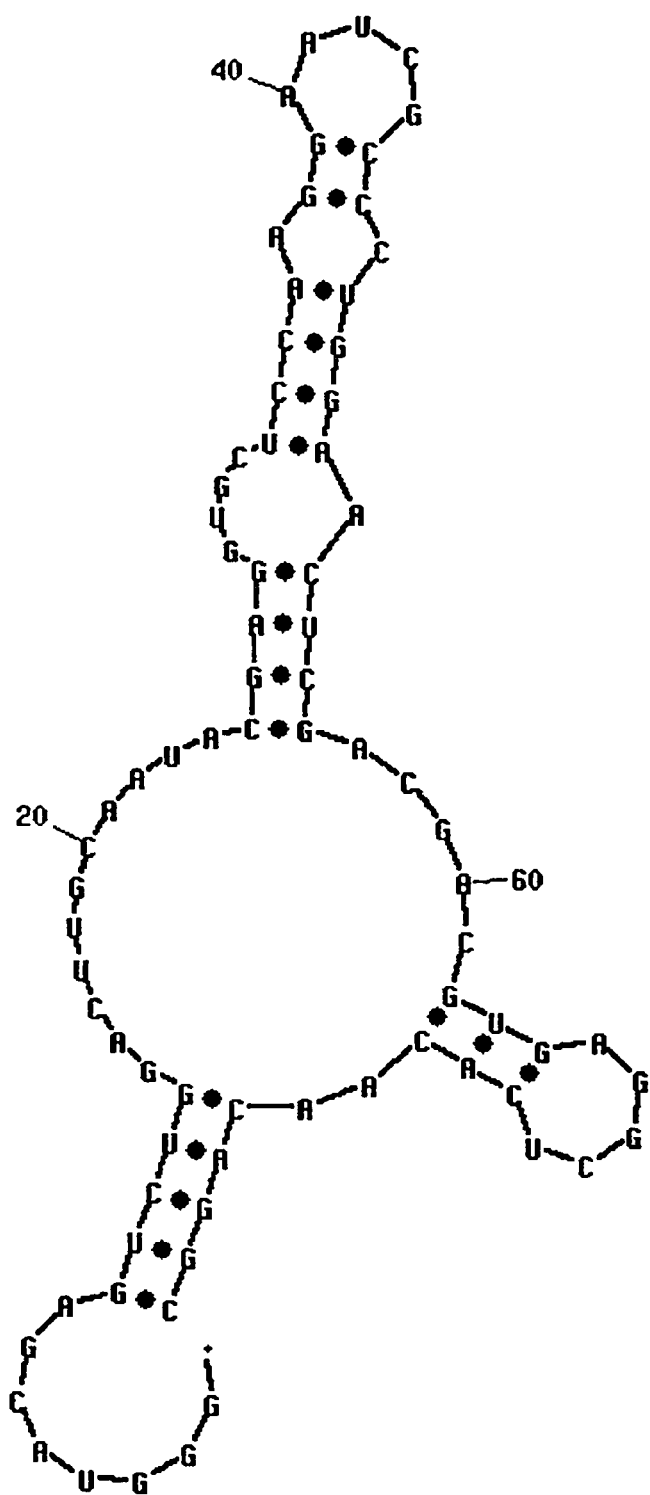
FIG. 22 shows the putative secondary structure of the RNA shown by SEQ ID NO:22.
Figure 23:
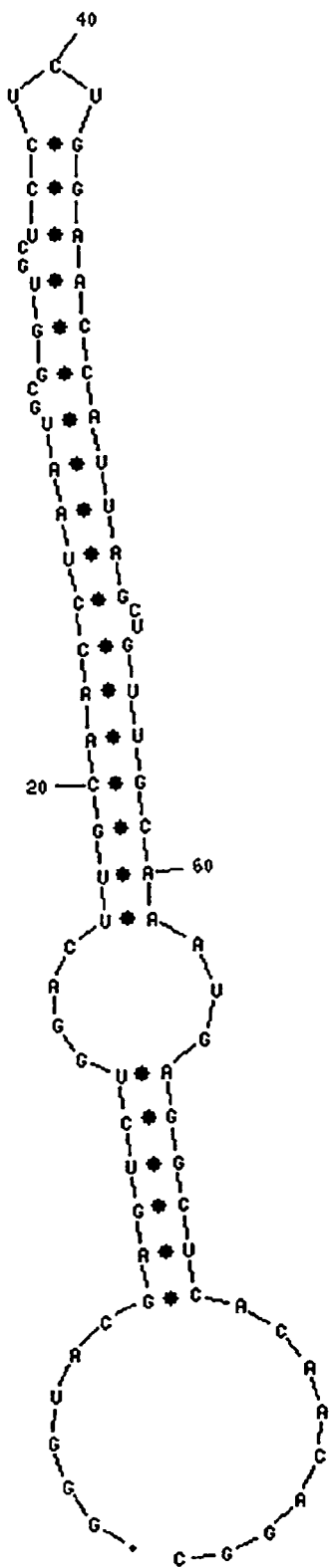
FIG. 23 shows the putative secondary structure of the RNA shown by SEQ ID NO:23.

After completion of 7 rounds, the RNAs shown by SEQ ID NO:19, 20, and 21 were present in 13, 9, and 6 clones, respectively, of the 48 clones sequenced. These RNAs comprised the shared sequence GGUGCU. When the secondary structures were estimated using the MFOLD program, the RNAs of SEQ ID NO:20 and 21 comprised the same bulge structure as that of the RNA of SEQ ID NO:1, but did not comprise the RNA of SEQ ID NO:19 (FIGS. 19 to 21). Next, the sequences of the RNAs that were present only in 1 clone of the 48 clones were examined extensively; the RNAs shown by SEQ ID NO:22 and 23 comprised the shared sequence GGUGCU. When the secondary structures were estimated using the MFOLD program, the RNA of SEQ ID NO:22 comprised a shared bulge structure, whereas the RNA of SEQ ID NO:23 did not comprise the same. Additionally, there were 15 sequences found in 1 clone. None of the latter sequences comprised GGUGCU. Of these sequences, eight sequences were examined for binding affinity; none of them had binding affinity.

Using RNAs formed with pyrimidine base-containing nucleotides fluorated at the 2'-position of ribose and natural type purine base-containing nucleotides, three different runs of SELEX were performed; in all these runs, RNAs comprising the shared sequence GGUGCU were selected. There was no special feature in the sequences on both sides of this shared sequence; it was postulated that GGUGCU is important for the binding to IgG. When the secondary structures were estimated using the MFOLD program, it is postulated that almost all of the RNAs selected comprise the bulge structure of GGUGCU, and that all the RNA having the shared sequence assume the bulge structure of GGUGCU.

Example 2

Evaluation of Binding Affinity

The binding affinities of the RNAs shown by SEQ ID NO:1 to 9 for human IgG-Fc were determined by a surface plasmon resonance method. Used for the measurements was BIAcore 2000 manufactured by BIAcore. Used as the sensor chip was the SA chip having streptavidin immobilized thereon. Bound thereto was about 1000 RU of 16-residue Poly dT having biotin bound to the 5' end thereof. The RNA for use as the ligand had 16-residue Poly A added to the 3' end thereof, and immobilized to the SA chip via a bond between dT and A. The amount immobilized was adjusted to about 1000 RU by injecting 60 μL at a concentration of 0.01 μg/μL. 70 μL of IgG-Fc for analyte (manufactured by Athens Research & Technology), adjusted to 0.6 μM, was injected. The running buffer used had the same components as those of the solution A used in SELEX.

Figure 24:
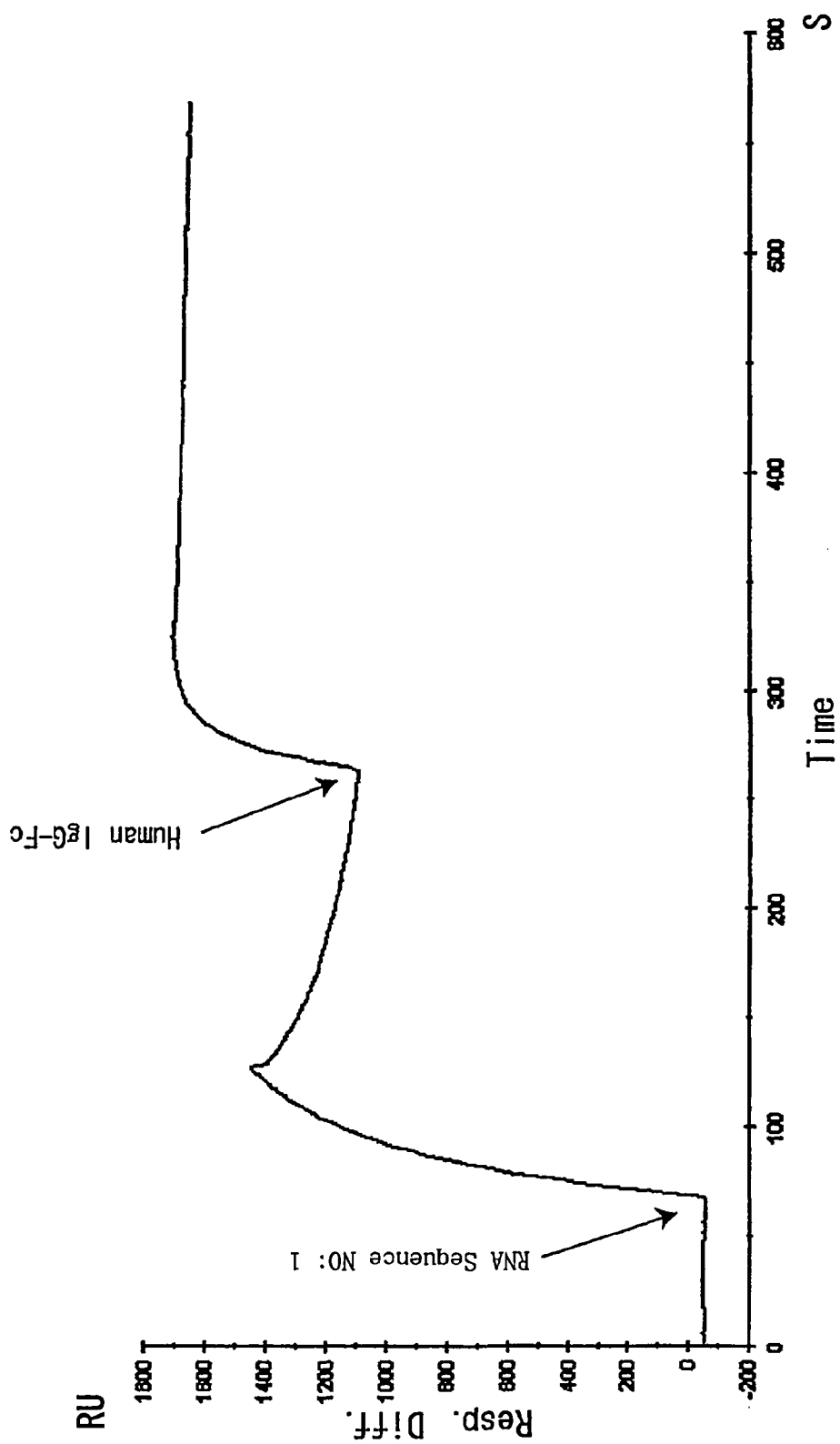
FIG. 24 shows a sensorgram obtained by surface plasmon resonance analysis, showing the profile of the binding of the RNA shown by SEQ ID NO:1 and human IgG-Fc. The RNA having 16-residue Poly A added to the 3' end thereof was immobilized onto a sensor chip via an A-dT bond, IgG-Fc was injected, and the interaction with the RNA was examined. On the ordinate, RU indicates Relative Unit, and Resp.Diff. indicates Response Differences. The abscissa indicates time (seconds). These designations on the ordinate and the abscissa also apply to FIGS. 25 to 31 and 42 below.
Figure 25:
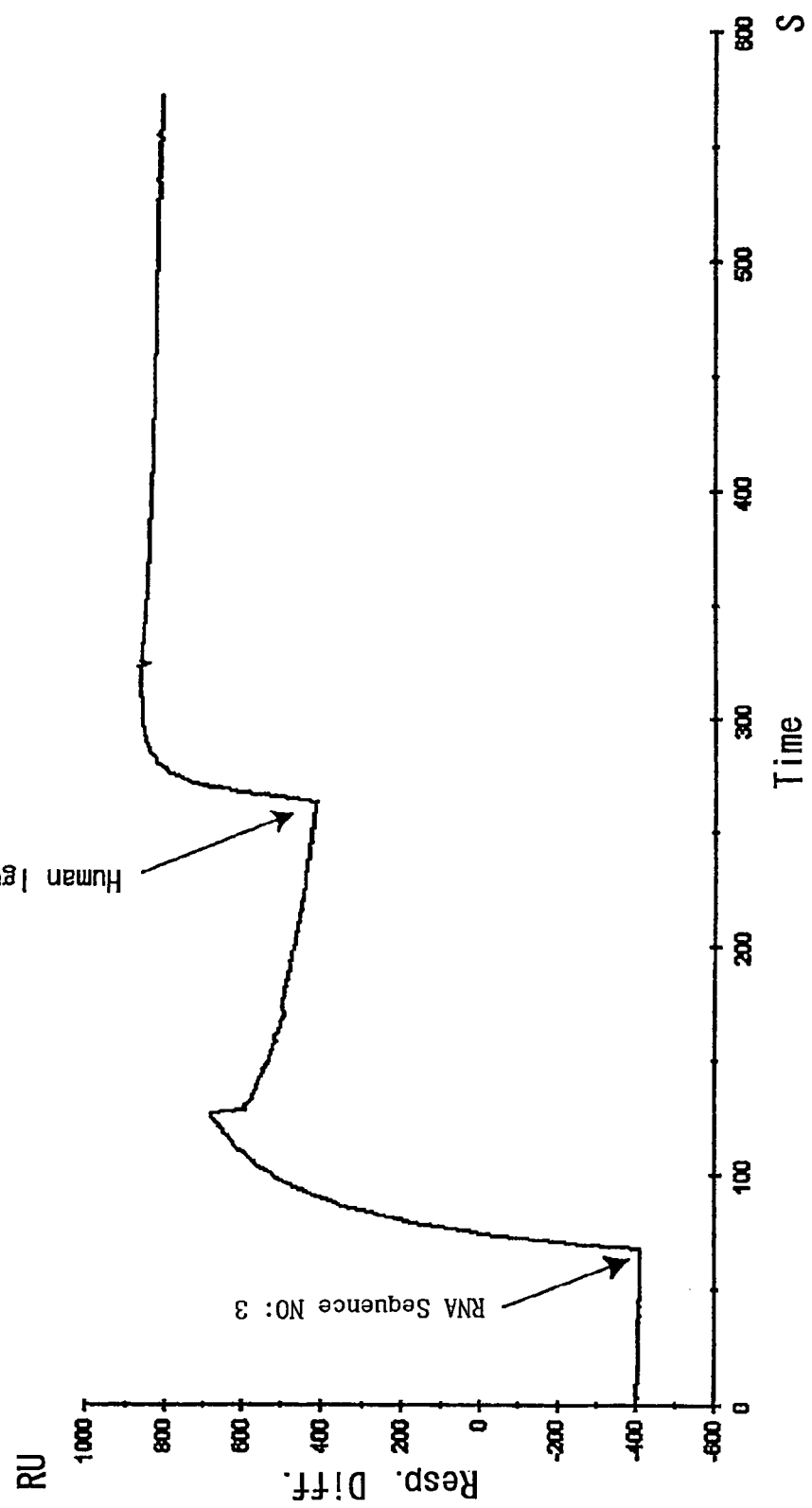
FIG. 25 shows a sensorgram obtained by surface plasmon resonance analysis, showing the profile of the binding of the RNA shown by SEQ ID NO:3 and human IgG-Fc. The RNA having 16-residue Poly A added to the 3' end thereof was immobilized onto a sensor chip via an A-dT bond, IgG-Fc was injected, and the interaction with the RNA was examined.
Figure 26:
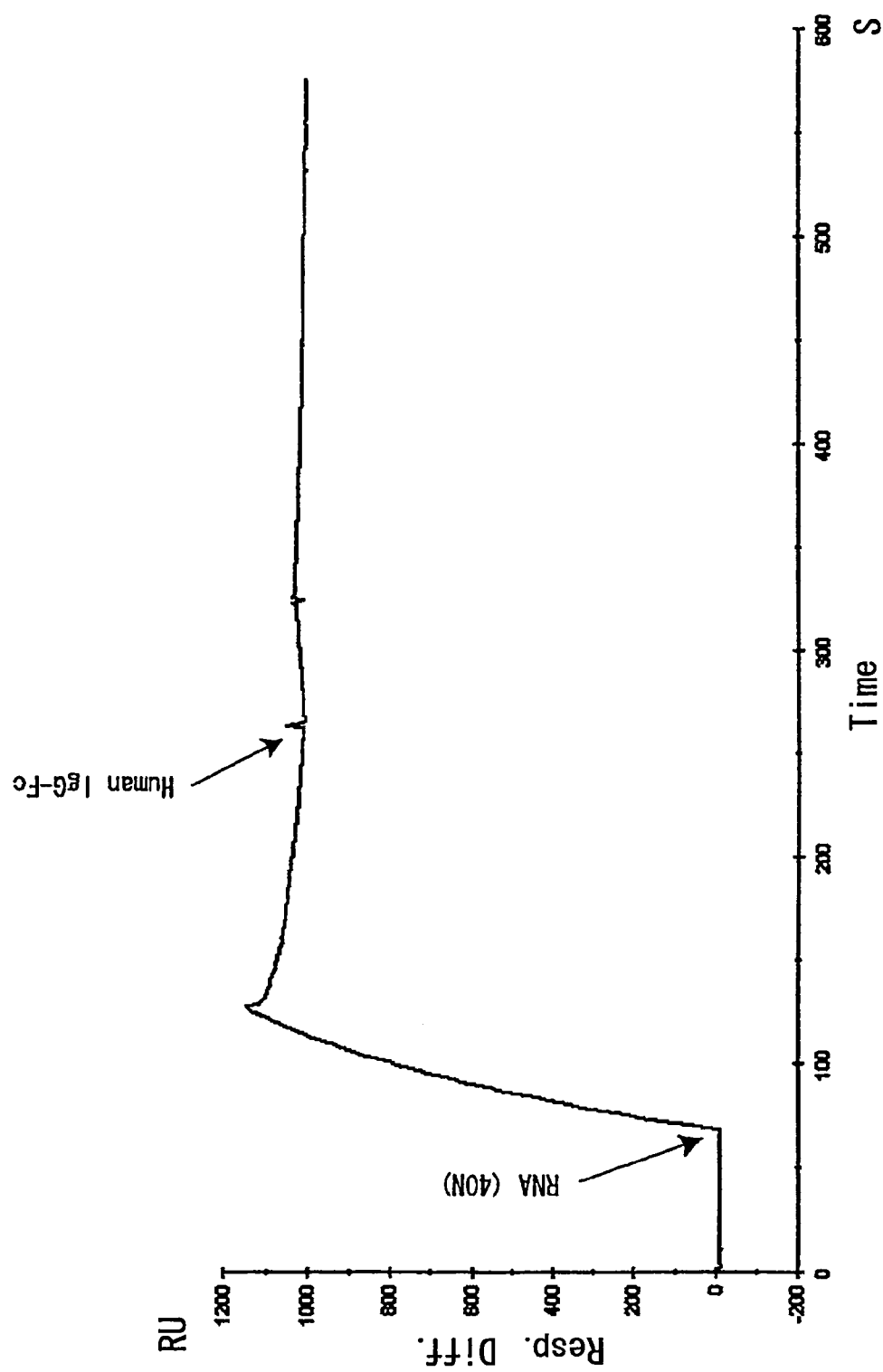
FIG. 26 shows a sensorgram obtained by surface plasmon resonance analysis, showing the profile of the binding of a random sequence RNA pool and human IgG-Fc. The RNA having 16-residue Poly A added to the 3' end thereof was immobilized onto a sensor chip via an A-dT bond, IgG-Fc was injected, and the interaction with the RNA was examined.

Sensorgrams obtained by immobilizing the RNA shown by SEQ ID NO:1 or 3, and injecting IgG-Fc, are shown in FIG. 24 or 25, respectively. How the RNA and IgG-Fc are bound together is shown. For control, a measurement was performed on an immobilized RNA pool comprising a random sequence; IgG-Fc did not bind (FIG. 26). The same measurement was performed on the RNAs shown by SEQ ID NO:2 to 9; all of the RNAs bound to IgG-Fc.

Next, the binding affinities for full-length human IgG1 were determined in the same manner. All the RNAs shown by SEQ ID NO:1 to 9 bound to IgG1. The RNA pool containing random sequences did not exhibit binding affinity.

Next, kinetic analysis was performed using different concentrations of IgG (0.6 μM to 0.05 μM) to determine the dissociation constant (Kd) of each RNA aptamer. The dissociation constant was determined by immobilizing an RNA having 16-residue PolyA added to the 3' end thereof onto a sensor chip via an A-dT bond, injecting different concentrations of IgG (0.6 μM to 0.05 μM), and performing surface plasmon resonance. The results are shown in Table 1.

TABLE 1

| RNA aptamer  | human IgG1          | human IgG1-Fc       |
|--------------|---------------------|---------------------|
| SEQ ID NO: 1 | $3 \times 10^{-10}$ | $1.1 \times 10^{-12}$ |
| SEQ ID NO: 2 | $5 \times 10^{-9}$  | $7.4 \times 10^{-9}$  |
| SEQ ID NO: 3 | $1 \times 10^{-8}$  | $5 \times 10^{-13}$   |
| SEQ ID NO: 4 | $2 \times 10^{-8}$  | $6 \times 10^{-12}$   |
| SEQ ID NO: 5 | $3 \times 10^{-8}$  | $6 \times 10^{-13}$   |
| SEQ ID NO: 6 | $1 \times 10^{-9}$  | $3 \times 10^{-9}$    |
| SEQ ID NO: 7 | $1 \times 10^{-12}$ | $1 \times 10^{-12}$   |
| SEQ ID NO: 8 | $3 \times 10^{-9}$  | $7 \times 10^{-9}$    |
| SEQ ID NO: 9 | $2 \times 10^{-8}$  |                     |
| SEQ ID NO: 10 | $6 \times 10^{-9}$ |                     |
| SEQ ID NO: 11 | $1 \times 10^{-9}$ |                     |
| SEQ ID NO: 14 | $4 \times 10^{-9}$ |                     |
| SEQ ID NO: 15 | $5 \times 10^{-9}$ |                     |
| SEQ ID NO: 16 | $6 \times 10^{-9}$ |                     |
| SEQ ID NO: 17 | $1 \times 10^{-8}$ |                     |

The binding affinities of the RNAs shown by SEQ ID NO:19 to 23 for human IgG1 were examined using a surface plasmon resonance method. As a result, all the RNAs were found to have binding affinity for IgG1. As estimated using the MFOLD program, the secondary structures of the RNAs shown by SEQ ID NO:19 and 23 did not comprise a shared bulge structure, but both had binding affinity for human IgG1.

The binding affinities of aptamers were measured using Biacore2000 (manufactured by Biacore). Biacore2000 incorporates kinetic analytical software; by fitting a theoretical equation to the shape of a sensorgram obtained, the dissociation constant can be determined. To the long aptamers shown by SEQ ID NO:1 to 9 and 19 to 23, the theoretical equation for the 1:1 binding model fitted well, whereas to the short aptamers such as the one shown by SEQ ID NO:17, the theoretical equation for the Bivalent model, a 1:2 binding model, fitted better. Because antibodies have a symmetric structure, it is a quite easily acceptable thought that two aptamers are bound to one antibody.

Thus, it was confirmed that the RNAs shown by SEQ ID NO:1 to 9 and 19 to 23, prepared by the SELEX method, have binding affinity for human IgG. This shows that the shared sequence GGUGCU is important for the binding to IgG.

Example 3

Miniaturization of RNA Aptamers

The lengths of the RNAs shown by SEQ ID NO:1 to 9 and 19 to 23 are about 70 residues; if the length can be shortened to about 40 residues or less, it will become possible to prepare an RNA aptamer by chemical synthesis. Hence, attempts were made to miniaturize the RNAs shown by SEQ ID NO:1 to 9 and 19 to 23. Here, the RNAs shown by SEQ ID NO:1 to 9 and 19 to 23 have been fluorated at the 2'-position of the ribose of each pyrimidine base-containing nucleotide (U, C), and the purine base-containing nucleotides (A, G) are of the natural RNA type. All short RNAs newly prepared in this Example have been fluorated at the 2'-position of the ribose of the pyrimidine base.

First, miniaturization was attempted on the basis of the RNA shown by SEQ ID NO:1. The RNA shown by SEQ ID NO:10 was prepared by cutting the 5'-end GGGACAC and 3'-end GAGAG of the RNA shown by SEQ ID NO:1, and adding GG to the 5' end thereof for transcription. The RNA shown by SEQ ID NO:11 was prepared by cutting the 5'-end GGAAU and the 3'-end ACAU of the RNA shown by SEQ ID NO:10. The RNA shown by SEQ ID NO:12 was prepared by cutting the 5'-end GGACGAGUU and 3'-end AACGGCCG of the RNA shown by SEQ ID NO:11, and adding GG to the 5' end thereof and CC to the 3' end thereof. The RNA shown by SEQ ID NO:13 was prepared by replacing the stem loop structure behind the bulge of GGUGCU of the RNA shown by SEQ ID NO:12 with the stem loop structure of the RNA shown by SEQ ID NO:2. The RNA shown by SEQ ID NO:14 was prepared by replacing the loop portion of the RNA shown by SEQ ID NO:13 with the GAAA tetra-loop. The RNA shown by SEQ ID NO:15 was prepared by removing two base pairs from the first stem of the RNA shown by SEQ ID NO:13 to shorten the whole stem. The RNA shown by SEQ ID NO:16 was prepared by removing three base pairs from the second stem of the RNA shown by SEQ ID NO:13 to shorten the whole stem. The RNA shown by SEQ ID NO:17 was prepared by removing two base pairs from the first stem of the RNA shown by SEQ ID NO:16 to shorten the whole stem. The RNA shown by SEQ ID NO:18 was prepared by removing one base pair from the second stem of the RNA shown by SEQ ID NO:17 to shorten the whole stem. The binding affinities of the miniaturized RNAs were confirmed using a surface plasmon resonance method.

Measurements were performed in the same manner as Example 1 by immobilizing an RNA having 16-residue Poly A added thereto via an A-pT bond, and injecting IgG thereto. As a result, the RNAs shown by SEQ ID NO:10 to 18, which comprise the GGUGCU consensus sequence, were found to have binding affinity for human IgG1. Of these RNAs, the RNA shown by SEQ ID NO:18 consisted of 21 residues. The respective dissociation constants are shown in Table 1.

A mutant wherein the 8th nucleotide C of the RNA shown by SEQ ID NO:17 was replaced with U was prepared. This C is the C of the shared sequence GGUGCU. As a result of surface plasmon resonance analysis, this mutant was found to have no binding affinity for human IgG1. This fact indicates that the shared sequence GGUGCU is important for the binding to IgG.

Thus, by miniaturizing the RNA shown by SEQ ID NO:1, an RNA aptamer with a length such that chemical synthesis is possible was prepared. It was also shown that if a bulge structure for the shared sequence GGUGCU is present, the binding affinity for IgG is retained.

Example 4

Evaluation of Species Specificity

Whether or not the prepared RNA aptamers also have binding affinity for subclasses of IgG other than human IgG1 or for IgG of animal species other than humans was determined using a surface plasmon resonance method. Measurements were performed in the same manner as Example 1 by immobilizing a nucleic acid having 16-residue Poly A added thereto via an A-pT bond, and injecting IgG thereto. Used as the RNA aptamers were the nucleic acids shown by SEQ ID NO:1 and 17. Used as the antibodies were human IgG1 (manufactured by Calbiochem), human IgG2 (manufactured by Calbiochem), human IgG3 (manufactured by Calbiochem), human IgG4 (manufactured by Calbiochem), mouse IgG1 (manufactured by Chemicon International), mouse IgG2a (manufactured by Chemicon International), mouse IgG2b (manufactured by Zymed Laboratories), mouse IgG3 (manufactured by Bethyl Laboratories), rat IgG1 (manufactured by R & D Systems), rat IgG2a (manufactured by Zymed Laboratories), rat IgG2b (manufactured by Zymed Laboratories), rat IgG2c (manufactured by UK-Serotec), rabbit IgG (manufactured by Zymed Laboratories), bovine IgG1 (manufactured by Bethyl Laboratories), bovine IgG2 (manufactured by Bethyl Laboratories), chicken IgG (manufactured by Rockland), dog IgG (manufactured by Rockland), cat IgG (manufactured by Bethyl Laboratories), guinea pig IgG (manufactured by Biogenesis), hamster IgG (manufactured by Rockland), and swine IgG (manufactured by Rockland). The results are shown in Table 2.

TABLE 2

| IgG | SEQ ID NO: 1 | binding strength SEQ ID NO: 17 | *Protein A |
|---|---|---|---|
| Human IgG1 | +++ | +++ | +++ |
| Human IgG2 | +++ | +++ | +++ |
| Human IgG3 | ++ | ++ | ++ |
| Human IgG4 | +++ | +++ | +++ |
| Human IgA | nd | − | variable |
| Human IgD | − | − | − |
| Human IgE | − | − | − |
| Human IgM | nd | + | variable |
| Mouse IgG1 | − | − | + |
| Mouse IgG2a | − | − | +++ |
| Mouse IgG2b | − | − | +++ |
| Mouse IgG3 | − | − | +++ |
| Rat IgG1 | − | − | ++ |
| Rat IgG2a | − | − | − |
| Rat IgG2b | − | − | − |
| Rat IgG2c | − | − | +++ |
| Rabbit IgG | − | − | +++ |
| Bovine IgG1 | − | − | − |
| Bovine IgG2 | − | − | +++ |
| Chicken IgG | − | − | − |
| Dog IgG | − | − | +++ |
| Cat IgG | − | − | +++ |
| Guinea pig IgG | − | − | +++ |
| Hamster IgG | +++ | + | + |
| Swine IgG | + | + | +++ |

*The data on Protein A was cited from a catalogue of Amersham Biosciences.
+ indicates binding strength; a larger number of + marks means higher binding.
− means no binding.
nd means that no measurement was performed.

As shown in Table 2, the RNAs shown by SEQ ID NO:1 and 17 were found to having binding affinity for human IgG1, human IgG2, human IgG3, human IgG4, hamster IgG, and swine IgG, but not to have binding affinity for the IgG of any other animal species. The nucleic acids shown by SEQ ID NO:1 and 17 also did not have binding affinity for human IgD (manufactured by Biogenesis) and human IgE (manufactured by Calbiochem). Furthermore, the nucleic acid shown by SEQ ID NO:17 did not have binding affinity for human IgA (manufactured by Bethyl Laboratories), but exhibited very weak but measurable binding affinity for human IgM (manufactured by Chemicon International).

Thus, the RNA aptamers provided by the present invention were found to be RNAs that bind specifically to human, hamster, and swine IgG. Regarding human IgG, the RNA aptamers were found to bind to all of IgG1 to 4, irrespective of subclass. This is a characteristic not found in Protein A, which is currently used as a ligand for antibody purification resin.

Example 5

Investigation of Binding Site of RNA Aptamer (FcγR)-1

An Fc region of IgG binds to a receptor protein (FcγR) expressed in immunocompetent cells such as macrophages and neutrophils to promote cell activation or suppression. Hence, whether or not an RNA provided by the present invention has bound to the FcγR binding site of IgG was determined using a surface plasmon resonance method. First, an RNA aptamer having 16-residue Poly A added thereto was immobilized in the same manner as Example 1, and human IgG1 was injected thereto and bound to the RNA aptamer, after which FcγR was injected. It is thought that if the RNA aptamer binding site of IgG overlaps the binding site of FcγR over the entire portion or in a primary portion, FcγR cannot bind to the IgG bound to the RNA aptamer. If the binding strength between IgG and FcγR is stronger than the binding strength between IgG and the RNA aptamer, and a substitution reaction between the RNA aptamer and FcγR occurs, it is postulated that IgG dissociates from the immobilized RNA aptamer, forms a complex with FcγR, and is washed away.

Figure 27:
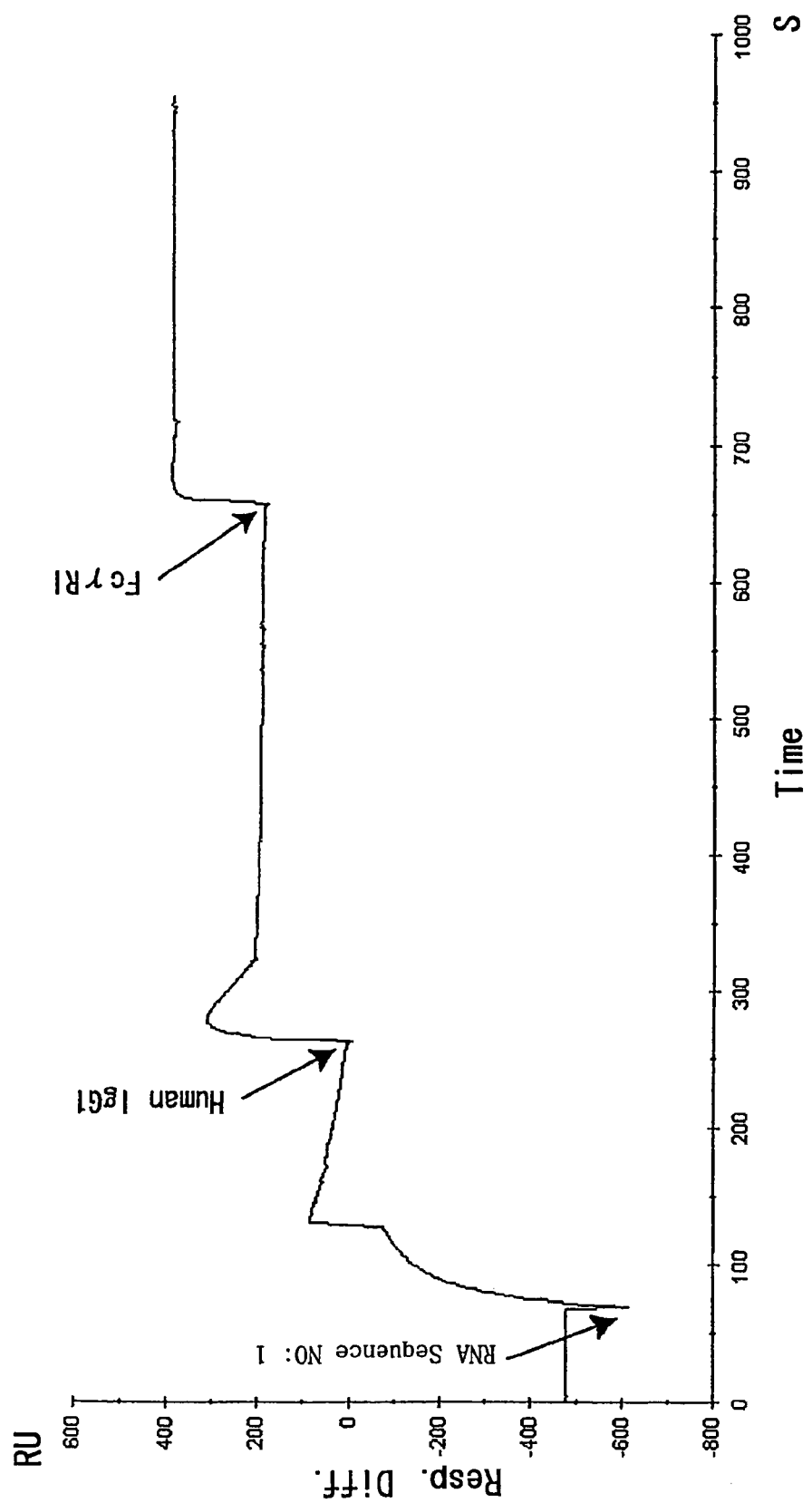
FIG. 27 shows a sensorgram obtained by surface plasmon resonance analysis, showing the mode of the formation of a complex of the RNA shown by SEQ ID NO:1, human IgG1 and human FcγRI. The RNA having 16-residue Poly A added to the 3' end thereof was immobilized onto a sensor chip via an A-dT bond, IgG1 was injected and bound to the RNA, and then FcγRI was injected, and the interaction with IgG1 was examined.
Figure 28:
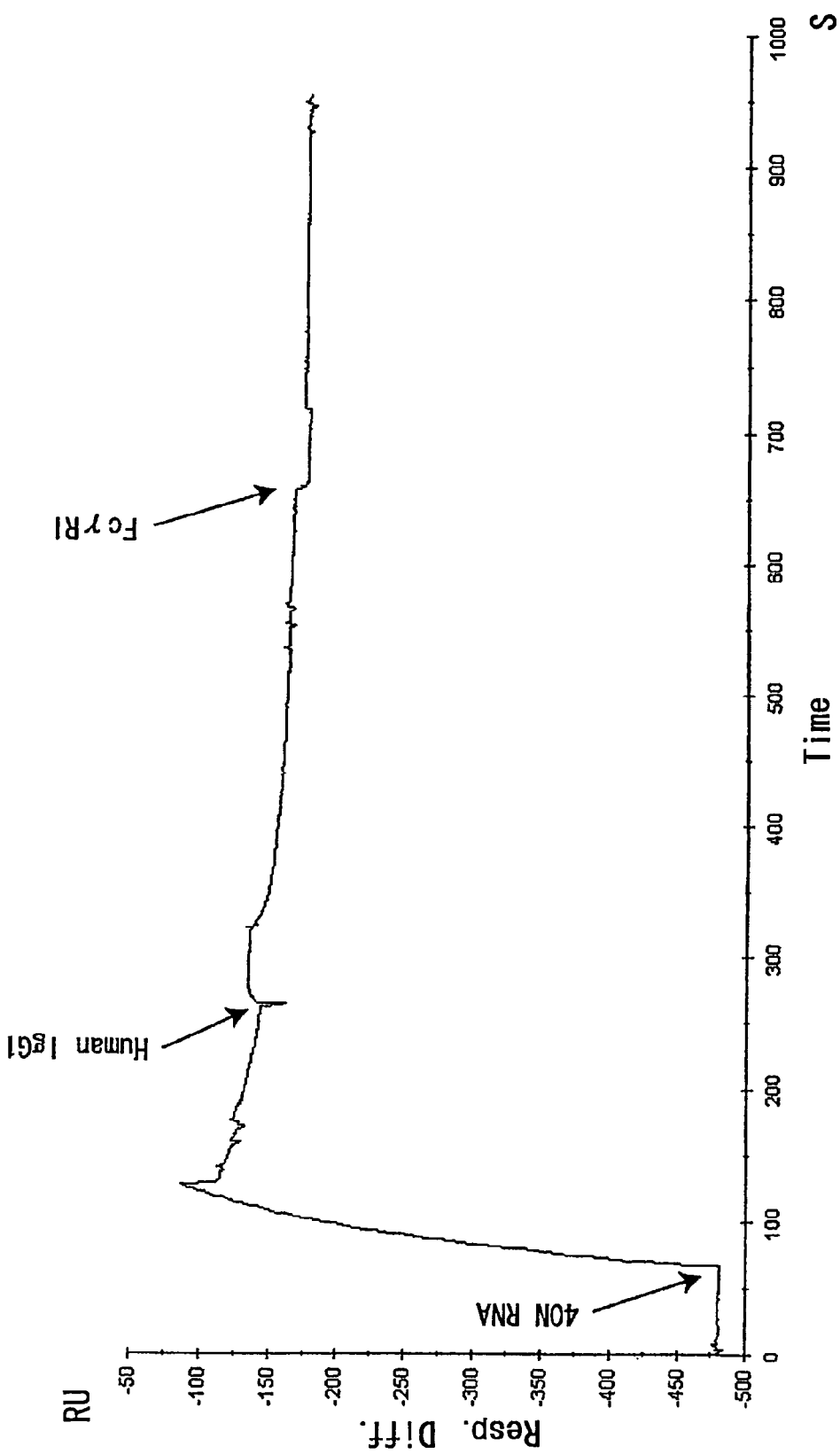
FIG. 28 shows a sensorgram obtained by surface plasmon resonance analysis, showing the profile of the binding of an RNA pool comprising a random sequence, human IgG1, and human FcγR. The RNA having 16-residue Poly A added to the 3' end thereof was immobilized onto a sensor chip via an A-dT bond, IgG1 was injected, and then FcγRI was injected.

Measurements were performed using the RNA shown by SEQ ID NO:1 as the RNA aptamer, human IgG-Fc (manufactured by Athens Research & Technology) as the IgG, and human FcγRI (manufactured by R & D Systems) as the FcγR. As a result, an increase in the signal due to the binding of FcγRI was observed after IgG-Fc (FIG. 27), it was found that a tertiary complex of RNA aptamer, IgG-Fc, and FcγRI was formed. If an RNA pool comprising random sequences is used for control, neither IgG-Fc nor FcγRI bound (FIG. 28).

Thus, the RNA aptamer was found to be bound to a portion other than the FcγRI binding site of IgG.

Example 6

Investigation 2 of Binding Site of RNA Aptamer (Protein A)-2

Figure 29:
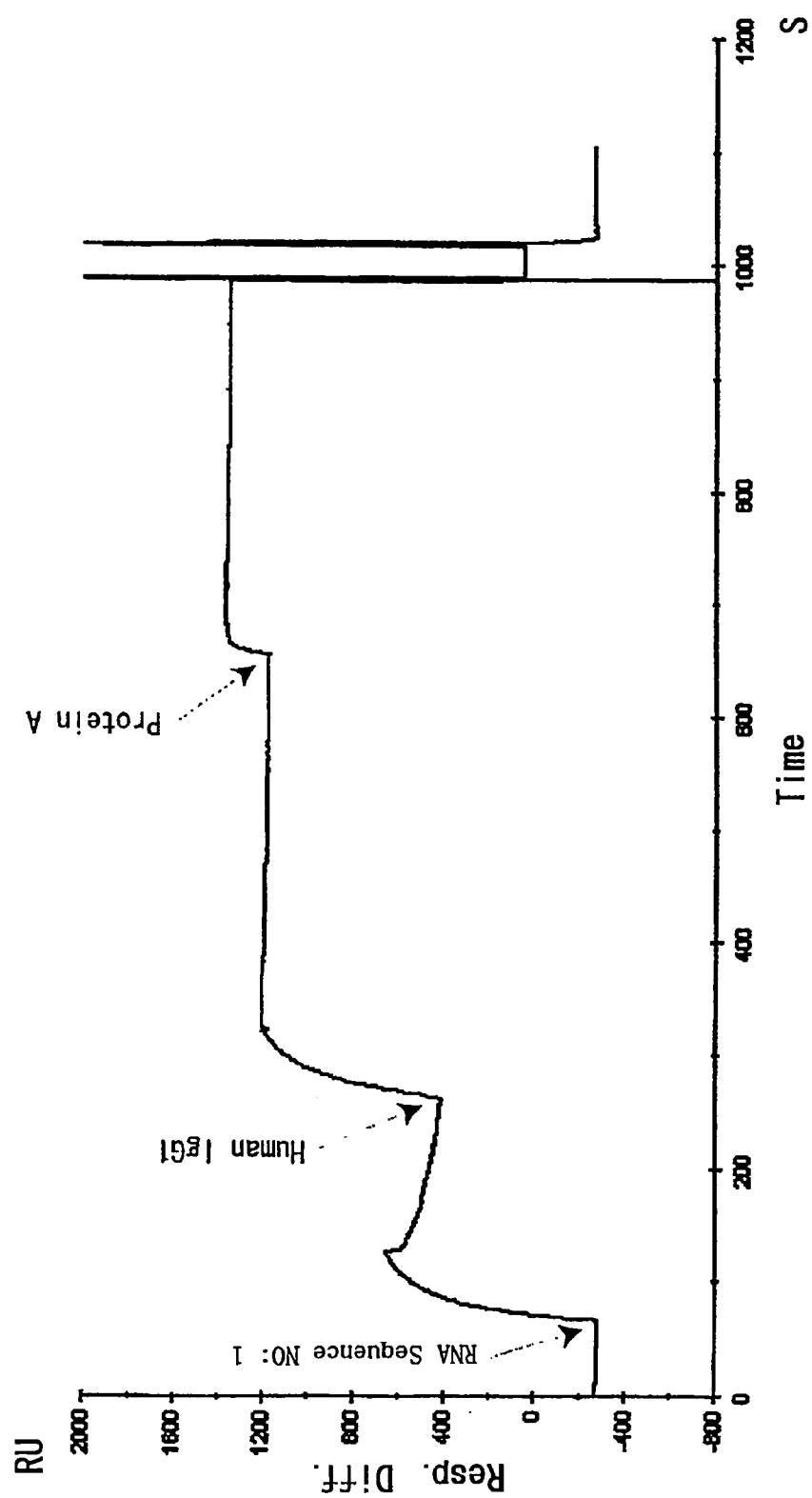
FIG. 29 shows a sensorgram obtained by surface plasmon resonance analysis, showing the profile of the formation of a complex of the RNA shown by SEQ ID NO:1, human IgG1 and Protein A. The RNA having 16-residue Poly A added to the 3' end thereof was immobilized onto a sensor chip via an A-dT bond, IgG1 was injected and bound to the RNA, and then Protein A was injected, and the interaction with IgG1 was examined.
Figure 30:
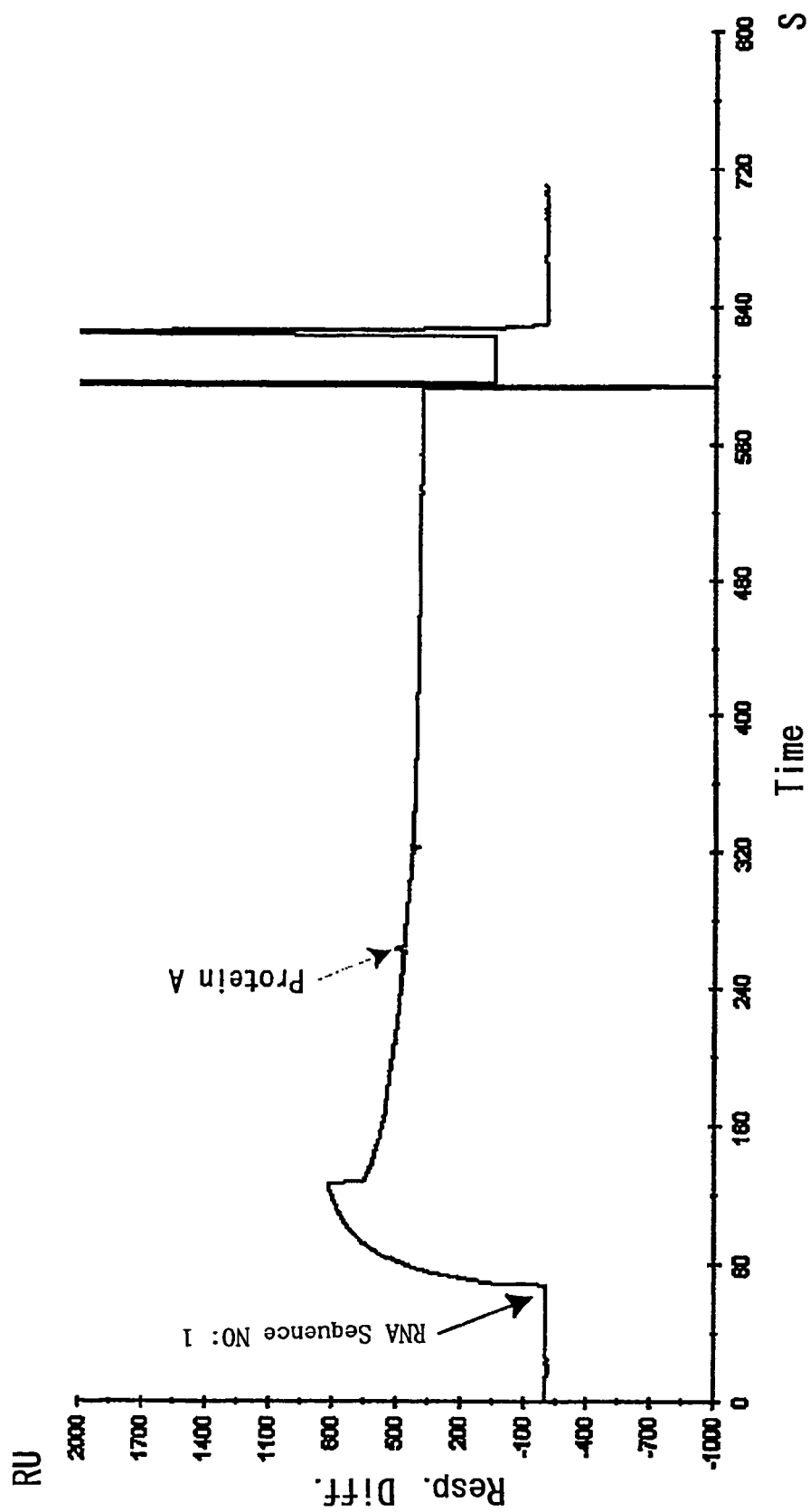
FIG. 30 shows a sensorgram obtained by surface plasmon resonance analysis, showing the profile of the binding of the RNA aptamer shown by SEQ ID NO:1 and Protein A. The RNA having 16-residue Poly A added to the 3' end thereof was immobilized onto a sensor chip via an A-dT bond, Protein A was injected, and the interaction with the RNA was examined.

As another substance that binds to IgG-Fc, Protein A is known well. Since Protein A binds specifically to an Fc region of IgG, it is used as a ligand for a separating agent for antibody purification. Hence, in the same manner as Example 5, whether or not an RNA provided by the present invention has bound to the Protein A binding site of IgG. First, the RNA aptamer shown by SEQ ID NO:1, which has 16-residue Poly A added to the 3' end thereof, was immobilized in the same manner as Example 1, and human IgG1 (manufactured by Calbiochem) was supplied thereto and bound to the RNA aptamer, after which Protein A (manufactured by MP Biomedicals) was injected. As a result, an increase in the signal due to the binding of Protein A was observed after IgG1 binding (FIG. 29); therefore, it was found that a tertiary complex of RNA aptamer, IgG1, and Protein A was formed. For control, measurements were performed in which Protein A was injected after immobilizing the RNA aptamer shown by SEQ ID NO:1; no binding of Protein A was observed (FIG. 30).

Thus, the RNA aptamer was found to have bound to a portion different from the Protein A binding site of IgG-Fc.

Example 7

Method of 2' Modification of RNA Aptamer and binding affinity for IgG

The RNA aptamer prepared in Example 1 was found to be fluorated at the 2'-position of the ribose of each pyrimidine base-containing nucleotide. In this Example, RNAs were prepared using different methods of modifying the 2'-position of ribose, and their binding affinities for IgG were examined using a surface plasmon resonance method.

First, the natural type RNAs shown by SEQ ID NO:11 and 13 were prepared, and their binding affinities for IgG were examined. The natural type RNAs were prepared by chemically synthesizing a template DNA (manufactured by OPERON), and transcribing using T7 RNA polymerase (manufactured by Takara). The binding affinities were measured by a surface plasmon resonance method as in Example 1. Used as the IgG was human IgG1 (manufactured by Calbiochem). As a result, it was found that the amount of IgG1 bound decreased, but the natural type RNAs shown by SEQ ID NO:11 and 13 have binding affinity for IgG.

Next, based on SEQ ID NO:17, the following differently modified RNAs shown by SEQ ID NO:17 (modified variant 23F1) to SEQ ID NO:17 (modified variant 23F31) were prepared.

SEQ ID NO: 17
G(OH)G(OH)A(OH)G(OH)G(OH)U(F)G(OH)C(F)U(F)C(F)C(F)

G(OH)A(OH)A(OH)A(OH)G(OH)G(OH)A(OH)A(OH)C(F)U(F)C (F)C(F)A(H)A(H)A(H)A(H)A(H)A(H)A(H)A(H)A(H)A(H)A (H)A(H)A(H)A(H)A(H)A(H)

SEQ ID NO: 17 (modified variant 23F1)
G(OH)G(OH)A(OH)G(OH)G(OH)U(F)G(OH)C(F)U(F)C(H)C(H)

G(OH)A(OH)A(OH)A(OH)G(OH)G(OH)A(OH)A(OH)C(F)T(H)C (H)C(H)A(H)A(H)A(H)A(H)A(H)A(H)A(H)A(H)A(H)A(H)A (H)A(H)A(H)A(H)A(H)A(H)

SEQ ID NO: 17 (modified variant 23F2)
G(H)G(H)A(OH)G(OH)G(OH)U(F)G(OH)C(F)U(F)C(F)C(F)G (H)A(H)A(H)A(H)G(OH)G(OH)A(OH)A(OH)C(F)U(F)C(H)C (H)A(H)A(H)A(H)A(H)A(H)A(H)A(H)A(H)A(H)A(H)A(H)A (H)A(H)A(H)A(H)A(H)

SEQ ID NO: 17 (modified variant 23F3)
G(H)G(H)A(H)G(OH)G(OH)U(F)G(OH)C(F)U(F)C(H)C(H)G (H)A(H)A(H)A(H)G(H)G(H)A(OH)A(OH)C(F)T(H)C(H)C(H)

A(H)A(H)A(H)A(H)A(H)A(H)A(H)A(H)A(H)A(H)A(H)A(H)

A(H)A(H)A(H)A(H)

SEQ ID NO: 17 (modified variant 23F10)
G(H)G(H)A(OH)G(OH)G(OH)U(F)G(OH)C(F)U(F)C(F)C(H)G (H)A(H)A(H)A(H)G(OH)G(OH)A(OH)A(OH)C(F)U(F)C(H)C -continued

```
(H)A(H)A(H)A(H)A(H)A(H)A(H)A(H)A(H)A(H)A (H)A(H)A(H)A(H)A(H)

SEQ ID NO: 17 (modified variant 23F11)
G(H)G(H)A(OH)G(OH)G(OH)U(F)G(OH)C(F)U(F)C(F)C(F)G (H)A(H)A(H)A(H)G(H)G(H)A(OH)A(OH)C(F)U(F)C(H)C(H)A (H)A(H)A(H)A(H)A(H)A(H)A(H)A(H)A(H)A(H)A(H)A (H)A(H)A(H)A(H)

SEQ ID NO: 17 (modified variant 23F12)
G(H)G(H)A(OH)G(OH)G(OH)U(F)G(H)C(F)U(F)C(F)C(F)G (H)A(H)A(H)A(H)G(OH)G(OH)A(OH)A(OH)C(F)U(F)C(H)C (H)A(H)A(H)A(H)A(H)A(H)A(H)A(H)A(H)A(H)A(H)A (H)A(H)A(H)A(H)A(H)

SEQ ID NO: 17 (modified variant 23F23)
G(H)G(H)A(OH)G(OH)G(OH)U(F)G(OH)C(H)U(F)C(H)C(H)G (H)A(H)A(H)A(H)G(OH)G(OH)A(H)A(H)C(F)U(F)C(H)C(H)A (H)A(H)A(H)A(H)A(H)A(H)A(H)A(H)A(H)A(H)A(H)A (H)A(H)A(H)A(H)

SEQ ID NO: 17 (modified variant 23F25)
G(OMe)G(OMe)A(OH)G(OH)G(OH)U(F)G(OH)C(F)U(F)C(F)C (F)G(OMe)A(OMe)A(OMe)A(OMe)G(OH)G(OH)A(OH)A(OH)C (F)U(F)C(OMe)C(OMe)A(H)A(H)A(H)A(H)A(H)A(H)A(H)A (H)A(H)A(H)A(H)A(H)A(H)A(H)A(H)

SEQ ID NO: 17 (modified variant 23F32)
G(H)G(H)A(OH)G(OH)G(OH)U(F)G(OH)C(H)U(F)C(H)C(H)G (H)A(H)A(H)A(H)G(OMe)A(OH)A(H)A(H)C(F)U(F)C(H)C(H)

A(H)A(H)A(H)A(H)A(H)A(H)A(H)A(H)A(H)A(H)A(H)A (H)A(H)A(H)A(H)

SEQ ID NO: 17 (modified variant 23F33)
G(H)G(H)A(OH)G(OH)G(OH)U(F)G(OH)C(H)U(F)C(H)C(H)G (H)A(H)A(H)A(H)G(OH)G(OMe)A(H)A(H)C(F)U(F)C(H)C(H)

A(H)A(H)A(H)A(H)A(H)A(H)A(H)A(H)A(H)A(H)A(H)A (H)A(H)A(H)A(H)

SEQ ID NO: 17 (modified variant 23F41)
G(OMe)G(OMe)A(OH)G(OH)G(OH)U(F)G(OH)C(F)U(OMe)C(F)

C(F)G(OMe)A(OMe)A(OMe)A(OMe)G(OH)G(OH)A(OH)A(OH)C (F)U(F)C(OMe)C(OMe)A(H)A(H)A(H)A(H)A(H)A(H)A(H)A (H)A(H)A(H)A(H)A(H)A(H)A(H)A(H)

SEQ ID NO: 17 (modified variant 23F42)
G(OMe)G(OMe)A(OH)G(OH)G(OH)U(F)G(OH)C(F)U(F)C(OMe)

C(F)G(OMe)A(OMe)A(OMe)A(OMe)G(OH)G(OH)A(OH)A(OH)C (F)U(F)C(OMe)C(OMe)A(H)A(H)A(H)A(H)A(H)A(H)A(H)A (H)A(H)A(H)A(H)A(H)A(H)A(H)A(H)

SEQ ID NO: 17 (modified variant 23F43)
G(OMe)G(OMe)A(OH)G(OH)G(OH)U(F)G(OH)C(F)U(F)C(F)C (OMe)G(OMe)A(OMe)A(OMe)A(OMe)G(OH)G(OH)A(OH)A(OH)C (F)U(F)C(OMe)C(OMe)A(H)A(H)A(H)A(H)A(H)A(H)A(H)A (H)A(H)A(H)A(H)A(H)A(H)A(H)A(H)

SEQ ID NO: 17 (modified variant 23F31)
G(H)G(H)A(OH)G(OH)G(OH)U(F)G(OH)C(H)U(OMe)C(H)C(H)

G(H)A(H)A(H)A(H)G(OH)G(OH)A(H)A(H)C(F)U(F)C(H)C(H)

A(H)A(H)A(H)A(H)A(H)A(H)A(H)A(H)A(H)A(H)A(H)A (H)A(H)A(H)A(H)
```

The RNAs were prepared by chemical synthesis (manufactured by Gene Design). Their binding affinities were measured by a surface plasmon resonance method as in Example 1. Used as the IgG was human IgG1 (manufactured by Calbiochem). As a result of the measurements, the RNA shown by SEQ ID NO:17 (modified variant 23F1) exhibited a binding affinity equivalent to that of the RNA shown by SEQ ID NO:17. The RNAs shown by SEQ ID NO:17 (modified variant 23F2), and SEQ ID NO:17 (modified variant 23F10) to SEQ ID NO:17 (modified variant 23F31) as shown above were higher in binding affinity than the RNA shown by SEQ ID NO:17. On the other hand, the RNA shown by SEQ ID NO:17 (modified variant 23F3) was lower in binding affinity than the RNA shown by SEQ ID NO:17.

Based on the nucleic acid shown by SEQ ID NO:15, modified variants were prepared in the same manner, and their binding affinities for human IgG were determined.

```
SEQ ID NO: 15
G(OH)G(OH)A(OH)G(OH)G(OH)U(F)G(OH)C(F)U(F)C(F)U(F)

G(OH)C(F)G(OH)A(OH)G(OH)C(F)C(F)A(OH)C(F)G(OH)C(F)

G(OH)G(OH)A(OH)A(OH)C(F)U(F)C(F)C(F)

SEQ ID NO: 15 (modified variant 30F-1)
G(H)G(H)A(OH)G(OH)G(OH)U(F)G(OH)C(F)U(F)C(F)U(F)G (OH)C(F)G(OH)A(H)G(H)C(H)C(H)A(H)C(F)G(OH)C(F)G (OH)G(OH)A(OH)A(OH)C(F)U(F)C(H)C(H)

SEQ ID NO: 15 (modified variant 30F-2)
G(H)G(H)A(OH)G(OH)G(OH)U(F)G(OH)C(F)U(F)C(F)U(H)G (OH)C(F)G(OH)A(H)G(H)C(H)C(H)A(H)C(H)G(OH)C(H)G (OH)G(OH)A(OH)A(OH)C(F)U(F)C(H)C(H)

SEQ ID NO: 15 (modified variant 30F-3)
G(H)G(H)A(OH)G(OH)G(OH)U(F)G(OH)C(F)U(F)C(F)C(H)G (OH)C(H)G(OH)A(H)G(H)C(H)C(H)A(H)C(H)G(OH)C(H)G (OH)G(OH)A(OH)A(OH)C(F)U(F)C(H)C(H)

SEQ ID NO: 15 (modified variant 30F-4)
G(H)G(H)A(OH)G(OH)G(OH)U(F)G(OH)C(F)U(F)C(F)C(F)G (OH)C(H)G(OH)G(H)A(H)A(H)A(H)C(H)G(OH)C(H)G(OH)G (OH)A(OH)A(OH)C(F)U(F)C(H)C(H)
```

As a result of measurements using a surface plasmon resonance method, the nucleic acids shown by SEQ ID NO:15 (modified variant 30E-1) to SEQ ID NO:15 (modified variant 30E-3) were found to have a binding affinity equivalent to that of the nucleic acid shown by SEQ ID NO:15.

Figure 31:
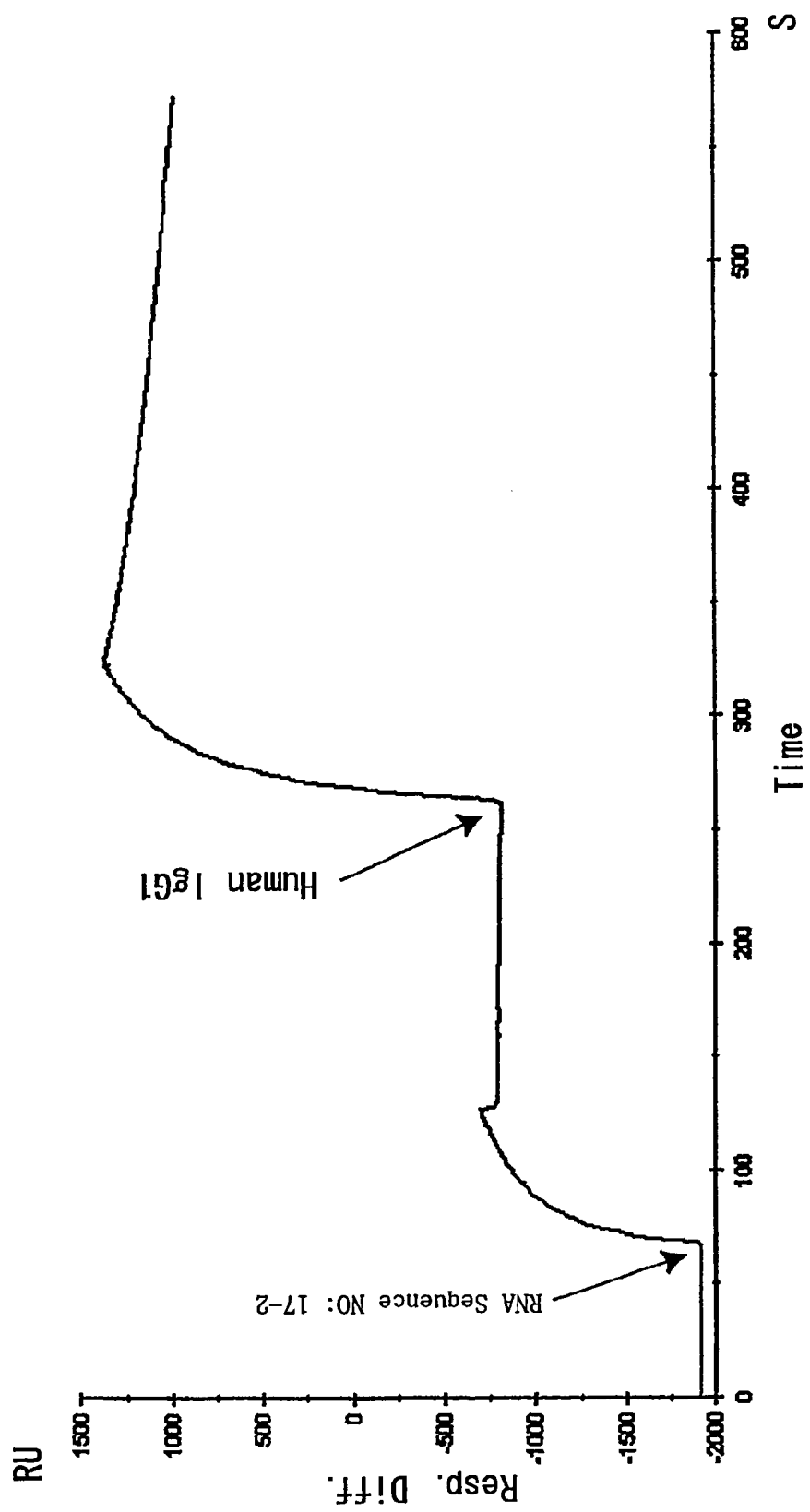
FIG. 31 shows a sensorgram obtained by surface plasmon resonance analysis, showing the profile of the binding of the RNA aptamer shown by SEQ ID NO:17 (modified variant 23F2) (shown in figure as "RNA Sequence NO: 17-2") and human IgG1. The RNA having 16-residue Poly dA added to the 3' end thereof was immobilized onto a sensor chip via an dA-dT bond, IgG1 was injected, and the interaction with the RNA was examined.

The results above are summarized in Table 3-1 and Table 3-2. In Table 3, the strength of binding affinity is indicated by +; a larger number of + marks means higher affinity. How the RNA shown by SEQ ID NO:17 (modified variant 23F2) and IgG are bound together is shown in FIG. 31.

TABLE 3-1

| RNA aptamer | binding affinity |
|---|---|
| SEQ ID NO: 15 | ++++ |
| SEQ ID NO: 15 (modified variant 30F-1) | ++++ |
| SEQ ID NO: 15 (modified variant 30F-2) | ++++ |
| SEQ ID NO: 15 (modified variant 30F-3) | ++++ |
| SEQ ID NO: 15 (modified variant 30F-4) | ++++ |

TABLE 3-2

| RNA aptamer | binding affinity |
|---|---|
| SEQ ID NO: 17 | ++ |
| SEQ ID NO: 17 (modified variant 23F1) | ++ |
| SEQ ID NO: 17 (modified variant 23F2) | ++++ |
| SEQ ID NO: 17 (modified variant 23F3) | + |
| SEQ ID NO: 17 (modified variant 23F10) | ++++ |
| SEQ ID NO: 17 (modified variant 23F11) | +++ |
| SEQ ID NO: 17 (modified variant 23F12) | +++ |
| SEQ ID NO: 17 (modified variant 23F23) | ++++ |
| SEQ ID NO: 17 (modified variant 23F25) | ++++ |
| SEQ ID NO: 17 (modified variant 23F32) | ++ |
| SEQ ID NO: 17 (modified variant 23F33) | +++ |
| SEQ ID NO: 17 (modified variant 23F41) | ++++ |
| SEQ ID NO: 17 (modified variant 23F42) | ++++ |
| SEQ ID NO: 17 (modified variant 23F43) | ++++ |
| SEQ ID NO: 17 (modified variant 23F31) | ++++ |
| natural RNA | + |

Example 8

Bulge Structure of GGUGCU

To determine whether or not there is a sequence showing affinity for IgG, other than GGUGCU, optimization SELEX was performed. Used as the first pool was RNAs having the GGUGCU portion changed to a random sequence. This RNA pool was prepared by transcribing using the DuraScribe™ T7 Transcription Kit (manufactured by Epicentre) with the following chemically synthesized DNA as the template.

```
DNA template:
                                      (SEQ ID NO: 31)
5'-tgtcggccgttacagttccggtttcccgg-6N-tgtaactcgtccat
tgtccc-3'

Primer G:
                                      (SEQ ID NO: 32)
5'-taatacgactcactatagggacaatggacgagttac-3'

Primer H:
                                      (SEQ ID NO: 33)
5'-tgtcggccgttacagttc-3'
```

The theoretical variation of the RNA pool is 4096. As directed in the kit specifications, 40 μg of human IgG (Zymed Laboratories) was immobilized onto 40 μl of NHS-activated Sepharose resin (manufactured by Amasham Bioscience). SELEX was performed in the same manner as Example 1.

After completion of three rounds, the sequences were examined; 36 sequences of the 48 sequences comprised GGUGCU. Their secondary structures were examined using the MFOLD program; there was no sequence other than GGUGCU that forms the same bulge structure as that for GGUGCU. Using a surface plasmon resonance method, binding affinity was examined; there were no sequences other than GGUGCU that have binding affinity for human IgG.

Next, after completion of two rounds, 48 sequences were examined. There was one sequence comprising GGUGCU. The secondary structures of all sequences were estimated using the MFOLD program; the sequences comprising GGUGAU formed the same bulge structure as that for GGUGCU. Hence, the affinity between this clone and IgG was examined using surface plasmon resonance method; this clone was found to have binding affinity for IgG. The ACCGAC sequence was found in two clones, but this sequence did not bind to IgG. Using the MFOLD program, sequences that form the same bulge structure as that for GGUGCU, other than GGUGCU and GGUGAU, will be found. Hence, nucleic acids comprising such a sequence in place of the GGUGCU of the nucleic acid shown by SEQ ID NO:17 (modified variant 23F23) were chemically synthesized, and their binding affinities for human IgG1 were measured using a surface plasmon resonance method. Used in place of GGUGCU were the following sequences.

```
Sequence of bulge portion of SEQ ID NO: 17
(modified variant 23F23):
G(OH)G(OH)U(F)G(OH)C(H)U(F)

Sequence of bulge portion of SEQ ID NO: 17
(modified variant 23F23-1):
G(OH)A(OH)U(F)G(OH)C(H)U(F)

Sequence of bulge portion of SEQ ID NO: 17
(modified variant 23F23-2):
G(OH)C(F)U(F)G(OH)C(H)U(F)

Sequence of bulge portion of SEQ ID NO: 17
(modified variant 23F23-3):
G(OH)G(OH)C(F)G(OH)C(H)U(F)

Sequence of bulge portion of SEQ ID NO: 17
(modified variant 23F23-4):
G(OH)G(OH)U(F)A(OH)C(H)U(F)

Sequence of bulge portion of SEQ ID NO: 17
(modified variant 23F23)-5:
G(OH)G(OH)U(F)U(F)C(H)U(F)
```

None of SEQ ID NO:17 (modified variants 23F23-1 to 23F23-5) had binding affinity for human IgG1.

The GGUGCU of the nucleic acid shown by SEQ ID NO:17 (modified variant 23F23), like G(OH)G(OH)U(F)G(OH)C(F)U(F), has been fluorated at the 2'-position of the ribose of each pyrimidine base-containing nucleotide. Whether or not there is a sequence having binding affinity for human IgG was determined by other methods of modification. The nucleic acids used for the experiments were as shown below, and were prepared by chemical synthesis. Their binding affinities for human IgG1 were examined using a surface plasmon resonance method.

```
Sequence of bulge portion of SEQ ID NO: 17
(modified variant 23F23):
G(OH)G(OH)U(F)G(OH)C(H)U(F)

Sequence of bulge portion of SEQ ID NO: 17
(modified variant 23F23-101):
G(OH)G(F)U(F)G(OH)C(H)U(F)

Sequence of bulge portion of SEQ ID NO: 17
(modified variant 23F23-102):
G(OH)G(OH)U(OH)G(OH)C(H)U(F)
```

-continued

```
Sequence of bulge portion of SEQ ID NO: 17
(modified variant 23D23-103):
G(OH)G(OH)U(H)G(OH)C(H)U(F)

Sequence of bulge portion of SEQ ID NO: 17
(modified variant 23F23-104):
G(OH)G(OH)U(F)G(F)C(H)U(F)

Sequence of bulge portion of SEQ ID NO: 17
(modified variant 23F23-105):
G(OH)G(OH)U(F)G(OH)C(OH)U(F)

Sequence of bulge portion of SEQ ID NO: 17
(modified variant 23F23-106):
G(OH)G(OH)U(F)G(OH)C(H)U(OH)

Sequence of bulge portion of SEQ ID NO: 17
(modified variant 23F23-107):
G(OH)G(OH)U(F)G(OH)C(H)U(OMe)
```

As a result of the binding affinity measurements, modified variants 23F23-101 and 23F23-104 to 23F23-107 were found to have a binding affinity equivalent to that of SEQ ID NO:17 (modified variant 23F23). 23F23-102 and 23F23-103 did not have binding affinity.

These results are summarized in Table 4. In Table 4, the strength of binding affinity is indicated by +; a larger number of + marks means higher affinity.

TABLE 4

| RNA aptamer | binding affinity |
|---|---|
| SEQ ID NO: 17 (modified variant 23F23) | +++ |
| SEQ ID NO: 17 (modified variant 23F23-1) | − |
| SEQ ID NO: 17 (modified variant 23F23-2) | − |
| SEQ ID NO: 17 (modified variant 23F23-3) | − |
| SEQ ID NO: 17 (modified variant 23F23-4) | − |
| SEQ ID NO: 17 (modified variant 23F23-5) | − |
| SEQ ID NO: 17 (modified variant 23F23-101) | +++ |
| SEQ ID NO: 17 (modified variant 23F23-102) | − |
| SEQ ID NO: 17 (modified variant 23F23-103) | − |
| SEQ ID NO: 17 (modified variant 23F23-104) | +++ |
| SEQ ID NO: 17 (modified variant 23F23-105) | +++ |
| SEQ ID NO: 17 (modified variant 23F23-106) | +++ |
| SEQ ID NO: 17 (modified variant 23F23-107) | +++ |

Thus, the bulge structures of GGUGCU and GGUGAU were found to be important to the binding to IgG. It was also found that when the 3rd U of GGUGCU is a naturally occurring ribonucleotide (OH for the 2'-position of ribose) or deoxyribonucleotide (H for the 2'-position of ribose), the binding affinity is lost.

Example 9

Experiment of Method of IgG Purification Using RNA Aptamer

Figure 32:
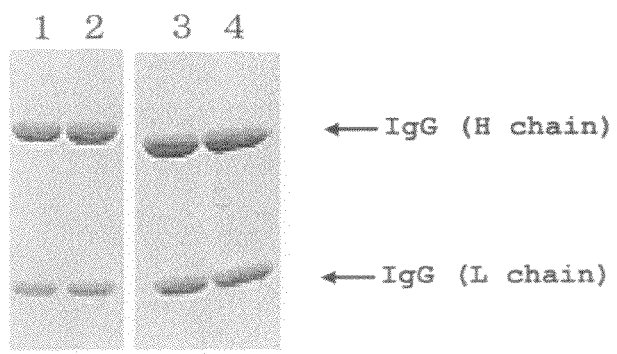
FIG. 32 shows the results of SDS-PAGE obtained when human IgG1 was pulled down using the RNAs shown by SEQ ID NO:15 and 17 as the ligands for a separating agent for antibody purification. The RNA having Poly (A) bound thereto was immobilized onto beads having Poly (dT) bound thereto, and human IgG1 was pulled down. Lane 1: the RNA shown by SEQ ID NO:15 was used as the ligand. Lane 2: the RNA shown by SEQ ID NO:17 was used as the ligand. Lane 3: Protein A was used as the ligand. Lane 4: rProtein A was used as the ligand.

The RNAs shown by SEQ ID NO:15 and 17 were immobilized on beads, and a pull-down experiment of human IgG1 was performed. Each 10 µL of Oligo(dT)-Cellulose beads (manufactured by Amersham Biosciences) was placed in a 200 µL tube (manufactured by Axygen), and coated with bovine serum albumin (manufactured by Boehringer Mannheim). Added thereto was about 10 µg of each RNA having 16 "A" units added to the 3' end thereof to achieve immobilization. The RNAs were prepared by chemically synthesizing a DNA template and primers (manufactured by Operon), and transcribing this using the DuraScribe™ T7 Transcription Kit (manufactured by Epicentre). After the unbound RNA was removed by washing with solution A, 20 µg of human IgG1 (Calbiochem) was added, and the mixture was kept at room temperature for 30 minutes. The human IgG1 that did not bind to the RNA was washed down with solution A. Next, a sample buffer was added to the beads, and the mixture was heated at 65° C. for 15 minutes, and analyzed by SDS-PAGE. A 6× sample buffer was prepared by mixing 1.3 g of sodium dodecyl sulfate (SDS), 3 mL of 2-mercaptoethanol, 4.2 mL of glycerin, and 1.5 mg of Bromophenol Blue. The results of SDS-PAGE are shown in FIG. 32. Lane 1 shows the result obtained using the aptamer of SEQ ID NO:15 as the ligand; lane 2 shows the result obtained using the aptamer of SEQ ID NO:17. The upper band is the band of the heavy chain (H chain) of IgG, and the lower band is the band of the light chain (L chain). It is seen that by using the RNA shown by SEQ ID NO:15 or 17 as the ligand for a separating agent for antibody purification, IgG can be pulled down.

10 µL of beads coupled with Protein A (manufactured by Amersham Biosciences) or beads coupled with Protein A deprived of the albumin binding region by gene recombination (rProtein A) (manufactured by Amersham Biosciences) was taken, 20 µg of human IgG1 was added, and IgG was purified in the same manner. Used as the eluent was a pH 3 glycine buffer. The results of SDS-PAGE analysis of the eluent are shown in FIG. 32. Lane 3 shows the result obtained with Protein A as the ligand; lane 2 shows the result obtained with rProtein A as the ligand. It is seen that the aptamer is capable of pulling down IgG with a performance equivalent to that of Protein A.

Figure 33:
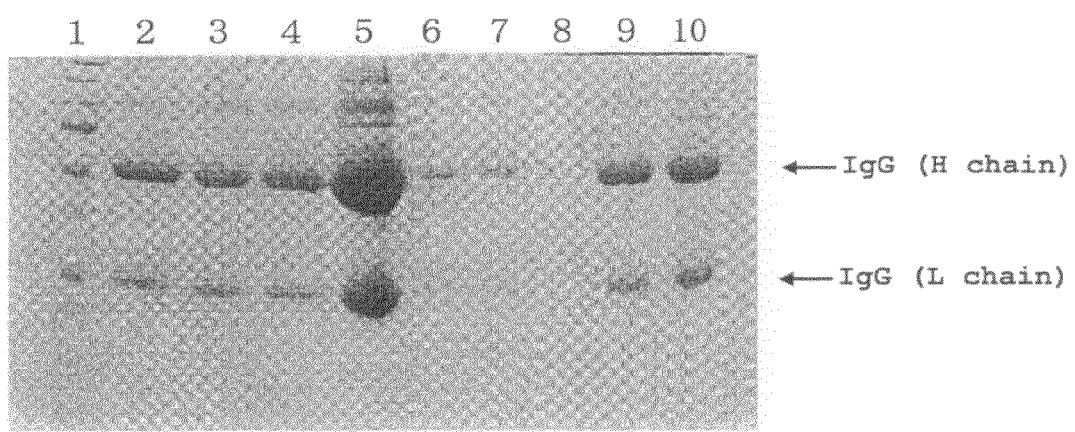
FIG. 33 shows the results of SDS-PAGE obtained when human IgG was purified from human serum using the RNA shown by SEQ ID NO:15 as the ligand for a separating agent for antibody purification. The RNA having biotin bound thereto was immobilized onto streptavidin beads, and IgG was pulled down from human serum. The IgG bound to the RNA was eluted using three kinds of neutral eluents. To determine whether or not IgG was efficiently eluted with the neutral eluents, a sample buffer was added to the beads after completion of elution, and the beads were heated and analyzed by SDS-PAGE. Lane 1: molecular weight marker protein. Lane 2: IgG eluted from the beads using the RNA as the ligand with an eluent consisting of 200 mM KCl and 10 mM EDTA. Lane 3: IgG eluted from the beads using the RNA as the ligand with an eluent consisting of 200 mM KCl, 10 mM EDTA and 10% glycerol. Lane 4: IgG eluted from the beads using the RNA as the ligand with an eluent consisting of 600 mM KCl, 10 mM EDTA, and 10% glycerol. Lane 5: IgG eluted with a pH 3 glycine buffer when IgG was pulled down using rProtein A Sepharose beads. Lane 6: IgG bound to the beads after being treated with the lane 2 eluent. Lane 7: IgG bound to the beads after being treated with the lane 3 eluent. Lane 8: IgG bound to the beads after being treated with the lane 4 eluent. Lane 9: IgG recovered with the addition of a sample buffer directly to the beads using the RNA as the ligand without subjecting the beads to elution treatment. Lane 10: IgG bound to the beads after being treated with the lane 5 eluent.

Whether or not human IgG could be purified from human serum using the RNA shown by SEQ ID NO:15 was determined. Also determined was whether or not IgG can be eluted with a neutral eluent. 10 µL of streptavidin-coupled Sepharose beads (manufactured by Amersham Biosciences) was placed in each 200 µL tube (manufactured by Axygen), and coated with bovine serum albumin. Added thereto was about 10 µg of the RNA with biotin bound to the 5' end thereof (manufactured by Gene Design) to achieve immobilization. After the unbound RNA was removed, 20 µL of human serum (manufactured by Chemicon International) was added, and this mixture was kept at room temperature for 30 minutes. The human serum components not bound to the RNA were washed down using an NaCl—$MgCl_2$ buffer. The NaCl—$MgCl_2$ buffer comprised 150 mM NaCl, 2.5 mM $MgCl_2$, and pH 7.6 20 mM Tris buffer. The IgG bound to the RNA was eluted using a neutral eluent. Used as the neutral eluents were (1) a 200 mM KCl+10 mM EDTA mixed solution, (2) a 200 mM KCl+10 mM EDTA+10% glycerol mixed solution, and (3) a 600 mM KCl+10 mM EDTA+10% glycerol mixed solution. To determine the amount of IgG recovered, the eluent was analyzed by SDS-PAGE. To determine the amount of IgG bound to the beads without being eluted, a sample buffer was added to the beads after removing the eluent, and the mixture was heated at 65° C. for 15 minutes, and analyzed by SDS-PAGE. The results of SDS-PAGE are shown in FIG. 33. From lanes 2 to 4, it is seen that human IgG can be pulled down from serum at high purity using aptamer resin. From the fact that almost no IgG was detected in lanes 6 to 8, it is seen that human IgG can be eluted using a neutral eluent.

10 µL of the beads bound with rProtein A was taken, 20 µL of human serum was added, and IgG was purified in the same manner. Used as the eluent was a pH 3 glycine buffer. The results of analysis of the eluent and beads by SDS-PAGE are shown in FIG. 33. Although there is a difference in the volume of IgG adsorbed, it is seen that the aptamer resin is capable of purifying IgG with a purity about equivalent to that of rProtein A resin. The aptamer resin can be said to surpass rProtein A resin in that IgG can be eluted under neutral conditions when the aptamer resin is used.

The same experiment was performed using mouse serum (manufactured by Chemicon International). When rProtein A was used, IgG became pulled down, whereas when the RNA shown by SEQ ID NO:15 was used, IgG did not become pulled down. It is seen that the RNA ligand for antibody purification of the present invention is capable of purifying a human antibody alone at high purity.

Figure 34:
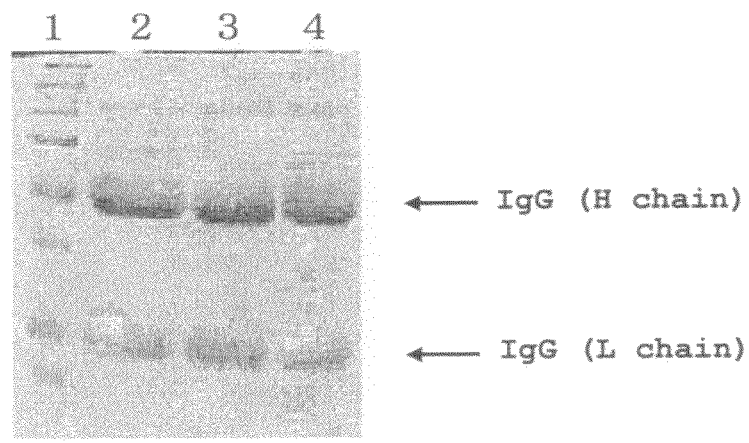
FIG. 34 shows the results of SDS-PAGE obtained in a test performed to determine whether or not the RNA shown by SEQ ID NO:15 can be repeatedly used as a ligand for a separating agent for antibody purification. The RNA-bound separating agent once used for antibody purification was washed with urea, and antibody purification was performed again. This was twice repeated. Lane 1: molecular weight marker protein. Lane 2: IgG obtained by first purification. Lane 3: IgG obtained by second purification. Lane 4: IgG obtained by third purification.

A test was performed to determine whether or not the RNA shown by SEQ ID NO:15 can be used repeatedly as a ligand for a separating agent for antibody purification. As described above, about 10 μg of the RNA with biotin bound thereto was immobilized onto 10 μL of streptavidin beads, human serum was added, and IgG was eluted with a neutral solution. Thereafter, the beads were washed with 50 μL of 6 M urea three times, and the beads were further washed with NaCl—MgCl$_2$ buffer three times to remove the urea, after which 20 μL of human serum was added again, and IgG was eluted with a neutral solution. This was performed again, and the amount of IgG recovered in the three times of antibody purification was confirmed by SDS-PAGE (FIG. 34). As a result, it was found that the amount of IgG pulled down did not differ widely among the three times of antibody purification. This shows that the RNA ligand for antibody purification can be washed with urea and regenerated. Likewise, washing was performed with 0.1 M NaOH. Although the antibody was purified repeatedly three times, the amount of IgG recovered did not decrease widely.

Figure 35:
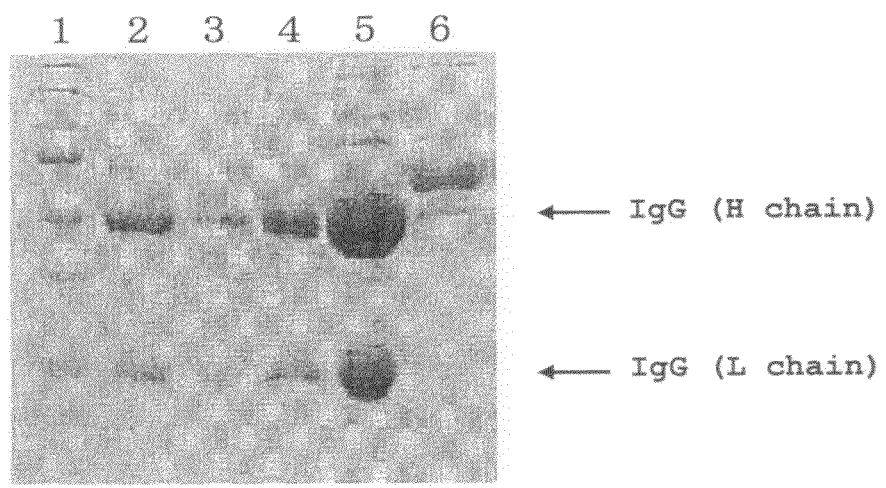
FIG. 35 shows the results of SDS-PAGE obtained when human IgG was purified from human serum using the RNAs shown by SEQ ID NO:16 and SEQ ID NO:17 (modified variant 23F2) as the ligands for a separating agent for antibody purification. Lane 1: molecular weight marker protein. Lane 2: IgG pulled down when the RNA shown by SEQ ID NO:15 was used as the ligand. Lane 3: IgG pulled down when the RNA shown by SEQ ID NO:16 was used as the ligand. Lane 4: IgG pulled down when the RNA shown by SEQ ID NO:17 (modified variant 23F2) was used as the ligand. Lane 5: IgG pulled down when rProtein A was used as the ligand. Lane 6: human serum.

Next, biotin was bound to the 5' end of each of the RNA shown by SEQ ID NO:16 and the RNA shown by SEQ ID NO:17 (modified variant 23F2), and IgG was purified from human serum as described above. As a result, it was found that IgG could be purified at high purity using these RNA ligands (FIG. 35).

Thus, it was found that by using an RNA aptamer as the ligand, human IgG can be purified at high efficiency and at high purity from human serum under neutral conditions.

Example 10

Figure 36:
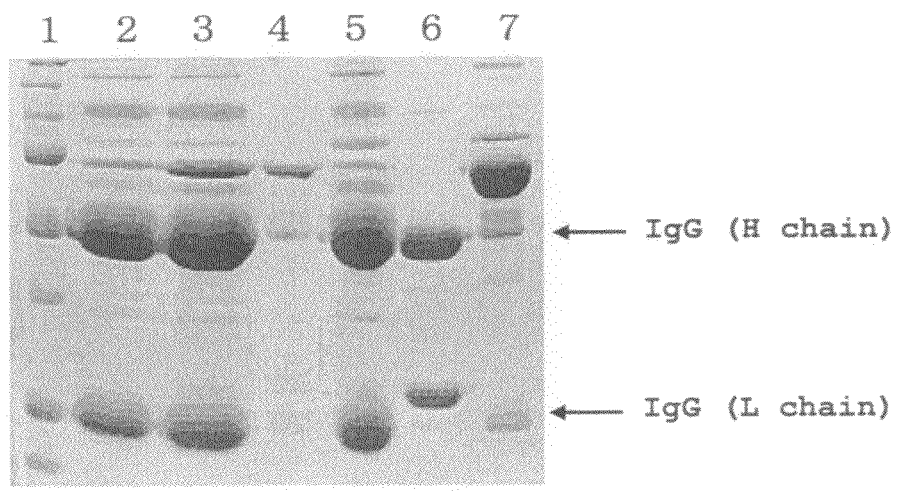
FIG. 36 shows the results of SDS-PAGE obtained when antibody purification was performed using an RNA aptamer immobilized by thiol coupling. Lane 1: molecular weight marker protein. Lane 2: IgG pulled down when the RNA shown by SEQ ID NO:15 was used as the ligand, with the addition of 5 µL of human serum. Lane 3: IgG pulled down when the RNA shown by SEQ ID NO:15 was used as the ligand, with the addition of 10 µL of human serum. Lane 4: blank (serum protein pulled down when 5 µL of human serum was added to beads not having a ligand bound thereto). Lane 5: IgG pulled down when rProtein A beads were used, with the addition of 5 µL of human serum. Lane 6: standard human IgG1. Lane 7: human serum.

Experiments of Method for IgG Purification Using RNA Aptamer Immobilized by Thiol Coupling The RNA shown by SEQ ID NO:15 was immobilized onto beads by thiol coupling, and a pull-down experiment was performed in the same manner as Example 9. A thiol group was bound to the 5' end of the RNA shown by SEQ ID NO:15 via a C18 linker (manufactured by Gene Design). About 20 μg of this RNA was immobilized onto 10 μL of Activated Thiol Sepharose beads (manufactured by Amersham Bioscience). Immobilization was performed as directed in the kit specifications. The amount immobilized was estimated by measuring the amount of the RNA before immobilization and the amount of RNA in the supernatant immediately after immobilization using an absorption photometer. As a result, it was found that more than 90% of the RNA used for coupling was immobilized. A pull-down experiment was performed using the RNA aptamer beads in the same manner as Example 9. 5 μL and 10 μL of human serum was added to 10 μg of beads, and the beads were washed, eluted with a neutral eluent, and analyzed by SDS-PAGE (FIG. 36). As a result, it was shown that IgG was pulled down at high purity (FIG. 36 lanes 2 and 3).

A pull-down experiment using rProtein A beads was performed in the same manner as Example 9. 5 μL of human serum was added to 10 μL of rProtein A beads, and the beads were washed, after which a sample buffer for SDS-PAGE was added, and the mixture was heated at 65° C. for 15 minutes, and analyzed by SDS-PAGE (FIG. 36 lane 5).

From the results of this pull-down experiment, it was found that using RNA aptamer beads immobilized by thiol coupling, human IgG could be purified at high efficiency and at high purity from human serum under neutral conditions.

Example 11

Figure 37:
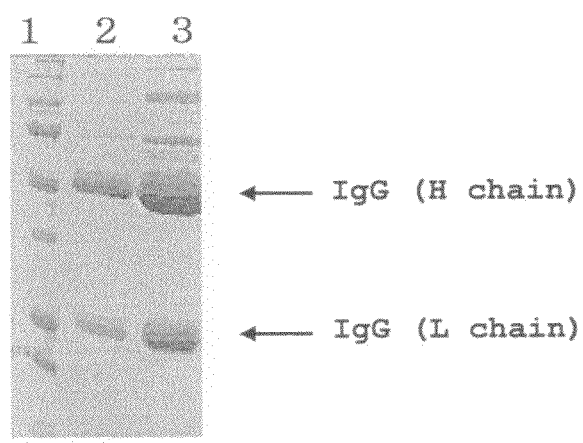
FIG. 37 shows the results of SDS-PAGE obtained when antibody purification was performed using an RNA aptamer immobilized by amino coupling. Half of the volume of recovered sample was applied. Lane 1: molecular weight marker protein. Lane 2: IgG recovered from 10 µl of human serum using the RNA shown by SEQ ID NO:15 (amount immobilized 25 µg) as the ligand. Lane 3: IgG recovered from 10 µl of human serum using the RNA shown by SEQ ID NO:15 (amount immobilized 75 µg) as the ligand.
Figure 38:
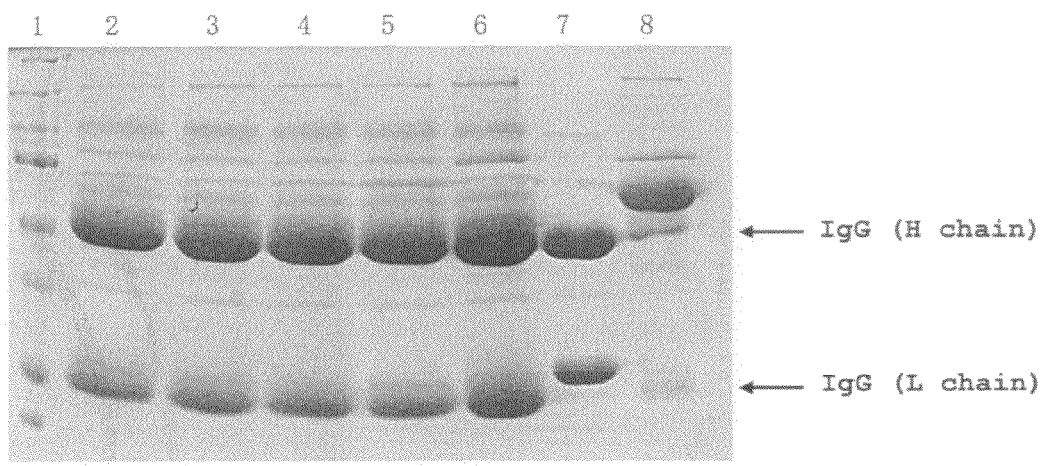
FIG. 38 shows the results of SDS-PAGE obtained when antibody purification was performed using an RNA aptamer immobilized by amino coupling. For pulling-down, 10 µL of human serum was used. Lane 1: molecular weight marker protein. Lane 2: the RNA shown by SEQ ID NO:17 (modified variant 23F23) was used as the ligand. Lane 3: the RNA shown by SEQ ID NO:17 (modified variant 23F25) was used as the ligand. Lane 4: the RNA shown by SEQ ID NO:17 (modified variant 23F23-107) was used as the ligand. Lane 5: the RNA shown by SEQ ID NO:15 was used as the ligand. Lane 6: rProtein A resin was used. Lane 7: standard human IgG1 (6 µg). Lane 8: human serum (0.2 µL).

Experiments of Method of IgG Purification Using RNA Aptamer Immobilized by Amino Coupling An amino group was bound to the 5' end of RNA via a C12 linker, and an RNA was immobilized onto the resin by amino coupling. The amino group-coupled RNA was prepared by chemical synthesis (manufactured by Gene Design). For immobilization of the RNA, Tresyl-TOYOPEARL resin (manufactured by Tosoh Corporation) was used. Using 10 mg of the RNA per ml of the resin, about 8 mg of the RNA was immobilized. The amount immobilized was determined by measuring the amount of RNA in the supernatant using an absorption photometer both before and after coupling. An experiment of pulling down IgG from human serum was performed using this aptamer resin in the same manner as Example 9. Used as the ligands were the RNAs shown by SEQ ID NO:15 (FIG. 37) and SEQ ID NO:17 (modified variant 23F23), SEQ ID NO:17 (modified variant 23F25), SEQ ID NO:17 (modified variant 23F23-107), SEQ ID NO:15 (FIG. 38). As a result, it was shown that IgG was pulled down from all these aptamer resins at a purity equivalent to that with rProtein A resin (FIGS. 37 and 38).

Figure 39:
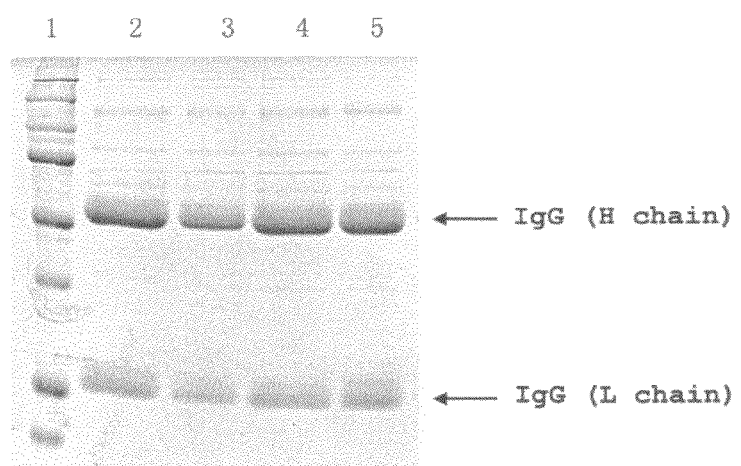
FIG. 39 shows the results of SDS-PAGE when elution was performed using various eluents. Lane 1: molecular weight marker protein. Lane 2: 200 mM KCl+10 mM EDTA+pH 7.6 10 mM Tris. Lane 3: 200 mM KCl+pH 7.6 10 mM Tris. Lane 4: 300 mM NaCl+10 mM EDTA+pH 7.6 10 mM Tris. Lane 5: 10 mM EDTA+pH 7.6 10 mM Tris.

In Example 9, it was shown that when an aptamer resin was used, IgG could be eluted with a 200 mM KCl+10 mM EDTA neutral eluent. Here, using the aptamer resin shown by SEQ ID NO:17 (modified variant 23F23), immobilized by amino coupling, experiments of IgG elution with neutral eluents with different ingredients were performed. Used as the eluents were (1) 200 mM KCl+10 mM EDTA+pH 7.6 10 mM Tris, (2) 200 mM KCl+pH 7.6 10 mM Tris, (3) 300 mM NaCl+10 mM EDTA+pH 7.6 10 mM Tris, and (4) 10 mM EDTA+pH 7.6 10 mM Tris. In the same manner as Example 9, IgG was pulled down from human serum, eluted with the above-described eluent, and analyzed using SDS-PAGE. As a result, it was found that IgG could be eluted with KCl or EDTA alone (FIG. 39).

Whether or not IgG can be eluted with 1 M NaCl solution was determined. Because nucleic acids bear a negative charge, it is generally thought that an ionic bond is important for the binding to protein. Hence, the binding to protein can be broken using a solution with a high salt concentration. With 1 M NaCl solution as the eluent, the same experiment was performed as described above; IgG was not detected in the eluent, most of which remained adsorbed to the aptamer resin. To confirm that the aptamer and IgG are bound together in the presence of high concentrations of NaCl, an experiment using a surface plasmon resonance method was performed. Used as the running buffer was a 500 mM NaCl+2 mM MgCl$_2$+10 mM pH 7.6 Tris mixture. As a result, it was found that the binding affinity did not decrease at all even in the presence of 500 mM NaCl.

Thus, it was found that the IgG bound to the aptamer resin could be eluted with 200 mM KCl solution, but could not be eluted with 1 M NaCl solution.

Figure 40:
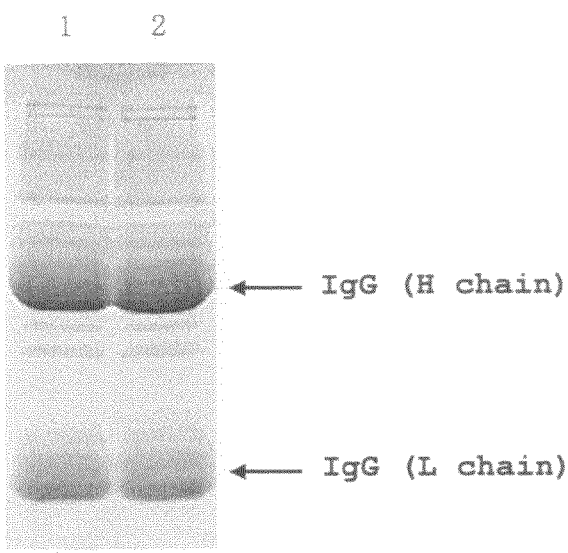
FIG. 40 shows the results of SDS-PAGE performed for evaluating the characteristics of thermally regenerated aptamer resins. 10 µL of each aptamer resin, already used three times, was subjected to heat treatment by two methods, and a pull-down experiment was performed again using 10 µL of human serum. Neutrally eluted fractions were analyzed by SDS-PAGE. Lane 1: the aptamer resin shown by SEQ ID NO:17 (modified variant 17-18), heated in ultrapure water at 85° C. for 5 minutes. Lane 2: the aptamer resin shown by SEQ ID NO:17 (modified variant 17-17), heated in 6 M urea at 65° C. for 15 minutes.

Next, an experiment for the regeneration and sterilization of aptamer resin by heating was performed. The aptamer resin shown by SEQ ID NO:17 (modified variant 17-17) or SEQ ID NO:17 (modified variant 17-18), after being used three times, was (1) heated at 85° C. for 5 minutes with the addition of ultrapure water or (2) heated at 65° C. for 15 minutes with the addition of 6M urea, and a pull-down experiment was performed again. 10 μL of human serum was used; used as the eluent was 200 mM KCl+10 mM EDTA+pH 7.6 10 mM Tris solution. The eluent was analyzed by SDS-PAGE; it was found that the aptamer resin was hardly deteriorated by heat treatment with (1) and (2) (FIG. 40).

Whether or not IgG can be purified in dynamic state was determined. 100 μL of the aptamer resin was packed in a small column (MoBiTec/mobicols), and 100 μL of human serum was added. Soon after that, solution A was added using a syringe to wash the resin (solution A: 4 mL, flow rate about 1 mL/min). Next, the IgG bound to the aptamer ligand was eluted using a neutral eluent (neutral eluent: 2 mL, flow rate about 1 mL/min). The fraction eluted was examined using SDS-PAGE; it was confirmed that IgG was eluted. The absorbance of each fraction was measured, and the amount of IgG purified dynamically was calculated; it was found that 3.5 mg of IgG per mL of resin could be purified by one time of purification.

Example 12

IgG Pull-Down Experiment Using Resin-Bound Oligo

Figure 41:
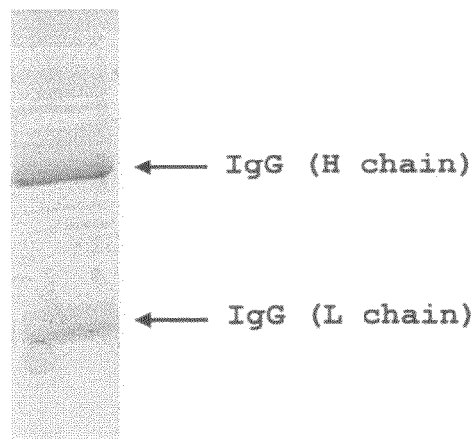
FIG. 41 shows the results of SDS-PAGE of IgG purified with resin-bound oligo. 10 µL of human serum was added to 10 µL of the resin-bound oligo having the RNA shown by SEQ ID NO:15 bound thereto covalently, and the fraction eluted with neutral eluent was analyzed by SDS-PAGE.

In the foregoing examples, an aptamer prepared by chemical synthesis was used after being immobilized on the resin via a polyA-polydT bond, a biotin-streptavidin bond, thiol coupling, or amino coupling. However, the nucleic acid was synthesized in a state immobilized onto the resin, and used after being cleaved from the resin after synthesis. Hence, for the purpose of shortening the step for cleaving the nucleic acid from the resin and re-binding the nucleic acid to the resin, nucleic acid was used as is, without being cleaved from the resin, for the pull-down experiment after completion of synthesis (resin-bound oligo). Used as the resin-bound oligo was the RNA shown by SEQ ID NO:15, synthesized on the Oligo affinity support (manufactured by Glen Research) (manufactured by Gene Design). 10 μL of human serum was added to 10 μL of the resin, and IgG was pulled down, and eluted with a neutral eluent; IgG was purified at high purity (FIG. 41).

Example 13

Evaluation of Binding Affinity for Chimeric Antibody

Figure 42:
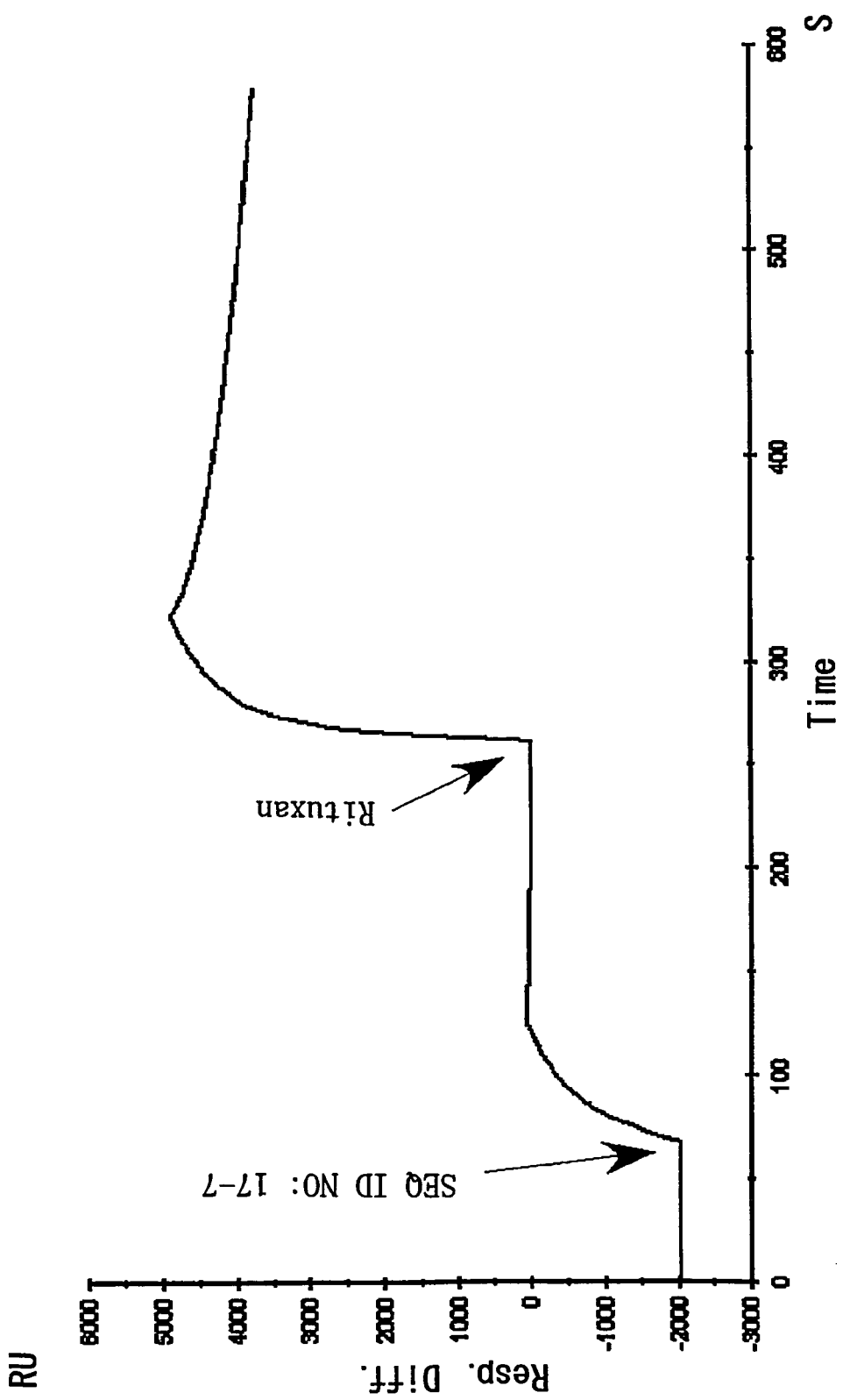
FIG. 42 shows a sensorgram obtained by surface plasmon resonance analysis, showing the profile of the binding of the RNA shown by SEQ ID NO:17 (modified variant 23F23) (shown in figure as SEQ ID NO:17-7) and the antibody drug Rituxan. The RNA having 16-residue Poly A added to the 3' end thereof was immobilized onto a sensor chip via an A-dT bond, Rituxan was injected, and the interaction with the RNA was examined.

Whether or not this aptamer has binding affinity for an antibody for pharmaceutical use prepared using gene recombination technology was determined using a surface plasmon resonance method. Used as the antibody was Rituxan (manufactured by Roche), a pharmaceutical in actual use; used as the ligand was the nucleic acid shown by SEQ ID NO:17 (modified variant 23F23). As a result of the measurements, it was found that the nucleic acid shown by SEQ ID NO:17 (modified variant 23F23) had binding affinity for Rituxan (FIG. 42).

INDUSTRIAL APPLICABILITY

Provided by the present invention is a nucleic acid ligand having the capability of binding to IgG. The nucleic acid ligand provided by the present invention retains high binding affinity and specificity for IgG. Also, because the nucleic acid ligand can be synthesized chemically, it allows easy alteration or modification of the nucleotide sequence. Therefore, when an antibody is utilized for a pharmaceutical, a chemical reagent, or a diagnostic reagent, it is easily possible to alter the binding affinity or stability thereof according to respective needs, and to add new functions by binding a fluorescent substance, an anticancer agent and the like. In recent years, humanized monoclonal antibodies have been brought into practical applications as molecular-targeted drugs, and antibody preparations are being developed worldwide. Hence, it is expected that highly functional separating agents will be developed as substitutes for Protein A resin-based separating agents, which are currently in use for antibody purification, and the scale of the market for such separating agents is expected to amount to about 50 billion yen. The nucleic acid ligand provided by the present invention can be used as ligands of a separating agent for antibody purification, and makes it possible to purify a desired antibody under neutral conditions easily at high purity. This aspect is widely different from the conventional purification under acidic conditions using Protein A in that the antibody is unlikely to lose activity during purification. The nucleic acid ligand provided by the present invention can be utilized for general purposes as a novel linker for binding an antibody and a fluorescent substance or an enzyme, as a novel immobilizing agent for immobilizing an antibody to a substrate or resin, and as a novel linker for binding an antibody and an anticancer agent or a toxin. The present invention is expected to find general-purpose applications as a tool of industrialization and investigation of novel separating agents, chemical reagents, and pharmaceuticals concerning antibodies, having a major economic effect.

This application is based on a patent application No. 2005-195717 filed in Japan on Jul. 5, 2005 and U.S. provisional application No. 60/749,026 filed in the US on Dec. 12, 2005, the contents of which are incorporated in full herein by this reference.

The invention claimed is:

1. An aptamer which binds to IgG and satisfies the requirement (a) or (b):
   (a) an aptamer no more than 40 nucleotides in length comprising a nucleotide sequence shown by any of SEQ ID NOs:13-18, wherein:
      (1) uracil may be substituted by thymine,
      (2) the aptamer is capable of forming a secondary structure represented by following formula:

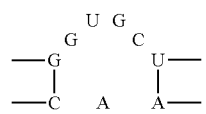

wherein a uracil at a third position in GGUGCU is substituted with a fluorine atom at a 2' position of ribose; and solid horizontal lines indicate other nucleotides; or
   (b) an aptamer no more than 40 nucleotides in length comprising a nucleotide sequence shown by any of SEQ ID NOs:13-18, wherein:
      (1) uracil may be substituted by thymine,
      (2) the aptamer is capable of forming a secondary structure represented by following formula:

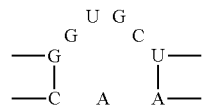

wherein a uracil at a third position in GGUGCU is substituted with a fluorine atom at a 2' position of ribose; and solid horizontal lines indicate other nucleotides,
      (3) one to four nucleotides other than GGUGCU and AAC are substituted, deleted, inserted or added.

2. An aptamer which binds to IgG and satisfies the requirement (a) or (b):
   (a) an aptamer no more than 40 nucleotides in length comprising a nucleotide sequence shown by any of SEQ ID NOs:13-18, wherein:
      (1) uracil may be substituted by thymine,
      (2) the aptamer is capable of forming a secondary structure represented by following formula:

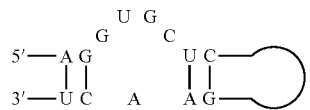

wherein a uracil at a fourth position in AGGUGCUC is substituted with a fluorine atom at a 2' position of ribose; and solid lines other than vertical lines indicate other nucleotides; or
   (b) an aptamer no more than 40 nucleotides in length comprising a nucleotide sequence shown by any of SEQ ID NOs:13-18, wherein:
      (1) uracil may be substituted by thymine,
      (2) the aptamer is capable of forming a secondary structure represented by following formula:

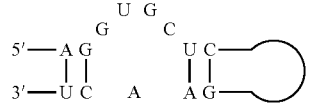

wherein a uracil at a fourth position in AGGUGCUC is substituted with a fluorine atom at a 2' position of ribose; and solid lines other than vertical lines indicate other nucleotides,
      (3) one to four nucleotides other than GGUGCU and AAC are substituted, deleted, inserted or added.

3. The aptamer of claim 1, wherein the nucleotide sequence shown by any of SEQ ID NOs:13-18 is the nucleotide sequence shown by SEQ ID NO:17.

4. The aptamer of claim 2, wherein the nucleotide sequence shown by any of SEQ ID NOs:13-18 is the nucleotide sequence shown by SEQ ID NO:17.

5. The aptamer of claim 1, wherein at least one nucleotide in the aptamer is modified by a member selected from the group consisting of a hydrogen atom, a fluorine atom, a hydroxyl group and an —O-Me group at a 2' position of ribose.

6. A method for human IgG purification comprising adsorbing human IgG to a solid phase carrier having the aptamer of claim 1, and eluting the adsorbed human IgG with an eluent.

7. A diagnostic or testing reagent comprising the aptamer of claim 1.

8. A pharmaceutical comprising the aptamer of claim 1.

9. A method for human IgG purification comprising adsorbing human IgG to a solid phase carrier having the aptamer of claim 5, and eluting the adsorbed human IgG with an eluent.

10. A diagnostic or testing reagent comprising the aptamer of claim 5.

11. A pharmaceutical comprising the aptamer of claim 5.

12. The aptamer of claim 2, wherein at least one nucleotide in the aptamer is modified by a member selected from the group consisting of a hydrogen atom, a fluorine atom, a hydroxyl group and an —O-Me group at a 2' position of ribose.

13. A method for human IgG purification comprising adsorbing human IgG to a solid phase carrier having the aptamer of claim 2, and eluting the adsorbed human IgG with an eluent.

14. A diagnostic or testing reagent comprising the aptamer of claim 2.

15. A pharmaceutical comprising the aptamer of claim 2.

16. An aptamer no more than 40 nucleotides in length which binds to IgG and comprises a nucleotide sequence shown by any of SEQ ID NOs:13-18, wherein:

(1) uracil may be substituted by thymine,
(2) the aptamer is capable of forming a secondary structure represented by following formula:

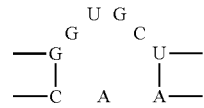

wherein a uracil at a third position in GGUGCU is substituted with a fluorine atom at a 2' position of ribose; and solid horizontal lines indicate other nucleotides.

17. The aptamer of claim 16, wherein at least one nucleotide in the aptamer is modified by a member selected from the group consisting of a hydrogen atom, a fluorine atom, a hydroxyl group and an —O-Me group at a 2' position of ribose.

18. The aptamer of claim 16, wherein the nucleotide sequence shown by any of SEQ ID NOs:13-18 is the nucleotide sequence shown by SEQ ID NO:17.

19. An aptamer no more than 40 nucleotides in length which binds to IgG and comprises a nucleotide sequence shown by SEQ ID NO:17.

20. A conjugate comprising more than one aptamer of claim 1.

21. A conjugate comprising more than one aptamer of claim 2.

* * * * *